US009963745B2

(12) United States Patent
Mai et al.

(10) Patent No.: US 9,963,745 B2
(45) Date of Patent: May 8, 2018

(54) HEMATOLOGICAL DISORDER DIAGNOSIS BY 3D Q-FISH

(71) Applicants: 3D Signatures Holdings Inc., Toronto (CA); Tokunbo Ibikunle, Haverford, PA (US)

(72) Inventors: Sabine Mai, Winnipeg (CA); Hans Knecht, Magog (CA); Macoura Gadji, Winnipeg (CA); Ade Olujohungbe, Winnipeg (CA)

(73) Assignee: 3D Signatures Holdings Inc., Toronto (CA)

( * ) Notice: Subject to any disclaimer, the term of this patent is extended or adjusted under 35 U.S.C. 154(b) by 68 days.

(21) Appl. No.: 13/692,645

(22) Filed: Dec. 3, 2012

(65) Prior Publication Data

US 2013/0178435 A1    Jul. 11, 2013

Related U.S. Application Data

(60) Provisional application No. 61/566,348, filed on Dec. 2, 2011.

(30) Foreign Application Priority Data

Dec. 2, 2011    (CA) ..................................... 2760873

(51) Int. Cl.
 *C12Q 1/68*    (2018.01)
(52) U.S. Cl.
 CPC ...... *C12Q 1/6886* (2013.01); *C12Q 2600/118* (2013.01)
(58) Field of Classification Search
 None
 See application file for complete search history.

(56) References Cited

U.S. PATENT DOCUMENTS

| 6,506,563 | B1 | 2/2003 | Speicher Michael et al. |
| 7,801,682 | B2 | 9/2010 | Mai et al. |
| 8,084,203 | B2 | 12/2011 | Flores Hernandez et al. |
| 2007/0031831 | A1 | 2/2007 | Mai et al. |
| 2010/0143903 | A1 | 6/2010 | Mai et al. |

FOREIGN PATENT DOCUMENTS

| WO | 00/55174 A1 | 9/2000 |
| WO | 02/46465 A2 | 6/2002 |
| WO | 2004/074500 A2 | 9/2004 |

OTHER PUBLICATIONS

Remes, "Telomere length and telomerase activity in malignant lymphomas at diagnosis and relapse," British Journal of Cancer, vol. 82, pp. 601-607, 2000.*
Verweij, "Achievements and future of chemotherapy," Eur J Cancer, vol. 36, pp. 1479-1487, 2000.*
Laboratory Hematology. Atlas of blood smear analysis. Retrieved from the Internet on May 17, 2013 <URL http://www.chronolab.com/hematology/3_4_9.htm>.
The identification of mature and immature blood cells in peripheral blood smears and bone marrow preparations is fundamental to the laboratory diagnosis of haematological disorders Retrieved from the internet on Apr. 2, 2014 <http://www.docstoc.com/docs/14917377/The-identification-of-mature-and-immature-blood-cells-in-peripheral-blood-smears-and-bone-marrow-preparations-is-fundamental-to-the-laboratory-diagnosis-of-haematological-disorders-Here-you>.
Mai Sabine et al. 3D nuclear parameters define CTC subpopulations. Slides presented at the Word Summit of CTCs on Apr. 25, 2012 in Berlin.
Gadji M., et al. Nuclear remodeling as a mechanism for genomic instability in cancer. Adv. Cancer Research, 2011, vol. 112, pp. 77-126.
Knecht H., et al. 3D nuclear organization of telomeres in the Hodgkin cell lines U-HO1 and U-HO1-PTPN1: PTPN1 expression prevents the formation of very short telimeres including "t-stumps". BMC Cell Biol. Dec. 14, 2010, 11:99.
Knecht, H. et al. 3D imaging of telomeres and nuclear architecture: An emerging tool of 3D nano-morphology-based diagnosis. J. Cell. Physiol., Apr. 2011, vol. 226, No. 4, pp. 859-867.
Guffei A., et al. Dynamic chromosomal rearrangements in Hodgkin's lymphoma are due to ongoing three-dimensional nuclear remodeling and breakage-bridge-fusion cycles. Haematologica, Dec. 2010, vol. 95, No. 12, pp. 2038-2046.
Knecht H., et al. 3D structural and functional characterization of the transition from Hodgkin to Reed-Sternberg cells. Ann. Anat., Sep. 20, 2010, vol. 192, No. 5, pp. 302-308.
Knecht H., et al. 3D Telomere FISH defines LMP1-expressing Reed-Sternberg cells as end-stage cells with telomere-poor 'ghost' nuclei and very short telomeres. Lab Invest., Apr. 2010, vol. 90, No. 4, pp. 611-619.
Lansdorp, Peter M. et al. Heterogeneity in telomere length of human chromosomes. Human Molecular Genetics, 1996, vol. 5, No. 5, pp. 685-691.
Maierhofer Christine et al. Multicolor deconvolution microscopy of thick biological specimens. American Journal of Pathology, vol. 162, Feb. 1, 2003, pp. 373-379.
Henderson et al. In situ analysis of changes in telomere size during replicative aging and cell transformation. The Journal of Cell Biology, vol. 134, No. 1, Jul. 1996, pp. 1-12.
Schaefer L. H. et al. Generalized approach for accelerated maximum likelihood based image restoration applied to three-dimensional fluorescence microscopy. Journal of Microscopy, vol. 204, Nov. 2001, pp. 99-107.
Bass Hank W. et al. Telomeres cluster de novo before the initiation of synapsis: A three-dimensional spatial analysis of telomere positions before and during meiotic porphase. Journal of Cell Biology, vol. 137, No. 1, 1997, pp. 5-18.
Raz, Vered, et al. Changes in lamina structure are followed by spatial reorganization of heterochromatic regions in caspase-8-activated human mesenchymal stem cells. Journal of Cell Science, vol. 119, No. 20, Sep. 26, 2006, pp. 4247-4256.
Gonzalez-Suarez, Ignacio et al. Novel roles for A-type lamins in telomere biology and the DNA damage response pathway. The EMBO Journal, vol. 28, 2009, pp. 2414-2427.

(Continued)

*Primary Examiner* — G. Steven Vanni
(74) *Attorney, Agent, or Firm* — Bereskin & Parr LLP; Carmela De Luca

(57) ABSTRACT

Provided are methods for prognosing a clinical outcome in a subject with a hematological disorder comprising determining a 3D telomeres organization signature of a test sample cell from the subject, wherein the 3D telomeres organization signature of the test sample cell is indicative of the clinical outcome of the subject.

24 Claims, 17 Drawing Sheets

(56) References Cited

OTHER PUBLICATIONS

Weierich Claudia, et al. Three-dimensional arrangements of Centromeres and Telomeres in Nuclei of Human and Murine Lymphocytes. Chromosome Research, vol. 11, 2003, pp. 485-502.
Chuang Tony Chin Yuan et al. The Three-dimensional Organization of Telomeres in the Nucleus of Mammalian Cells, Retrieved from the Internet, <URL: http://www.biomedcentral.com/1741-7007/2/12> Jun. 2004.
Martin-Subero, J. I. et al. Multicolor FICTION. Expanding the possibilities of combined morphologic, immunophenotypic, and genetic single cell analysis. American Journal of Pathology, Aug. 2002, vol. 161, No. 2, pp. 413-420.
Vermolen, B. J. et al. Three-dimensional analysis tool for segmenting and measuring the structure of telomeres in mammalian nuclei In: Imaging, Manupulation and Analysis of Biomolecules and Cells: Fundamentals and Applications III, D.V. Edited by D.V. Nicolau et al. Bellingham, WA: spie, 2005, Proceedings of the SPIE, vol. 5699, pp. 111-120. Retrieved from the Internet on Dec. 2005 <URL: http://www.ph.tn.tudelft.nl/People/albert/papers/Vermolen5699_17.pdf>.
Cizeau Jeannick et al. The C. elegans orthologue ceBNIP3 interacts with CED-9 and CED-3 but kills through a BH3- and caspase-independent mechanism. Oncogene, vol. 19, No. 48, Nov. 16, 2000, pp. 5453-5463.
Chen Gao et al. Nix and Nip3 form a subfamily of pro-apoptotic mitochondrial proteins. Journal of Biological Chemistry, vol. 274, No. 1, Jan. 1, 1999, pp. 7-10.
Eisenstat, David. NBTF Progress Report—Oligo Fund. Nov. 15, 2005, NBTF website, Retrieved from the Internet <URL: http://www.braintumor.org/research/past_recipients/2004_reports/Eisenstat_Oligo_detail.pdf>.
Guo K., et al. Hypoxia induces the expressions of the pro-apoptotic gene BNIP3. Cell Death and Differentiation, 2001, vol. 8, pp. 367-376.
Lee H. et al. Regulation of BNIP3 in normal and cancer cells. Molecules and Cells, 2006, vol. 21, No. 1, pp. 1-6.
Zhou J. et al. Tumor hypoxia and cancer prevention. 2006, Cancer Letters, vol. 237, pp. 10-21.
Burton T. R. et al. The pro-cell kdeath BCL-2 family member BNIP3, is localized to the nucleus of human glial cells: implications for glioblastoma multiforme tumor cell survival under hypoxia. International Journal of Cancer, 2006, vol. 118, pp. 1660-1669.
Reiger R. et al. Glossary of genetics and cystogenetics. Springer-Verlag, 1976, pp. 17-18.
Vande Velde C. et al. BNIP3 and genetic control of necrosis-like cell death through the mitochondrial permeability transition pore. Molecular and Cellular Biology, Aug. 2000, vol. 20, No. 15, pp. 5454-5468.
Kothari S. et al. BNIP3 plays a role in hypoxic cell death in human epithelial cells that is inhibited by growth factors EGF and IGF. Oncogene, Jul. 24, 2003, vol. 22, No. 30, pp. 4734-4744.
Aubele M. et al. Comparative FISH analysis of numerical chromosome 7 abnormalities in 5-mivron and 15-micron paraffin-embedded tissue sections from prostatic carcinoma. Histochem. Cell Biol. Feb. 1997, vol. 107, No. 2, pp. 121-126.
Tagawa Y. et al. Differences in spatial localization and chromatin pattern during different phases of cell cycle between normal and cancer cells. Cytometry, Apr. 1, 1997, vol. 27, No. 4, pp. 327-335.
Beil M. et al. Spatial distribution patterns of interphase centromeres during retinoic acid-induced differentiation of promyelocytic leukemia cells. Cytometry, Apr. 1, 2002, vol. 47, No. 4, pp. 217-225.
Beil M. et al. Statistical analysis of the three-dimensional structure of centromeric heterochromatin in interphase nuclei. J. Microsc. Jan. 2005, vol. 217, Pt. 1, pp. 60-68.
Garagna S. et al. Three-dimensional localization and dynamics of centromeres in mouse oocytes during folliculogenesis. J. Mol. Histol., Aug. 2004, vol. 35, No. 6, pp. 631-638.
Kuroda, M. et al. Alteration of chromosome positioning during adipocyte differentiation. J. Cell Sci., Nov. 15, 2004, vol. 117, Pt. 24, pp. 5897-5903.

Wiblin A. E. et al. Distinctive nuclear organisation of centromeres and regions involved in pluripotency in human embryonic stem cells. J. Cell Sci., Sep. 1, 2005, vol. 118, Pt. 17, pp. 3861-3868.
Toland C. F. et al. 3D organisation of chromosome 11 centromeres in prostate cancer cell lines. Cellular Oncology, vol. 27, No. 2, 2005, p. 158.
Koutna I. et al. Topography of genetic loci in tissue samples: towards new diagnostic tool using interphase FISH and high-resolution image analysis techniques. Analytical Cellular Pathology: The Journal of the European Society for Analytical Cellular Pathology, vol. 20, No. 4, 2000, pp. 173-185.
Solovei Irina et al. Differences in centromere positioning of cycling and postmitotic human cell types. Chromosoma vol. 112, No. 8, Jun. 2004, pp. 410-423.
Bayani Jane et al. Spectral karyotyping identifies recurrent complex rearrangements of chromosomes 8, 17 and 20 in osteosarcomas. Genes Chromosomes and Cancer, vol. 36, No. 1, Jan. 2003, pp. 7-16.
Beheshti et al. Identification of a high frequency of chromosomal rearrangements in the centromeric regions of prostate cancer cell lines by sequential Giemsa banding and spectral karyotyping. Molecular Diagnosis, vol. 5, No. 1, Jan. 1, 2000, pp. 23-32.
Sarkar Rahul et al. Alterations of centromere positions in nuclei of immortalized and malignant mouse lymphocytes. Cytometry, Part A: The Journal of the International Society for Analytical Cytology, Jun. 2007, vol. 71, No. 6, pp. 386-392.
Guffei Amanda et al. c-Myc-dependent formation of robersonian translocation chromosomes in mouse cells. Neoplasia, vol. 9, No. 7, Jul. 2007, p. 578.
Goncalves Dos Santos Silva Amanda et al. Centromeres in cell division, evolution, nuclear organization and disease. Journal of Cellular Biochemistry, Aug. 15, 2008, vol. 104, No. 6, pp. 2040-2058.
Knecht Hans et al. Three-dimensional Telomere Signatures of Hodgkin- and Reed-Sternberg Cells at Diagnosis Identify Patients with Poor Response to Conventional Chemotherapy. Translational Oncology, vol. 5, No. 4, Aug. 2012, pp. 269-277.
Klewes Ludger et al. Novel Automated Three-Dimensional Genome Scanning Based on the Nuclear Architecture of Telomeres. Cytometry Part A, 79A, pp. 159-166, 2011.
Gadji Macoura et al. Three-dimensional Nuclear Telomere Architecture is Associated with Differential Time to Progression and Overall Survival in Glioblastoma Patients. Neoplasia, vol. 12, No. 2, Feb. 2010, pp. 183-191.
Knecht H. et al. The 3D nuclear organization of telomeres marks the transition from Hodgkin to Reed-Sternberg cells. Leukemia, vol. 23, 2009, pp. 565-573.
Linares-Cruz Gustavo et al. p21WAF-1 reorganizes the nucleus in tumor suppression. Proc. Natl. Acad. Sci. USA, vol. 95, pp. 1131-1135, Feb. 1998.
Kozubek, M. et al. Combined confocal and wide-field high-resolution cytometry of fluorescent in situ hybridization-stained cells. Cytometry, vol. 45, pp. 1-12, 2001.
Gehrke, I. et al. Three dimensional (3D) analysis of centromere organization in interphase nuclei of normal and tumor cells. AACR Meeting Abstracts 2005, 30.
Kozubek, M. et al. Automated acquisition and processing of multidimensional image data in confocal in vivo microscopy. Microscopy Research and Technique, vol. 64, pp. 164-175, 2004.
Louis S. F. et al. c-Myc induces chromosomal rearrangements through telomere and chromosome remodeling in the interphase nucleus. Proc,. Natl. Acad. Sci USA, vol. 102, No. 27, pp. 9613-9618, 2005.
Vermolen B. J. et al. Characterizing the Three dimensional Organization of Telomeres. Cytometry A. 67A:144-50, 2005.
Mai Sabine et al. Oncogenic Remodeling of the Three-Dimensional Organization of the Interphase Nucleus. Cell Cycle, 2005, vol. 4, No. 10, pp. 1327-1331.
Mai Sabine et al. The Significance of Telomeric Aggregates in the Interphase Nuclei of Tumor Cells. Journal of Cellular Biochemistry, vol. 97, pp. 904-915, 2006.

(56) References Cited

OTHER PUBLICATIONS

Olujohungbe Ade B. et al. 3D Telomeric Profiles of MGUS, MMN and Relapsed MM. Abstract presented at the 53rd ASH Annual Meeting and Exposition on Dec. 11, 2011.
Knecht Hans et al. 3D Telomere Dynamics in Hodgkins's Lymphoma. Abstract presented at the 52nd ASH Annual Meeting and Exposition on Dec. 6, 2010.
Mai, Sabine et al. 3D nuclear telomeric organization in CTCs isolated by filtration methods. Slides presented at the CTC Workshop on Apr. 28, 2011 in Toronto.

* cited by examiner

Relative Fluorescence Intensity

HEMATOLOGICAL DISORDER DIAGNOSIS BY 3D Q-FISH

CROSS-REFERENCE TO RELATED APPLICATIONS

This application claims benefit under 35 U.S.C. 119(e) to U.S. provisional application No. 61/566,348, filed Dec. 2, 2011, incorporated herein by reference in its entirety. This application also claims benefit to Canadian patent application no. 2,760,873, filed Dec. 2, 2011, incorporated herein by reference in its entirety.

FIELD

The present application relates to methods and systems for hematological cancer and disorder detection and treatment based on the nuclear organization and signatures of telomeres.

INTRODUCTION

The Three-Dimensional (3D) Nuclear Organization of Telomeres.

Telomeres are the ends of chromosomes. Functional telomeres prevent chromosomal fusions due to the presence of a protein complex, termed shelterin (de Lange, 2005). If any of the shelterin proteins are down-regulated or absent from the telomere, the complex is no longer protective, and affected telomeres become 'reactive' with other telomeres, and thus gain the ability to perform illegitimate fusion and/or recombination. Such telomeres become 'dysfunctional'.

Telomere dysfunction is typical of cancer cells. When speaking of telomere dysfunction, one refers to critically shortened telomeres and/or to telomeres that lost their protective protein cap irrespective of their actual length ("uncapped" telomeres). When telomeres become dysfunctional, cells can become senescent, enter crisis or begin breakage-bridge-fusion cycles that initiate ongoing genomic instability (Misri et al., 2008; Deng et al, 2008: Lansdorp, 2009). Many cancer cells display chromosomal aberrations that are the direct result of telomere dysfunction. Examples include osteosarcoma (Selvarajah et al., 2006), prostate cancer (Vukovic et al., 2007; Vukovic et al., 2003), breast cancer (Meeker et al., 2004), and colon cancer (Stewenius et al., 2005; for reviews see, DePinho and Polyak, 2004; Lansdorp, 2009; Murnane and Sabatier, 2004).

Impact of Nuclear Telomere Architecture in the Transition in Hematological Disorders Myelodysplastic syndromes (MDS) are composed by a heterogeneous group of clonal disorders of hematopoietic progenitors displaying genomic instability[1]. Further, many cases of MDS are characterized by progression to acute myeloid leukemia (AML/MDS), by accumulation of genetic abnormalities and blockage of cell differentiation and accumulation of blast cells. However, pathology of MDS and AML/MDS are cytologically distinguishable since both cells show very different morphologies such as dysplastic features. Few studies have addressed the impact of telomeres in MDS and AML/MDS[2]. Telomeres are the ends of chromosomes capped by a protective protein complex, termed shelterin[3]. Proper telomere capping preserves chromosomal integrity and prevents terminal end-to-end fusions, which results in breakage-bridge-fusion cycles. Telomeres contribute to chromosome positioning within the nucleus[4]. The 3D nuclear organization of telomeres allows for a distinction between normal and tumour cells: nuclei of the latter tend to be disorganized, and commonly contain telomeric aggregates[5]. Alterations in telomere architecture and telomeric dysfunction are associated with the onset of genomic instability[6-8]. Previous work has shown altered 3D telomeric organization in plasmacytoma[6,9], cervical cancer[8,10], Burkitt's lymphoma[5], and head and neck cancer[5]. Further, a mechanistic understanding for the transition of mononuclear Hodgkin cells to multinuclear Reed-Sternberg cells has been demonstrated[11]. Further GBM patients can be stratified into 3 distinct and highly predictive prognostic classes, and nuclear telomere architecture has been proposed as a novel and highly efficient biomarker of GBM[12]. However, despite several studies demonstrating the role of telomeres disruption in the occurrence of hematopoietic malignancies, little is know about the evolution of MDS to AML/MDS[13]. Few data of average telomeres length and telomere length at chromosomal level are available in MDS and AML[14].

Multiple myeloma (MM) is recognized as the second most common cancer of the blood, affecting adults past the age of 50. Although risk factors have been established, it is currently not possible to assess the individual risk to cancer progression. Moreover, the causes of disease progression from its precursor condition, monoclonal gammopathy of undetermined significance (MGUS), to full-blown MM and its progression to relapsed MM remain elusive.

In RS-cells the telomere protecting shelterin complex appears to be disrupted and deregulation of DNA repair mechanisms is observed. These changes occur in both, classical EBV negative and EBV-associated, LMP1 expressing HL (Lab Invest. 2010; 90:611-619). However, it is not known whether the 3D telomere profile at diagnostic biopsy is different in patients entering rapid remission after initiation of standard chemotherapy Adriamycin, Bleomycin, Vinblastine, Dacarbazine (ABVD) compared to that of patients with relapsing or refractory disease.

SUMMARY OF THE DISCLOSURE

Disclosed herein are methods and systems for hematological cancer and disorder detection and treatment based on the nuclear organization and signatures of telomeres. The methods allow for; 1) for the distinction of normal and tumor cells (Klewes et al., 2011), 2) for the identification of patient subgroups (Gadji et al., 2010) that will allow for new treatment design, 3) for the identification of patients who will recur and therefore should obtain different treatments (Knecht et al., 2010), 4) for treatment monitoring, and 5) for personalized medical management of patients (not one treatment for all, but a treatment specifically adapted to each patient).

The methods have been tested in a number of hematological cancers and disorders including multiple myeloma, Hodgkin's lymphoma, plasmacytoma, myelodysplastic syndrome, acute myeloid leukemia, chronic myeloid leukemia.

Accordingly, disclosed herein are methods relating to the use of 3D telomeric analysis on diagnostic samples to provide prognosis information in different hematological cancers. Specific 3D telomeric signatures distinguish between MGUS, MM and relapsed MM and between refractory or relapsing Hodgkin's lymphoma and rapid remission Hodgkin's lymphoma.

In particular, the present disclosure provides a method for evaluating hematological disorder cells derived from a subject comprising the steps of:
a) obtaining a subject hematological cancer cell test sample;
b) assaying the cell sample to obtain a 3D telomeres organization test sample signature using 3D q-FISH, the 3D telomeres organization signature comprising at least one feature selected from telomeres per nuclear volume, telomere number, mean telomere intensity, telomere size, presence and/or number of telomeric aggregates, distances from nuclear centre and a/c ratio;
c) comparing the test sample signature to one or more control reference signatures, wherein each reference signature defines for one or more of the features a 3D telomeres organization signature associated with a hematological disorder clinical outcome and/or subtype; and
d) identifying differences or similarities between the test sample signature and the one or more control reference signatures;
wherein the 3D telomeres organization signature of the test sample cell is indicative of the clinical outcome of the subject and/or the hematological disorder subtype.

In one embodiment, the clinical outcome is responsiveness to standard chemotherapy. In another embodiment, the clinical outcome is progression and/or recurrence of the cancer.

In one embodiment, comparing the test sample signature to one or more control reference signatures and identifying differences or similarities between the test sample signature and the one or more control reference signatures comprises:
a) providing one or more reference 3D telomeres organization signatures associated with a clinical outcome and/or disorder subtype; and
b) identifying the reference 3D telomeres organization signature most similar to the test sample cell 3D telomeres organization signature.

In one embodiment, the hematological disorder is multiple myeloma (MM).

In another embodiment, the method comprises:
a) determining a 3D telomeres organization signature of a test sample cell from the subject;
b) comparing the 3D telomeres organization signature of the test sample cell with a reference 3D telomeres organization signature comprising;
  1) providing one or more reference 3D telomeres organization signatures selected from a monoclonal gammopathy of undetermined significance (MGUS) telomeres organization reference signature, a MM telomeres organization reference signature and a relapsed MM telomeres organization reference signature; and
  2) identifying the reference 3D telomeres organization signature most similar to the test sample cell 3D telomeres organization signature;
  wherein a difference or similarity between the test sample cell 3D telomeres organization signature and the reference 3D telomeres organization signature is indicative of the clinical outcome or disorder subtype of the subject.

In a further embodiment, the method comprises:
a) determining a 3D telomeres organization signature of a test sample cell from the subject, wherein the subject has MGUS;
b) comparing the 3D telomeres organization signature of the test sample cell with a reference 3D telomeres organization signature, wherein the signature comprises one or more of telomere numbers and number of aggregates;
wherein an increased number of telomere numbers in the test sample cell 3D telomeres organization signature compared to the reference 3D telomeres organization signature is indicative of an increased likelihood of progression to MM.

In another embodiment, the method comprises:
a) determining a 3D telomeres organization signature of a test sample cell from the subject, wherein the subject has MM;
b) comparing the 3D telomeres organization signature of the test sample cell with a reference 3D telomeres organization signature, wherein the signature comprises one or more of telomere numbers and number of aggregates;
wherein a decreased number of telomere numbers and/or an increased number of telomere aggregates in the test sample cell 3D telomeres organization signature compared to the reference 3D telomeres organization signature is indicative of an increased likelihood of MM recurrence.

Optionally, the reference 3D telomeres organization signature comprises a 3D telomeres organization signature of a sample from a subject with MGUS or non-relapsing MM.

In another embodiment, the hematological disorder is Hodgkin's lymphoma. Optionally, the subject with Hodgkin's lymphoma has initiated chemotherapy, for example Adriamycin, Bleomycin, Vinblastine, Dacarbazine (ABVD).

In one embodiment, the test sample is a diagnostic biopsy.

In a further embodiment, the method comprises:
a) determining a 3D telomeres organization signature of a test sample cell from the subject;
b) comparing the 3D telomeres organization signature of the test sample cell with a reference 3D telomeres organization signature comprising;
c) providing one or more reference 3D telomeres organization signatures selected from a rapid remission Hodgkin's lymphoma telomeres organization reference signature, and a relapsing or refractory Hodgkin's lymphoma telomeres organization reference signature; and
d) identifying the reference 3D telomeres organization signature most similar to the test sample cell 3D telomeres organization signature;
wherein a difference or similarity between the test sample cell 3D telomeres organization signature and the reference 3D telomeres organization signature is indicative of the clinical outcome or disorder subtype of the subject.

In another embodiment, the method comprises:
a) determining a 3D telomeres organization signature of a test sample cell from the subject, wherein the subject has Hodgkin's lymphoma and has initiated chemotherapy;
b) comparing the 3D telomeres organization signature of the test sample cell with a reference 3D telomeres organization signature comprising;
  1) providing one or more reference 3D telomeres organization signatures selected from a rapid remission Hodgkin's lymphoma telomeres organization reference signature, and a relapsing or refractory Hodgkin's lymphoma telomeres organization reference signature; and 2) identifying the reference 3D telomeres organization signature most similar to the test sample cell 3D telomeres organization signature;

wherein a similarity between the test sample cell 3D telomeres organization signature and the relapsing or refractory Hodgkin's lymphoma 3D telomeres organization reference signature is indicative the subject has an increased risk of Hodgkin's lymphoma recurrence and/or refractory disease.

In one embodiment, an increased number of very small telomeres, including for example "t-stump" telomeres, in the test sample cell 3D telomeres organization signature compared to the reference 3D telomeres organization signature is indicative of Hodgkin's relapse or refractory disease.

In another embodiment, an increased number of telomeres with a relative fluorescent intensity of less than 5000 or 2500 units, optionally less than 4000, 3000, 2000, 1000 or 500 units in the test sample cell 3D telomeres organization signature compared to the reference 3D telomeres organization signature is indicative of Hodgkin's relapse or refractory disease.

In another embodiment, the method comprises:
a) determining a 3D telomeres organization signature of a test sample cell from the subject, wherein the subject has Hodgkin's lymphoma and has initiated chemotherapy;
b) comparing the 3D telomeres organization signature of the test sample cell with a reference 3D telomeres organization signature;
wherein an increased number of very small telomeres, including for example "t-stump" telomeres, in the test sample cell 3D telomeres organization signature compared to the reference 3D telomeres organization signature is indicative of an increased risk of Hodgkin's relapse or refractory disease.

In a further embodiment, a decreased number of very short telomeres including "t-stumps" in the test sample cell 3D telomeres organization signature compared to the reference 3D telomeres organization signature is indicative of treatable Hodgkin's lymphoma and/or an increased likelihood of disease free survival.

In an embodiment, the reference 3D telomeres organization signature and/or relapsing or refractory Hodgkin's lymphoma telomeres organization reference signature comprises RS cells that contain at least 45%, at least 50%, at least 55%, at least 60% at least 65%, at least 70%, at least 75%, at least 80% or at least 85% very small telomeres, including for example "t-stump" telomeres.

In another embodiment, the reference 3D telomeres organization signature and/or relapsing or refractory Hodgkin's lymphoma telomeres organization reference signature comprises H cells that contain at least 35%, at least 40%, at least 45%, at least 50%, at least 55%, at least 60% at least 65%, at least 70% or at least 75% very small telomeres, including for example "t-stump" telomeres.

In a further embodiment, an increased number of telomere aggregates in the test sample cell 3D telomeres organization signature compared to the reference 3D telomeres organization signature is indicative of Hodgkin's relapse or refractory disease.

In one embodiment, the method comprises:
a) determining a 3D telomeres organization signature of a test sample cell from the subject, wherein the subject has Hodgkin's lymphoma and has initiated chemotherapy;
b) comparing the 3D telomeres organization signature of the test sample cell with a reference 3D telomeres organization signature;
wherein an increased number of telomere aggregates in the test sample cell 3D telomeres organization signature compared to the reference 3D telomeres organization signature is indicative of an increased risk of Hodgkin's relapse or refractory disease.

Optionally, a decreased number of telomere aggregates in the test sample cell 3D telomeres organization signature compared to the reference 3D telomeres organization signature is indicative of treatable Hodgkin's lymphoma and/or an increased likelihood of disease free survival.

In one embodiment, the reference 3D telomeres organization signature and/or relapsing or refractory Hodgkin's lymphoma telomeres reference organization signature comprises H cells that contain at least about 1, at least about 1.5, at least about 2, at least about 2.5, at least about 3, at least about 3.5, or at least about 4, aggregates per cell.

In another embodiment, the reference 3D telomeres organization signature and/or relapsing or refractory Hodgkin's lymphoma telomeres organization reference signature comprises RS cells that contain at least about 3, at least about 3.5, at least about 4, at least about 4.5, at least about 5, at least about 5.5, or at least about 6, aggregates per cell.

Optionally, the 3D telomeres organization signature, for example the test sample 3D telomeres organization signature or the reference 3D telomeres organization signature, is obtained from a tissue section, optionally from a tissue section having a thickness of about 5 microns to about 15 microns, for example about 5 microns.

The present application also discloses that in patients with refractory or relapsing Hodgkin's lymphoma, mononuclear H cells have 3D nuclear telomere signatures that are similar to RS cells, in particular RS cells from patients in remission.

Therefore, in another embodiment, one or both of a RS cell nuclei 3D telomeres organization signature and an H cell nuclei 3D telomeres organization signature is obtained from the test sample and compared to one or more RS cell nuclei 3D telomeres organization reference signature and H cell nuclei 3D telomeres organization reference signature each associated with a clinical outcome.

In a further embodiment, the test sample H cell nuclei 3D telomeres organization signature is compared to one or more the reference signatures, and an H cell nuclei 3D telomeres organization signature that is similar to a RS cell nuclei 3D telomeres organization reference signature is indicative the subject is likely to have refractory Hodgkin's lymphoma and/or to relapse.

In one embodiment, the 3D nuclear telomeric organization signature of a H cell nucleus that is similar to a remission RS cell nucleus 3D telomeric organization signature is indicative that the subject is likely to have refractory Hodgkin's lymphoma and/or to relapse.

In another embodiment, a similar number of telomere aggregates and/or very small telomeres, including for example "t-stump" telomeres, in the RS cell nucleus 3D telomeres organization signature compared to the H cell nucleus 3D telomeres organization signature is indicative that the subject is likely to have refractory Hodgkin's lymphoma and/or to relapse.

The present application also discloses that in patients with progressing or relapsing Hodgkin's lymphoma, compared with mononuclear H-cell-nuclei, RS-cell nuclei have a significantly increased total telomere mass as measured by segmental telomere intensity.

Thus, in another embodiment, an increased total telomere mass (e.g. segmental telomere intensity) in RS cell nuclei compared to H cell nuclei in the test sample is indicative of relapsing or refractory Hodgkin's lymphoma.

Further, in Hodgkin's patients entering rapid remission, the total telomere mass in RS cell nuclei and H cell nuclei remains nearly unchanged.

Accordingly, in another embodiment, comparable total telomere mass in RS cell nuclei and H cell nuclei in the test sample is indicative the subject is likely to respond to therapy and/or enter remission.

The present disclosure also relates to a method of treating a subject with a hematological disorder such as MM or Hodgkin's lymphoma comprising:
 a) obtaining a test sample from the subject;
 b) assaying the test sample according to any of the method described within; and
 c) administering to the subject a treatment suitable for the predicted clinical outcome or cancer subtype.

The present methods also include automated methods which for example permit an increased speed of the scan. For example, approximately 10,000-15,000 cells/hour can be scanned by 3D (see for example method described in Example 8). Further the methods have applicability in scenarios where there are very low numbers of tumor cells in the blood or tissue.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

An embodiment of the disclosure will now be described in relation to the drawings in which.

Death occurred 9 months after this biopsy (20c) from refractory disease. (A) Upper panel: The telomere signals (crosses) are marked in three axes (x, y, z). Lower panel: The RS cell contains a total of 74 mainly very small telomere and 6 aggregates (above the darker line), and the mean telomere intensity is at 3864 units and the segmental telomere intensity (total telomere mass) is at 347,732 units. (B) Upper panel: Qualitative assessment reveals no differences to the telomere frequency observed in A. However, alignment according to intensity (lower panel) shows 90 mostly very small telomere and 8 aggregates. Most importantly, the mean telomere intensity lowered to 2478 units and the segmental telomere intensity (total telomere mass) to 247, 780 units, demonstrating ongoing telomere shortening and loss.

Figure 10A:
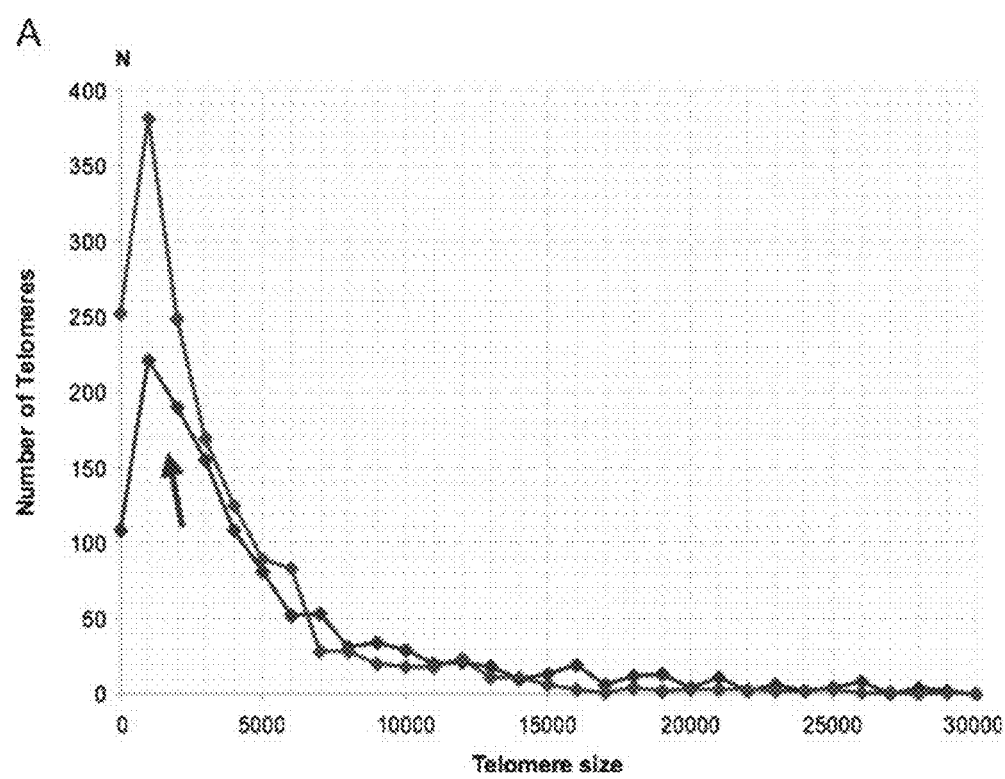
Figure 10B:
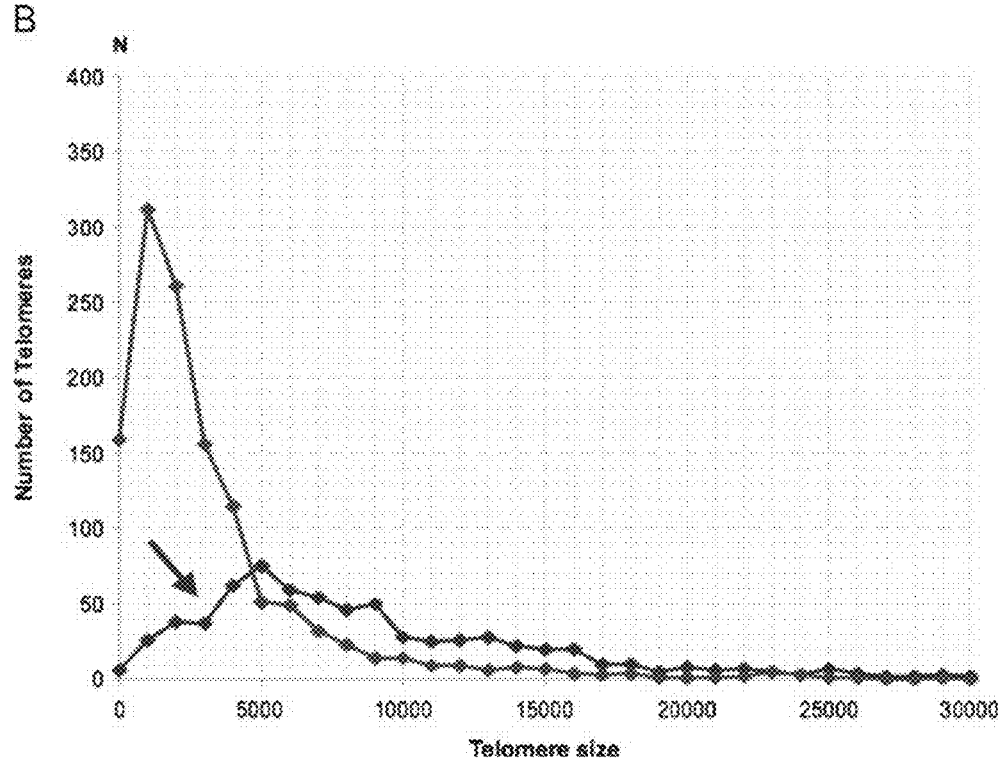

FIG. 10. Typical telomere profiles associated with refractory disease (A) and rapid remission (B). Telomere distribution according to size in mononuclear H (line indicated with arrow) and at least binuclear RS cells (second line). Results are based on three-dimensional analysis of at least 30 H and 30 RS cells in each biopsy. Frequency (y axis) and relative fluorescent intensity, that is, the size of telomeres (x axis) in a diagnostic 5-μm lymph node section. (A) Female patient, 77 years old, nodular sclerosis subtype, LMP1-expressing stage IIIB, IPS 4, refractory disease, death after 11 months (case 17). In both, H and RS cells, there is a highly significant shift (P<0.01) from midsized and small telomeres to very small telomeres including "t-stumps" of 0 to 5000 relative fluorescence units. Importantly, already the mononuclear H cells exhibit a three-dimensional telomere profile usually identified only in RS cells (arrow). (B) Male patient, 71 years old, mixed cellularity subtype, LMP1-expressing stage IIIB, IPS 4, in remission for 62 months, documented after 4×ABVD (case 12). In RS cells, the highly significant shift to very small telomeres is still observed, whereas it is completely absent in H cells (arrow). Thus, H cells in aggressive disease do, contrary to H cells in cases entering persistent remission, already contain multiple very small telomeres consistent with having passed multiple rounds of mitosis without ending up in multinuclear end-stage RS cells. Notably, this is observed in cases with nearly identical clinical presentation.

Figure 11:
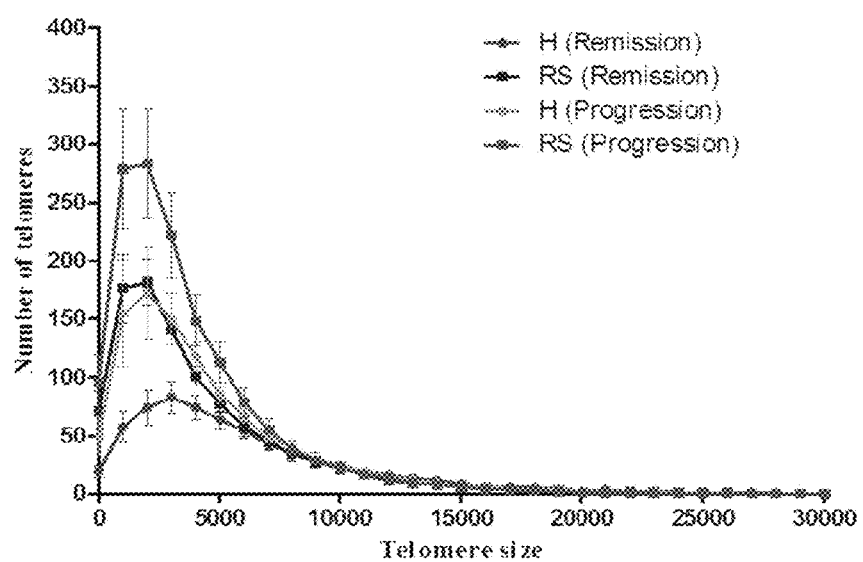

FIG. 11. Telomere distribution according to size in H and RS cells in rapid remission and relapsing/refractory HL. The mean telomere distributions (±SEM) in H and RS cells of 16 patient biopsies associated with rapid remission (group A) and 16 biopsies (8 initial biopsies, 4 relapses, and 4 progressions) from 10 patients (group B) are shown. Results are based on three-dimensional analysis of at least 30 H and 30 RS cells in a diagnostic 5-μm-thin lymph node section of each biopsy. Frequency (y axis) and relative fluorescent intensity, that is, the size of telomeres (x axis) are shown. There is a highly significant shift (P<0.01) from small telomere (>5000 relative fluorescence units) to very small telomere including "t-stumps" of 0 to 5000 relative fluorescence units in all four curves. However, mononuclear H cells of aggressive disease have nearly as much very small telomere (P=0.374) as RS cells of cases entering rapid and lasting remission indicating multiple rounds of mitotic division without progression to end-stage RS cells.

Figure 12:
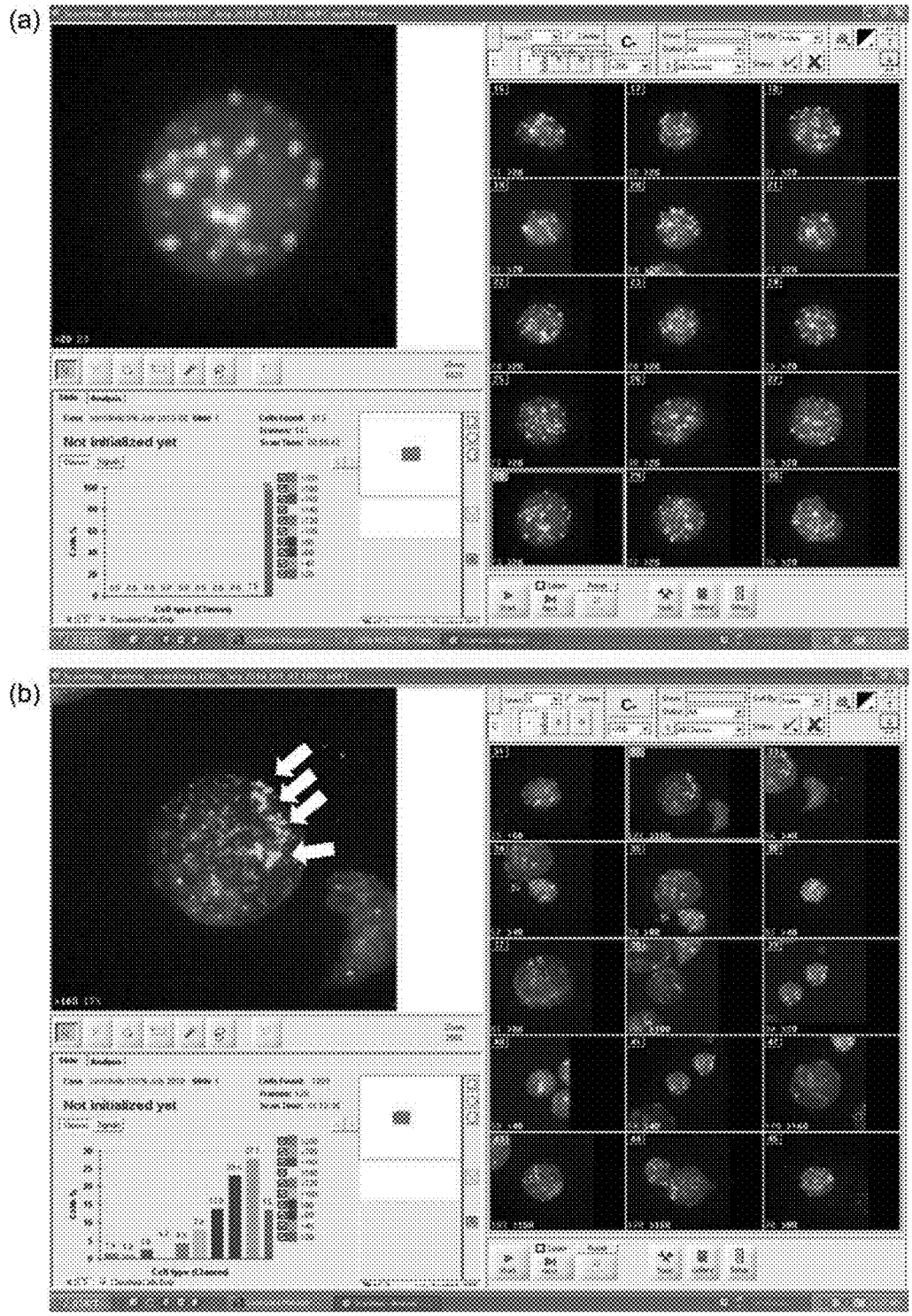

FIG. 12. User-interphase of ScanView displaying acquired cells in the gallery (right half)) with the cell ID in the upper left hand corner, number of detected signals and allocated class in the lower left hand corner, a single cell selected from the gallery (upper left hand corner), and the number of cell classified to each class based on the number of telomeres per cell. The distribution of all scanned is displayed in the lower left hand corner in form of a histogram. To the left of the histogram the scanned area is shown as well as the number of cells detected, the number of frames taken, as well as the scan time. Normal cells (a) and tumor cell [MOPC] (b) differ in cell size, the presence of aggregates (arrows), and the classification of cells based on the number of detected telomere signals. Three independent experiments were performed.

Figure 13:
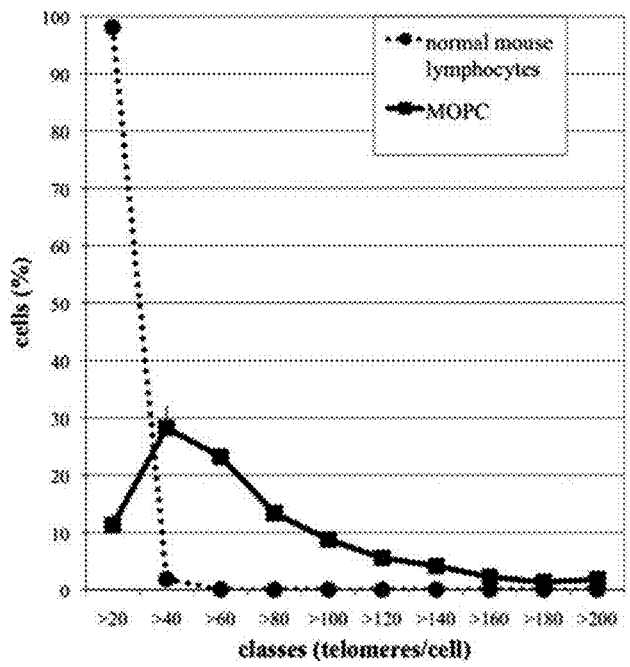

FIG. 13. Analysis of the signal numbers in the nuclei of normal mouse lymphocytes (circles) and mouse plasmacytoma cells (squares). Cells were fixed and hybridized with Cy3-labeled PNA probes. The distribution of cells in classes shows a signature differing between normal- and MOPC cells. The average of three independent scans for each cell type is shown (error bars indicate ±S.D.). The error bars are small due to standard deviations ranging mostly between 0 and 1 and cannot be further highlighted in this figure.

Figure 14:
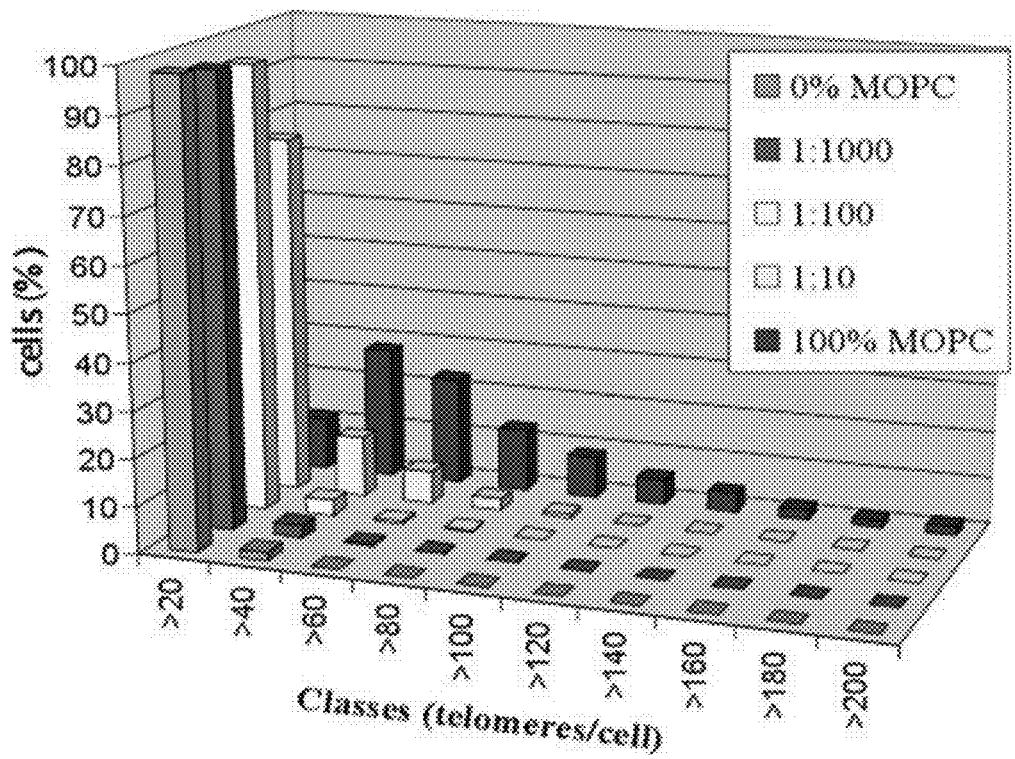

FIG. 14. Detection of mouse plasmacytoma cells (MOPC) within a population of normal mouse lymphocytes: Normal mouse lymphocytes were replaced by MOPC cells, and hybridized with Cy3-labelled PNA probes. The slides were scanned using a Cy3-filter (telomere signals), and a DAPI filter for the counterstained nuclei. The presence of tumor cells causes a shift of cells with >20 signals/cell to classes with higher number of telomere signals. Each experiment was performed in independent triplicates using three different mouse cell preparations.

Figure 15:
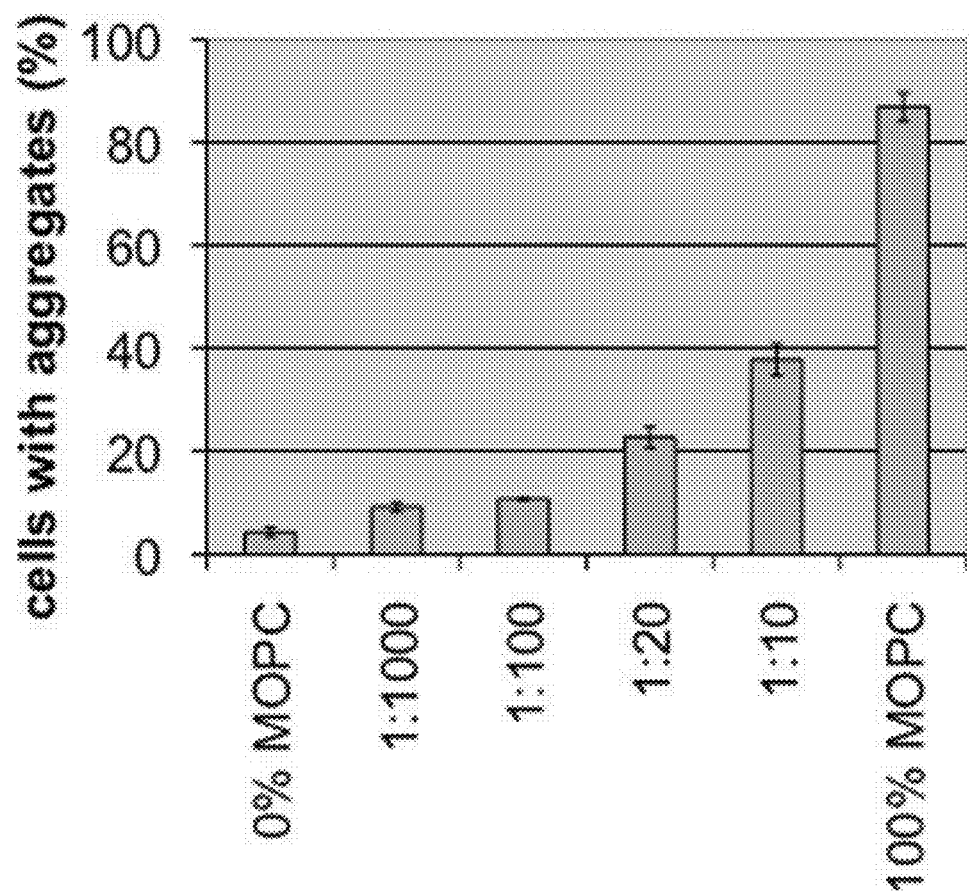
Figure 16:
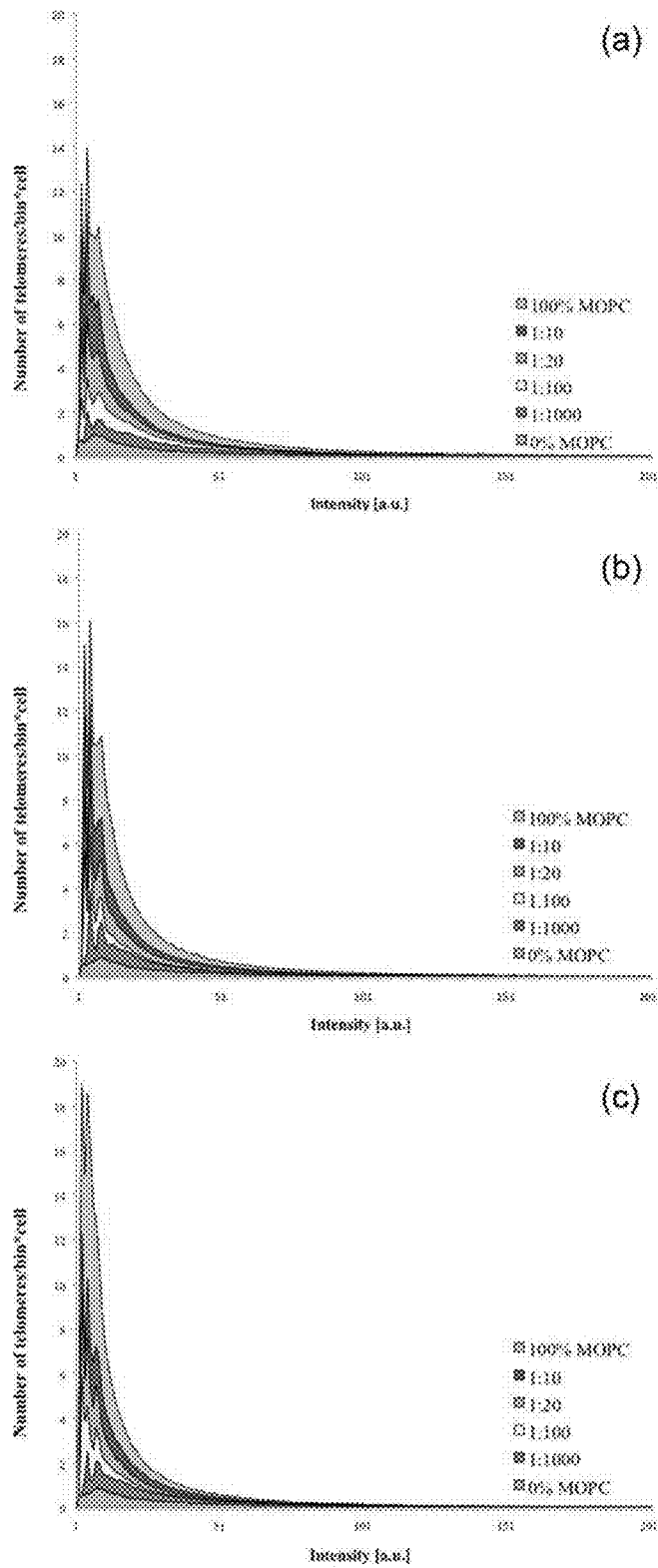

FIG. 15. Aggregate detection in a mixed population of normal mouse lymphocytes and MOPC. Normal mouse lymphocytes were spiked with MOPC cells, and hybridized as described. The cells were analyzed for the presence of telomere aggregates using TeloScan, a modified version of TeloView. The average from three independent scans for each independent experiment is shown (error bars indicate ±S.D.). The statistical significance of the difference between normal cells and the samples with 0.1% MOPC was P<0.001. All measurements were done with three independently prepared mouse lymphocyte preparations and the respective dilutions. [Color figure can be viewed in the online issue, which is available at wileyonlinelibrary.com hereby incorporated by reference FIG. 16. a-c. Signal intensity in a mixed population of normal mouse lymphocytes and MOPC. Various concentrations of MOPC within normal mouse lymphocytes were analyzed for the signal intensity, starting with 100% normal cells, 1 tumor cell/1,000 normal cells, 1/100, 1/20, 1/10 and 100% MOPC. The peaks increase with increasing number of tumor cells present in the test mixtures. This change is reproducible comparing the graphs of three independent experiments.

DETAILED DESCRIPTION

I. Definitions

The term "a/c ratio" refers to a parameter that defines the nuclear position of a telomere. The a/c ratio is characteristic for a specific cell cycle phase (Vermolen et al., 2005). The volume occupied by telomeres can be conveniently described as an ellipsoid having two axes of equal length[34]. As such, it is simpler to describe the spheroid degree of variation from a perfect sphere by the ratio a/c where a=b are the similar semi-axes and c is the third one. Such a description reflects the degree to which the telomere volume is oblate. As an example, a perfect sphere will have a/c=1 ratio while an oblate volume will have a ratio of a/c>1. The x'y' plane of the spheroid should not necessarily be parallel to the microscope slide plane (described by xy), especially in those cases where tissue section are analyzed.

The term "cancer" as used herein means a metastatic and/or a non-metastatic cancer, and includes primary and secondary cancers. Reference to cancer includes reference to cancer cells.

As used herein, the term "cell" includes more than one cell or a plurality of cells or portions of cells. The sample may be from any animal, in particular from humans, and may be biological fluids (such as blood, serum, or bone marrow), tissue, or organ. The term "test cell" is a cell that is suspected of having a hematopoietic cancer and/or precursor syndrome. In such an embodiment, the test cell includes, but is not limited to, a hematopoietic cancer cell or a cancer precursor cell. The term "control cell" is a suitable comparator cell e.g. a cell that is known of not having a hematopoietic cancer (e.g. negative control) or that is known as having a hematopoietic cancer or precursor syndrome (e.g. positive control).

The term "control" as used herein refers to a suitable comparator subject, sample, cell or cells such as non-cancerous subject (or earlier stage cancer subject, sample, cell or cells), or blood sample, cell or cells from such a subject, for comparison to a cancer subject, sample (e.g. test sample) cell or cells from a cancer subject; or an untreated subject, cell or cells, for comparison to a treated subject, cell or cells, according to the context. Control can also refer to a value or reference signature representative of a control subject, cell and/or cells and/or a population of subjects.

The term "hematological disorder" as used herein means any hematological cancer or demagogical precancer syndrome.

The term "hematological cancer" as used herein refers to cancers of blood and bone marrow, such as leukemia, multiple myeloma and lymphoma and includes primary and secondary cancers. Reference to hematological cancer includes reference to hematological cancer cells.

The term "leukemia" as used herein means any disease involving the progressive proliferation of abnormal leukocytes found in hematopoietic tissues, other organs and usually in the blood in increased numbers. Leukemia includes, but is not limited to, acute myeloid leukemia (AML), acute lymphocytic leukemia (ALL), chronic lymphocytic leukemia (CLL) and chronic myelogenous leukemia (CML).

The term "lymphoma" as used herein means any disease involving the progressive proliferation of abnormal lymphoid cells. For example, lymphoma includes mantle cell lymphoma, Non-Hodgkin's lymphoma, and Hodgkin's lymphoma.

The term "myelodysplastic syndrome" or "MDS" as used herein includes clonal disorders of the hematopoietic stem cells mainly in the elderly, which evolves either into bone marrow aplasia or acute myeloid leukemia. If the number of bone marrow blasts is between 5 and 20% it is referred to as refractory anemia with excess of blasts, if it is higher than 20%, then the transformation into acute leukemia has occurred. A normal patient moves for example to a MDS preleukemic state by increasing the number of telomeres and has few telomeric aggregates, and to AML by increasing the genomic instability and the telomeric aggregate numbers.

The term "monoclonal gammopathy of undetermined significance" or MGUS is a precursor to multiple myeloma (MM) and is defined according to the International Myeloma Working Group (IMWG, 2010; Kyle et al., 2010) as a disease having i) serum monoclonal protein under 3 g/dL, ii) clonal bone marrow plasma cells under 10%, and iii) no end-organ lesions (including hypercalcemia, renal insufficiency, anemia, and bone lesions) (Landgren, 2010).

MGUS fall in two distinct biological entities, lymphoid MGUS, that can progress to Waldenström's macroglobulinemia, lymphoma, or other lymphoproliferative disorders (Kyle et al, 2003), and plasma-cell MGUS that can progress to MM (Landgren 2010, Mailankody et al, 2010). The present focus is on the latter type of MGUS.

The term "MGUS telomere organization signature" as used herein refers to a 3D telomere organization that measured for example using TeloView or TeloScan. It includes for example, the following criteria; telomere numbers, telomere intensities (sizes), overall telomere distribution, telomere aggregates, nuclear volumes.

The term "multiple myeloma", "MM" or "myeloma" as used herein means a tumor or cancer composed of cells derived from the hematopoietic tissues of the bone marrow. Multiple myeloma is also known as plasma cell myeloma and is defined by serum M-protein levels (e.g. >3 g/dL), bone marrow plasma cells (e.g. >10%), and end organ damage (e.g. lytic bone lesions, anemia, hypercalcemia, renal failure) (Mailankody et al., 2010). Multiple myeloma is an incurable disease and affects adults past the age of 50 (3%) and increases with age (5% in >70 years of age). MM is the second most prevalent hematological cancer. The 5-year survival rate for MM in the USA is 38.2% (1999-2006, Statistics of the American Cancer Society). In 2010, according to the National Cancer Institute (NCI), 20,110 new MM cases were diagnosed, and 10,650 deaths related to MM for the United States.

The term "MM telomere signature" as used herein is a 3D signature with elevated telomere numbers per nuclear volume, low fluorescent intensity of telomeres, telomeric aggregates, altered a/c ratios. All this is in comparison to MGUS and relapsed MM. For example, MM has higher telomere numbers than MGUS; MGUS has higher telomere numbers than relapsed MM. MM has more aggregates than MGUS. Relapsed MM has the highest level of aggregates.

The term "prognosis" as used herein refers to an expected course of clinical disease. The prognosis provides an indication of disease progression and includes for example, an indication of likelihood of recurrence, metastasis, death due to disease, tumor subtype or tumor type. The prognosis can comprise a good prognosis which corresponds to a good clinical outcome relative to the spectrum of possible clinical outcomes for the specific cancer or syndrome, and a poor prognosis, which corresponds to a poor clinical outcome relative to the spectrum of possible clinical outcomes for the specific cancer or syndrome. As used herein, "good prognosis" means a probable course of disease or disease outcome that has reduced morbidity and/or reduced mortality compared to the average for the disease or condition. As used herein, "poor prognosis" means a probable course of disease or disease outcome that has increased morbidity and/or increased mortality compared to the average for the disease or condition.

The term "telomeres organization signature" as used herein refers to a specific telomeric signature that classifies the cell for example as normal or aberrant; rapid-remission or refractory; MGUS or MM; or MDS or AML. The criteria that define the differences include 1) nuclear telomere distribution, 2) the presence/absence of telomere aggregate(s) (Telomere aggregates are telomeres found in clusters that at an optical resolution limit of 200 nm cannot be further resolved and which are not seen in normal cells), 3) telomere numbers per cell, and 4) telomere sizes. Additional criteria include a/c ratios (a/c ratios define the nuclear positions of telomeres. The a/c ratios are characteristic for specific cell cycle phases and nuclear volumes.

The term "test sample cell telomeres organization signature" as used herein refers to a telomeric signature obtained from a test sample cell, for example a cell that is suspected of having a hematopoietic cancer and/or precursor syndrome.

The term "reference telomeres organization signature" as used herein refers to a telomeric signature obtained from a control or reference sample cell. For example, a reference telomeres organization signature is optionally obtained from a cell that is known of not having a hematopoietic cancer (e.g. negative control) or that is known as having a hematopoietic cancer or precursor syndrome (e.g. positive control).

The term "rapid remission Hodgkin's lymphoma telomeres organization signature" as used herein refers to patients with a significant increase of very short telomeres and telomere aggregates when compared to the mononuclear precursor H-cells. For example, telomeres with a relative fluorescent intensity (x-axis) ranging from 0-5,000 units are classified as very short, with an intensity ranging from 5,000-15,000 units as short, with an intensity from 15,000-30,000 units as mid-sized, and with an intensity >30,000 units as large (18). The rapid remission Hodgkin's lymphoma telomeres organization signature is characterized for example by a segmental telomere number (per 5 micron slice at 630× magnification) in RS cells of less than about 30, less than about 25, less than about 20 and/or in H cells of less than 20, less than 15, less than 13 or less than 10. The rapid remission Hodgkin's lymphoma telomeres organization signature is characterized for example by an increased mean telomere intensity in RS and H cells compared to the relapsing or refractory Hodgkin's lymphoma telomeres organization signature. The rapid remission Hodgkin's lymphoma telomeres organization signature is also characterized for example by a decreased percentage of very short telomeres in both RS and H cells compared to the relapsing or refractory Hodgkin's lymphoma telomeres organization signature. For example, rapid remission Hodgkin's lymphoma telomeres organization signature is characterized by having less than 70%, less than 65%, less than 60% very short telomeres in RS cells and less than 60%, less than 55%, less than 50% very short telomeres in H cells. The segmental telomere aggregates (per 5 micron slice at 630× magnification) is also less, for example less than 4, less than 3.5, or less than 3 in RS cells and less than 2.5, less than 2 or less than 1.5 in H cells. As indicated in the Table below, the differences between these parameters in the rapid remission and the relapsing or refractory Hodgkin's lymphoma telomeres organization signature are significant.

The term "relapsing or refractory Hodgkin's lymphoma telomeres organization signature" as used herein refers to patients showed significant increase of very short telomeres and telomere aggregates when compared to the mononuclear precursor H-cells. Relapsing Hodgkin's lymphoma is a histologically proven reappearance of the Hodgkin's lymphoma occurring in a variable time (months to years) after the disease was no more identifiable in the person concerned. Refractory Hodgkin's lymphoma is a histologically proven progression of the Hodgkin's lymphoma occurring whilst the patient is under chemo- or radiation therapy. The relapsing or refractory Hodgkin's lymphoma telomeres organization signature is characterized for example by a segmental telomere number (per 5 micron slice at 630× magnification) in RS cells of greater than about 30, greater than about 35, greater than about 40, greater than about 45, or greater than 50; and/or in H cells of greater than 20, greater than 25, greater than 30 or greater than 35. The relapsing or refractory Hodgkin's lymphoma telomeres organization signature is characterized for example by an decreased mean telomere intensity in RS and H cells compared to the remission Hodgkin's lymphoma telomeres organization signature. The relapsing or refractory Hodgkin's lymphoma telomeres organization signature is also characterized for example by an increased percentage of very short telomeres in both RS and H cells compared to the remission Hodgkin's lymphoma telomeres organization signature. For example, relapsing or refractory Hodgkin's lymphoma telomeres organization signature is characterized by greater than 70%, greater than 75%, or greater than 80% very short telomeres in RS cells and greater than 60%, greater than 65%, greater than 70% or greater than 75% very short telomeres in H cells. The relapsing or refractory Hodgkin's lymphoma telomeres organization signature is further characterized for example by an increased percentage of telomeres with a relative fluorescent intensity of less than 5000 or 2500 units, optionally less than 4000, 3000, 2000, 1000 or 500 units. The segmental telomere aggregates (per 5 micron slice at 630× magnification) is also increased compared to the rapid remission signature, for example greater than 4, greater than 4.5, greater than 5, greater than 5.5 or greater than 6 in RS cells and greater than 2.5, greater than 3, greater than 3.5 or greater than 4 in H cells. As indicated in the Table below, the differences between these parameters in the relapsing or refractory and the remission Hodgkin's lymphoma telomeres organization signature are significant.

The term "relapsed MM telomere signature" as used herein refers to the telomere characteristics of patients with relapsed MM. For example, patients with relapsed MM have low telomeric signals and few telomeres detectable per nuclear volume, telomeric aggregates and a/c ratios that differ from MM and MGUS.

The term "sample" as used herein refers to any biological fluid comprising a cell, a cell or tissue sample from a subject including a sample from a test subject, i.e. a test sample, such as from a subject, for example, a subject with a cancer, wherein the test sample comprises cancer cells, and a control sample from a control subject, e.g., a subject without a cancer, or an earlier stage cell e.g. precancer cell. For example for MM, the sample comprises a blood or bone marrow sample comprising plasma cells; for Hodgkin's lymphoma the sample comprises a mononuclear Hodgkin cell or multinuclear Reed-Sternberg (RS) cell; and for MDS/AML a HSC and/or leukemic cell. The sample can comprise a blood sample, for example a peripheral blood sample, a fractionated blood sample, a bone marrow sample, a biopsy, a frozen tissue sample, a fresh tissue specimen, a cell sample, and/or a paraffin embedded section. The sample comprises for example at least 20 cells, at least 25 cells or at least 30 cells or any number between 20 and 30.

The term "subject" as used herein includes all members of the animal kingdom including mammals, and suitably refers to humans.

The term "three-dimensional (3D) analysis" as used herein refers to any technique that allows the 3D visualization of cells, for example involving high resolution deconvolution microscopy.

The term "telomeric organization" as used herein refers to the 3D arrangement of the telomeres during any phase of a cell cycle and includes such parameters as alignment (e.g. nuclear telomere distribution), state of aggregation, telomere numbers per cell and/or telomere sizes, a/c ratios and/or nuclear volumes. "Telomere organization" also refers to the size and shape of the telomeric disk, captured for example in an a/c ratio and which is the organized structure formed when the telomeres condense and align during the late G2 phase of the cell cycle. The term "state of aggregation" refers to the presence or absence of telomere aggregate(s) and/or the size and shape of the aggregates of telomeres. For example, telomeres with a relative fluorescent intensity (x-axis) ranging from 0-5,000 units are classified as very short, with an intensity ranging from 5,000-15,000 units as short, with an intensity from 15,000-30,000 units as mid-sized, and with an intensity >30,000 units as large. As another example, telomere aggregates are defined as clusters of telomeres that are found in close association and cannot be further resolved as separate entities at an optical resolution limit of 200 nm.

The "difference or similarity in telomeric organization between the sample and the control and/or in the test cell compared to the control cell and/or the test sample cell telomeres organization signature and the reference telomeres organization signature" can be determined, for example by counting the number of telomeres in the cell, measuring the size or volume of any telomere or telomere aggregate, or measuring the alignment of the telomeres, and comparing the difference between the cells in the sample and the cells in the control. The differences and similarities in telomeric organization between the sample and the control or reference can be measured and compared using individual cells or average values from a population of cells. For example, if any telomere in the test cell is larger (i.e. forms more aggregates), for example double the size, of those in the control cell, then this indicates the presence of genomic instability in the test cell. The telomeres in a test cell may also be fragmented and therefore appear smaller than those in the control cell. Accordingly, a change or difference in telomeric organization in the test cell compared to the control cell can be determined by comparing parameters used to characterize the organization of telomeres. Such parameters are determined or obtained for example, using a system and/or method described herein below.

The term "telomere aggregates" means telomeres found in clusters that at an optical resolution limit of 200 nm cannot be further resolved (Vermolen et al., 2005; Mai and Garini, 2006; Mai, 2010). Telomeric aggregates are not typically seen in normal cells.

The term "treating" or "treatment" as used herein and as is well understood in the art, means an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, diminishment of the reoccurrence of disease, and remission (whether partial or total), whether detectable or undetectable. "Treating" and "Treatment" can also mean prolonging survival as compared to expected survival if not receiving treatment. "Treating" and "treatment" as used herein also include prophylactic treatment. For example, a subject with early stage leukemia can be treated to prevent progression or metastases, or alternatively a subject in remission can be treated with a compound or composition described herein to prevent recurrence. Treatment methods comprise administering to a subject a therapeutically effective amount of a compound described herein and optionally consists of a single administration, or alternatively comprises a series of applications. For example, the compounds described herein may be administered at least once a week. However, in another embodiment, the compounds may be administered to the subject from about one time per three weeks, or about one time per week to about once daily for a given treatment. In another embodiment, the compound is administered twice daily. The length of the treatment period depends on a variety of factors, such as the severity of the disease, the age of the patient, the concentration, the activity of the compounds described herein, and/or a combination thereof. It will also be appreciated that the effective dosage of the compound used for the treatment or prophylaxis may increase or decrease over the course of a particular treatment or prophylaxis regime. Changes in dosage may result and become apparent by standard diagnostic assays known in the art. In some instances, chronic administration may be required. For example, the compounds are administered to the subject in an amount and for a duration sufficient to treat the patient.

The term "very small telomeres" as used herein means telomeres with a relative fluorescent intensity (x-axis) ranging from 0-5,000 units are classified as very short.

As used herein "segmental nuclear volume" refers to a nuclear volume within for example one 5 µm thin nuclear section cells, for example H-cells or RS-cells, calculated according to the 3D nuclear DAPI staining as previously described (Sarkar R, Guffei A, Vermolen B J, Garini Y, Mai S. Alterations of centromere positions in nuclei of immortalized and malignant mouse lymphocytes. *Cytometry A.* 2007; 71(6):386-392). Contrary to whole cell preparations (cells or cell lines), where the nuclei can be visualized with their entire volumes and z-stack analysis along the z-direction over 15 µm allows to calculate the entire nuclear volume, in tissue sections the nuclear volume analysis is limited to 5 µm nuclear segments (as used as a standard for histopathologic diagnosis) along the z-direction. Deparaffinized tissue slides of 10 and 15 µm thickness are technically unsatisfactory for Q-FISH analysis. Thus, the segmental nuclear volume represents a portion of the total nuclear volume for example about 30-50% of the total nuclear volume of H-cells (nuclear diameter of about 10-15 µm) and about 15-25% of the total nuclear volume of RS-cells (diameter of two up to several nuclei about 20-40 µm).

The term "segmental telomere number" as used herein means a sum of all very short, short, mid-sized and large telomeres and aggregates identified within a segment, e.g. 5 µm thin nuclear section of a cell.

The term "segmental telomere intensity" as used herein means a sum of intensities of all very short, short, mid-sized and large telomeres and aggregates identified within a segment, e.g. a 5 µm thin nuclear section of a cell such as a H-cell or RS-cell (viz. $\Sigma 2 \times 15\,000$ units$>\Sigma 7 \times 4000$ units).

The term "mean telomere intensity" as used herein means a mean telomere relative fluorescent intensity (length) of all telomeres within a given segmental volume.

The term "telomere length" as used herein refers to the relative fluorescent intensity of telomeres. For example telomeres with a relative fluorescent intensity (x-axis) ranging from 0-5,000 units are classified as very short, with an intensity ranging from 5,000-15,000 units as short, with an intensity from 15,000-30,000 units as mid-sized, and with an intensity >30,000 units as large (Knecht H, Sawan B, Lichtensztejn Z, Lichtensztejn D, Mai S. 3D telomere FISH defines LMP1 expressing Reed-Sternberg cells as end-stage cells with telomere-poor "ghost" nuclei. *Lab Invest.* 2010; 90(4):611-619).

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives.

The term "consisting" and its derivatives, as used herein, are intended to be closed ended terms that specify the presence of stated features, elements, components, groups, integers, and/or steps, and also exclude the presence of other unstated features, elements, components, groups, integers and/or steps.

Further, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

More specifically, the term "about" means plus or minus 0.1 to 50%, 5-50%, or 10-40%, 10-20%, 10%-15%, preferably 5-10%, most preferably about 5% of the number to which reference is being made As used in this specification and the appended claims, the singular forms "a", "an" and "the" include plural references unless the content clearly dictates otherwise. It should also be noted that the term "or" is generally employed in its sense including "and/or" unless the content clearly dictates otherwise.

The definitions and embodiments described in particular sections are intended to be applicable to other embodiments herein described for which they are suitable as would be understood by a person skilled in the art.

The recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about."

Further, the definitions and embodiments described are intended to be applicable to other embodiments herein described for which they are suitable as would be understood by a person skilled in the art. For example, in the above passages, different aspects of the invention are defined in more detail. Each aspect so defined can be combined with any other aspect or aspects unless clearly indicated to the contrary. In particular, any feature indicated as being preferred or advantageous can be combined with any other feature or features indicated as being preferred or advantageous.

II. Methods and Systems

The present disclosure provides methods and systems for patient stratification, cancer monitoring and the design of personalized treatments. The inventors have determined that the three-dimensional organization of telomeres in hematological cancers can be used for the detecting disease progression.

Technology for three-dimensional (3D) organization of telomeres in cancer cells has been developed and is disclosed in U.S. Pat. No. 7,801,682, issued Sep. 21, 2010, and U.S. patent application Ser. No. 11/573,967, each of which are incorporated herein by reference that effectively assesses the 3D architecture of telomeres.

The inventors' research has shown that the 3D organization of telomeres is altered in cancer cells (Chuang et al., 2004; Mai and Garini, 2006). This basic finding led to an understanding of genetic changes in early cancer cells and proved that telomere organization is key to genome stability vs. instability (Mai and Garini, 2006; Mai and Garini, 2005; Louis et al., 2005): The inventors have demonstrated that each nucleus has a specific telomeric signature that defines it as normal or aberrant. Four criteria define this difference; 1) nuclear telomere distribution, 2) the presence/absence of telomere aggregate(s), 3) telomere numbers per cell, and 4) telomere sizes (Mai, 2010). Additional criteria include a/c ratios and nuclear volumes.

As disclosed herein, 3D telomere analysis of diagnostic samples is able to provide prognosis information in different hematological cancers—specific 3D telomere signatures distinguish between MGUS, MM and relapsed MM; and between refractory or relapsing Hodgkin's lymphoma and rapid remission Hodgkin's lymphoma. Distinctions between MDS and AML nuclear telomeric organization have been identified.

For example, it is demonstrated that bi- or multinuclear RS-cells of patients classified as rapid emission and relapse patients showed significant increase of very short telomeres and telomere aggregates when compared to the mononuclear precursor H-cells. Importantly, diagnostic biopsies of the relapse group contained a very high percentage of very small telomeres, including so-called "t-stumps" in both, H-cells (76.8±11.8%) and RS-cells (87.9±7.3%). Compared to the percentage of very small telomeres identified in both, H-cells (33.7±9.4%) and RS-cells (54.6±15.0%) of the rapid remission group, this increase is highly significant ($p<0.001$). Moreover, analogous findings are observed for the number of telomere aggregates. In the relapse group the average numbers of telomere aggregates per cell were 4.3±2.4 aggregates per H-cell and 5.4±3.0 aggregates per RS-cell, compared to 1.2±0.7 aggregates per H-cell and 3.3±1.1 aggregates per RS-cell in the rapid remission group.

The methods can also for example be used for assessing signatures in precancer hematological disorders that can progress cancer.

In myeloma and acute leukemia for example, it is well established that over time additional mutations and translocations will occur and the tumour cells become more aggressive but there is little knowledge about the stages before diagnosis. In Hodgkin's lymphoma, it is now known that there are circulation monoclonal precursor cells in the peripheral blood, but it is not yet possible to identify the degree of chromosomal anomaly within these circulating cells. The 3D telomere analysis will offer a powerful tool to uncover such subtle anomalies.

The disclosure provides methods of prognosing clinical outcome in a subject known to have a hematological disorder using high-resolution deconvolution, or equivalent, 3D microscopy and imaging, and 3D quantitative analysis.

Accordingly in an aspect, the disclosure includes a method of prognosing a clinical outcome in a subject with a hematological disorder comprising:

a) determining a 3D telomeres organization signature of a test sample cell from the subject;

wherein the 3D telomeres organization signature of the test sample cell is indicative of the clinical outcome of the subject.

In an embodiment, the method further comprises step b), comparing the 3D telomeres organization signature of the test sample cell with a 3D telomeres organization signature in a control, wherein a difference or similarity in the 3D telomeres organization signature between the test sample cell and the control is indicative of the clinical outcome of the subject.

In an embodiment, the clinical outcome is progression.

Accordingly, a further aspect is a method for determining risk of progression in a subject with a hematological disorder and/or cancer comprising:
 a) determining a 3D telomeres organization signature of a test sample cell from the subject;
wherein the 3D telomeres organization signature of the test sample cell is indicative of the progression of the subject.

In an embodiment, the method further comprises step b), comparing the 3D telomeres organization signature of the test sample cell with a 3D telomeres organization signature in a control, wherein a difference or similarity in the 3D telomeres organization signature between the test sample cell and the control is indicative of the progression of the subject.

In an embodiment, the method is used to predict likelihood of progression in a subject with a hematological malignancy precursor condition (e.g. MGUS) to ascertain likelihood of progression to cancer (e.g. MM). In another embodiment, the method is used to predict likelihood of progression in a subject with MM to ascertain likelihood of progression to relapse.

In an embodiment, the clinical outcome is recurrence.

Accordingly, an aspect of the disclosure includes a method of predicting a likelihood of recurrence comprising:
 a) determining a 3D telomeres organization signature of a test sample cell from the subject;
wherein the 3D telomeres organization signature of the test sample cell is indicative of the likelihood of recurrence in the subject.

In an embodiment, the method further comprises step b), comparing the 3D telomeres organization signature of the test sample cell with a 3D telomeres organization signature in a control, wherein a difference or similarity in the 3D telomeres organization signature between the test sample cell and the control is indicative of the likelihood of recurrence in the subject.

The method can also be used to determine disorder subtype.

Accordingly, an aspect includes a method of identifying hematological disorder subtype of a subject comprising:
 a) determining a 3D telomeres organization signature of a test sample cell from the subject;
wherein the 3D telomeres organization signature of the test sample cell is indicative of the hematological disorder subtype in the subject.

In an embodiment, the method further comprises step b), comparing the 3D telomeres organization signature of the test sample cell with a 3D telomeres organization signature in a control, wherein a difference or similarity in the 3D telomeres organization signature between the test sample cell and the control is indicative of the disorder subtype in the subject.

In an embodiment, the method comprises:
 a) determining a 3D telomeres organization signature of a test sample cell from the subject;
 b) comparing the 3D telomeres organization signature of the test sample cell with a 3D telomeres organization signature in a control comprising;
  1. providing one or more reference 3D telomeres organization signatures associated with a clinical outcome and/or disorder subtype; and
  2. identifying the reference 3D telomeres organization signature most similar to the test sample cell 3D telomeres organization signature;
wherein a difference or similarity in the 3D telomeres organization signature between the test sample cell and the control is indicative of the clinical outcome or disorder subtype of the subject.

In an embodiment, the 3D telomeres organization signature comprises one or more of the following 3D telomeric criteria: telomere number, telomere size, presence and/or number of telomeric aggregates, telomeres per nuclear volume, distances from nuclear centre and a/c ratio. In another embodiment, the 3D telomeres organization signature comprises one or more of the following 3D telomeric criteria: number of telomeres/cell (total telomere volume) and number of short telomeres.

The numbers for example can be provided as percentages.

The method can be used for example, to identify patient subgroups, for example for stratifying patients in a clinical trial. In an embodiment, subjects with a similar 3D telomeres organization signature can be grouped to assess for example treatment response.

In an embodiment, the method is for use in diagnosing a patient diagnosis, in the detection of minimal residual disease, and/or in the analysis of treatment response and/or in treatment decisions.

A further aspect of the disclosure includes a method of treating a subject with a hematological disorder comprising:
 a) obtaining a test sample from the subject;
 b) predicting the clinical outcome or cancer subtype in the subject according to any method described herein; and
 c) administering to the subject a treatment suitable for the predicted clinical outcome or cancer subtype.

The methods described herein provide for example for 1) for the distinction of normal and tumor cells (Klewes et al., 2011), 2) for the identification of patient subgroups (Gadji et al., 2010) that will allow for new treatment design, 3) for the identification of patients who will recur and therefore should obtain different treatments (Knecht et al., 2010), 4) for treatment monitoring, and 5) for personalized medical management of patients.

As described below, 3D telomeric criteria allow for the objective assessment of MGUS, MM, MGUS/MM transition, and MM/relapsed MM transition have been developed. A distinction between MGUS and MM has been demonstrated. Further, it is demonstrated that sub-populations in MGUS that start to transform to MM can be detected allowing for early detection of MGUS/MM transition, enabling monitoring and patient-based risk assessment and treatment decision. In addition, early detection of progression from MM to MM relapse can be detected, enabling early intervention so that treatments can be designed and/or administered.

In an embodiment, the hematological disorder is multiple myeloma.

In an embodiment, the test sample cell is a plasma cell. In an embodiment, the plasma cell is a peripheral blood plasma cell. In another embodiment, the plasma cell is a bone marrow plasma cell. A plasma cell for example is characterized by abundant basophile cytoplasm, a prominent Golgi zone and an eccentrically located nucleus. In addition they express the specific marker CD138 for immunohistochemical detection. Plasma cells can readily be identified using a light microscopic technique in bone marrow and blood smears. These cells can be isolated using methods known in the art. In relapsing MM for example, the plasma cells harbor additional mutations, acquired after several rounds of mitosis with BBF-cycles and shortening of the telomeres.

It is demonstrated herein that plasma cells from MM, MGUS and relapsed MM exhibit different 3D telomeric signatures. For example, MM have the highest telomere numbers, followed by MGUS and relapsed MM has the lowest number of telomeres per cell. Relapsed MM also for example has the shortest telomeres.

For example, a double blinded study with 78 patients, including 40 MM, 30 MGUS and 8 relapsed MM was conducted. Using blood- and bone marrow-derived plasma cells from the respective patient groups, the 3D nuclear telomeric profiles of the patients was examined. Plasma cells from MM, MGUS and relapsed MM exhibit specific 3D telomeric signatures. MM has the highest telomere numbers, followed by MGUS, while relapsed MM presents with the lowest numbers of telomeres and the shortest telomeres. Additional telomere parameters, such as cell cycle distribution profiles (a/c ratio), telomere aggregate numbers, distances from nuclear centre also exhibited significance ($p<0.001$) (see FIG. 1).

In an embodiment, the method comprises:
a) determining a 3D telomeres organization signature of a test sample cell from the subject;
b) comparing the 3D telomeres organization signature of the test sample cell with a 3D telomeres organization signature in a control comprising;
 1. providing one or more reference 3D telomeres organization signatures selected from a MGUS telomeres organization signature, a MM telomeres organization signature and a relapsed MM telomeres organization signature; and
 2. identifying the reference 3D telomeres organization signature most similar to the test sample cell 3D telomeres organization signature;
wherein a difference or similarity in the 3D telomeres organization signature between the test sample cell and the control is indicative of the clinical outcome or disorder subtype of the subject.

For example, a test sample cell telomeres organization signature from a subject with MGUS most similar to a MM telomeres organization signature, (e.g. with high telomere numbers per cell compared to a MGUS telomeres organization signature or relapsed MM telomeres organization signature) is indicative the subject has an increased risk to progress to MM (e.g. compared to a subject with a test sample cell telomeres organization signature most similar to a MGUS telomeres organization signature. Further, a test sample cell telomeres organization signature in a subject with MM most similar to a relapsed MM telomeres organization signature is indicative that the subject has an increased likelihood of MM recurrence (e.g. compared to a subject with a test sample cell telomeres organization signature most similar to a MM telomeres organization signature).

Accordingly, in an embodiment, the method comprises:
a) determining a 3D telomeres organization signature of a test sample cell from the subject, wherein the subject is has MGUS;
b) comparing the 3D telomeres organization signature of the test sample cell with a 3D telomeres organization signature in a control comprising;
 1. providing one or more reference 3D telomeres organization signatures selected from a MGUS telomeres organization signature, and a MM telomeres organization signature; and
 2. identifying the reference 3D telomeres organization signature most similar to the test sample cell 3D telomeres organization signature;
wherein a similarity in the 3D telomeres organization signature between the test sample cell and the MM telomeres organization signature is indicative the subject has an increased risk of progression to MM.

In another embodiment, the method comprises
a) determining a 3D telomeres organization signature of a test sample cell from the subject, wherein the subject has MM;
b) comparing the 3D telomeres organization signature of the test sample cell with a 3D telomeres organization signature in a control comprising;
 1. providing one or more reference 3D telomeres organization signatures selected from a MM telomeres organization signature, and a relapsed MM telomeres organization signature; and
 2. identifying the reference 3D telomeres organization signature most similar to the test sample cell 3D telomeres organization signature;
wherein a similarity in the 3D telomeres organization signature between the test sample cell and the relapsed MM telomeres organization signature is indicative the subject has an increased risk of MM recurrence.

Depending on the stage, a subject will have a signature more similar to a MGUS signature (e.g. early stage) or more similar to a MM signature (e.g. later stage).

As mentioned, increased telomere numbers are seen in MM subjects, followed by MGUS.

For example, as shown in FIG. 1, using TeloView, telomere intensity in MM relapsed ranges from about 0 to about 40,000; telomere intensity in MGUS ranges from about 0 to about 80,000; and in MM telomere intensity ranges from about 0 to about 120,000. Accordingly, in an embodiment, a subject with telomere intensities falling between about 0 to 40,000 or any increment of 500 in between (e.g. about 500 to about 40,000; about 500 to about 39,500; about 1000 to about 40,000; about 1000 to about 39,500 etc.) is identified as having a telomere signature most similar to a MM relapsed signature and as having an increased risk of relapse. In an embodiment, a subject with a telomere intensities falling between about 0 to about 80,000 or any increment of 500 in between is identified as having a telomere signature most similar to a MGUS signature.

In another embodiment, a subject with a telomere intensities falling between about 0 to about 80,000 or any increment of 500 in between is identified as having a telomere signature most similar to a MM signature.

Accordingly in an embodiment, the method comprises:
a) determining a 3D telomeres organization signature of a test sample cell from the subject, wherein the subject is has MGUS;
b) comparing the 3D telomeres organization signature of the test sample cell with a 3D telomeres organization signature in a control, wherein the signature comprises one or more of telomere numbers and number of aggregates;
wherein an increased number of telomere numbers in the test sample compared to the control is indicative of an increased likelihood of progression to MM.

Relapsed MM subjects are disclosed to have the lowest numbers of telomeres and the shortest telomeres. Cell cycle distribution profiles (a/c) ratio, telomere aggregate numbers, distances from nuclear centre also exhibited significant differences.

For example, it is found that a/c ratio is higher in relapse than in MM than in MGUS (p<0.0001); telomere aggregate numbers: higher in relapse than in MM, than in MGUS (p<0.0001); and that telomeres per nuclear volume: more in MM than in MGUS than in relapse (p<0.0001).

Accordingly in an embodiment, the method comprises:
a) determining a 3D telomeres organization signature of a test sample cell from the subject, wherein the subject is has MM;
b) comparing the 3D telomeres organization signature of the test sample cell with a 3D telomeres organization signature in a control, wherein the signature comprises one or more of telomere numbers and number of aggregates;

wherein a decreased number of telomere numbers and/or an increased number of telomere aggregates, in the test sample compared to the control is indicative of an increased likelihood of MM recurrence.

In an embodiment, the control comprises a sample from a subject with MGUS or non-relapsing MM.

Other risk assessment criteria can also be used in conjunction with assessing 3D telomere signatures. For example, patient monitoring based on 3D telomeric signatures of plasma cells can include assessing Mayo Clinic Model or Spanish Group Model risk assessment for disease progression in MM. In an embodiment, the method comprises assessing additional clinical parameters. In an embodiment, the method further comprises assessing non-IgG isotype, M protein concentration, serum free light chain ratio, CD138 level, CD38 level, CD56 level, CD19 level, and/or CD45 level.

For example, the Mayo Clinic model is based on protein levels (non-IgG isotype, M protein concentration>1.5 g/dL, and an abnormal serum free light chain ratio) (Rajkumar, 2005).

In the Mayo Clinic model, patients with all three risk factors have a cumulative risk of progression at 10 years of 84%. Having two risk factors place them at 65%, one risk factor at 50% cumulative risk of progression at 10 years (Mailankody et al., 2010). In the Spanish model, flow cytometry is used to detect normal vs. aberrant plasma cells (CD138 expression and intensive CD38 in normal plasma cells, while they detect CD138 expression and low CD38 levels in aberrant plasma cells, expression of CD56, absence of CD19 and CD45) (for review, see Mailankody et al., 2010) and to define the cumulative risk of progression. For example, over a period of 5 years, it is 2%, 10% and 46% respectively with no, one or two risk factors.

In an embodiment, a subject having MGUS identified to have a signature resembling a MM telomeres organization signature is treated for MM.

In another embodiment, a subject having MM identified to have a signature resembling a relapsed MM telomeres organization signature is treated for relapsed MM.

In an embodiment, the hematological disorder is Hodgkin's lymphoma. In an embodiment the subject with Hodgkin's lymphoma has initiated chemotherapy. In an embodiment, the chemotherapy is ABVD.

In an embodiment the test sample is a diagnostic biopsy. A diagnostic biopsy is taken for example prior to treatment. A diagnostic sample is a sample of tissue which defines the first time a disease under investigation. For example, a lymph node biopsy can reveal a subject has a carcinoma metastasis, a non Hodgkin's lymphoma or a Hodgkin's lymphoma. The diagnostic biopsy can provide a basis to start a specific treatment In an embodiment, the test sample is aLMP1 expressing, nodular sclerosis subtype, or mixed cellularity subtype. In an embodiment, the sample stage is IA, IIA, IIIA, IIIB or IVA. For more than 30 years the modified Ann Arbor (Costwold) classification has been used to determine the stage (expansion of a disease). Stages I and II indicate one and two or more lymph node stations on one side of the diaphragm. Stage III disease is on both sides of the diaphragm and stage 1V disease includes bone marrow involvement. "B" indicates advanced clinical symptoms as weight loss, fever or sweating.

In an embodiment, the test sample cell type is bi- or multi-nuclear Reed Sternberg cell. In an embodiment, the test sample cell is a mononuclear precursor H cell.

It is demonstrated herein that bi- and multi-nuclear Reed Sternberg cells of subjects with Hodgkin's lymphoma have a significant increase of very short telomeres and telomere aggregates when compared to the mononuclear precursor H-cell. Relapsing patients contained a very high percentage of very small telomeres in both H cells and RS cells.

In an embodiment, the sample is a lymph node biopsy. In an embodiment, the method comprises analyzing at least 30 H cells and at least 30 RS cells.

In an embodiment, the method comprises:
a) determining a 3D telomeres organization signature of a test sample cell from the subject;
b) comparing the 3D telomeres organization signature of the test sample cell with a 3D telomeres organization signature in a control comprising;
1. providing one or more reference 3D telomeres organization signatures selected from a rapid remission Hodgkin's lymphoma telomeres organization signature, and a relapsing or refractory Hodgkin's lymphoma telomeres organization signature; and
2. identifying the reference 3D telomeres organization signature most similar to the test sample cell 3D telomeres organization signature;

wherein a difference or similarity in the 3D telomeres organization signature between the test sample cell and the control is indicative of the clinical outcome or disorder subtype of the subject.

For example, a telomeres organization signature in a subject with Hodgkin's lymphoma most similar to a relapsing or refractory Hodgkin's lymphoma telomeres organization signature, (e.g. with high very small telomeres numbers per cell compared to a rapid remission telomeres organization signature) is indicative the subject has an increased risk of recurrence or refractory disease (e.g. compared to a subject with a test sample cell telomeres organization signature most similar to a rapid remission telomeres organization signature).

Accordingly, in an embodiment, the method comprises:
a) determining a 3D telomeres organization signature of a test sample cell from the subject, wherein the subject is has Hodgkin's lymphoma and has initiated chemotherapy;
b) comparing the 3D telomeres organization signature of the test sample cell with a 3D telomeres organization signature in a control comprising;
2. providing one or more reference 3D telomeres organization signatures selected from a rapid remission Hodgkin's lymphoma telomeres organization signature, and a relapsing or refractory Hodgkin's lymphoma telomeres organization signature; and
3. identifying the reference 3D telomeres organization signature most similar to the test sample cell 3D telomeres organization signature;

wherein a similarity in the 3D telomeres organization signature between the test sample cell and relapsing or refractory Hodgkin's lymphoma telomeres organization signature is indicative the subject has an increased risk of Hodgkin's lymphoma recurrence and/or refractory disease.

For example, it is demonstrated herein that relapses and primary refractory Hodgkin's lymphoma have a most similar telomere signature. This signature is for example, indicative of highly aggressive tumor cells.

In an embodiment, a segmental telomere number (per 5 micron slice at 630× magnification) in RS cells of less than about 30, less than about 25, less than about 20 and/or in H cells of less than 20, less than 15, less than 13 or less than 10, is indicative of an increased likelihood of remission and a decreased risk of relapse and/or refractory disease.

In an embodiment, a segmental telomere number (per 5 micron slice at 630× magnification) in RS cells of greater than about 30, greater than about 35, greater than about 40, greater than about 45, or greater than 50; and/or in H cells of greater than 20, greater than 25, greater than 30 or greater than 35, is indicative of an increased risk of relapse and/or refractory disease and a decreased likelihood of remission.

In an embodiment, an increased number of very small telomeres, including for example "t-stump" telomeres in the test sample compared to the control, is indicative of Hodgkin's relapse or refractory disease.

Accordingly in an embodiment, the method comprises:
a) determining a 3D telomeres organization signature of a test sample cell from the subject, wherein the subject is has Hodgkin's lymphoma and has initiated chemotherapy;
b) comparing the 3D telomeres organization signature of the test sample cell with a 3D telomeres organization signature in a control;

wherein an increased number of very small telomeres, including for example "t-stump" telomeres in the test sample compared to the control is indicative of an increased risk of Hodgkin's relapse or refractory disease.

In an embodiment, a decreased number of very short telomeres including "t-stumps" in the test sample compared to the control is indicative of treatable Hodgkin's lymphoma and/or an increased likelihood of disease free survival (e.g. for 5 years).

In an embodiment, the control and/or relapsing or refractory Hodgkin's lymphoma telomeres organization signature comprises RS cells that contain at least 45%, at least 50%, at least 55%, at least 60% at least 65%, at least 70%, at least 75%, at least 80% or at least 85% very small telomeres, including for example "t-stump" telomeres.

In an embodiment, the control and/or relapsing or refractory Hodgkin's lymphoma telomeres organization signature comprises H cells that contain at least 35%, at least 40%, at least 45%, at least 50%, at least 55%, at least 60% at least 65%, at least 70% or at least 75% very small telomeres, including for example "t-stump" telomeres.

As mentioned, the rapid remission Hodgkin's lymphoma telomeres organization signature is also characterized for example by a decreased percentage of very short telomeres in both RS and H cells compared to the relapsing or refractory Hodgkin's lymphoma telomeres organization signature. In an embodiment, less than 70%, less than 65%, less than 60% very short telomeres in RS cells and less than 60%, less than 55%, less than 50% very short telomeres in H cells is indicative of an increased likelihood of remission and a decreased risk or progression and/or relapse.

In another embodiment, greater than 70%, greater than 75%, or greater than 80% very short telomeres in RS cells and greater than 60%, greater than 65%, greater than 70% or greater than 75% very short telomeres in H cells is indicative of an increased risk of relapse or progression and a decreased likelihood of remission.

In an embodiment, an increased number of telomere aggregates, in the test sample compared to the control is indicative of Hodgkin's relapse or refractory disease.

Accordingly in an embodiment, the method comprises:
a) determining a 3D telomeres organization signature of a test sample cell from the subject, wherein the subject is has Hodgkin's lymphoma and has initiated chemotherapy;
b) comparing the 3D telomeres organization signature of the test sample cell with a 3D telomeres organization signature in a control;

wherein an increased number of telomere aggregates, in the test sample compared to the control is indicative of an increased risk of Hodgkin's relapse or refractory disease.

In an embodiment, a decreased number of telomere aggregates in the test sample compared to the control is indicative of treatable Hodgkin's lymphoma and/or an increased likelihood of disease free survival (e.g. for 2 years, 2½ years, 3 years, 4 years or 5 years). For example, results of a study over 5 years shows that Hodgkin- and Reed Sternberg cells of biopsies from patients entering rapid and lasting remission (mean 30 months) display a significantly different telomere signature (much less aggregates and fewer very short telomeres) compared to relapses and progressing disease.

In an embodiment, the control and/or relapsing or refractory Hodgkin's lymphoma telomeres organization signature comprises H cells that contain at least about 1, at least about 1.5, at least about 2, at least about 2.5, at least about 3, at least about 3.5, or at least about 4, aggregates per cell.

In an embodiment, the control and/or relapsing or refractory Hodgkin's lymphoma telomeres organization signature comprises RS cells that contain at least about 3, at least about 3.5, at least about 4, at least about 4.5, at least about 5, at least about 5.5, or at least about 6, aggregates per cell.

In an embodiment, a segmental telomere aggregate (per 5 micron slice at 630× magnification) of less than 4, less than 3.5, or less than 3 in RS cells and less than 2.5, less than 2 or less than 1.5 in H cells is indicative of an increased likelihood of remission and an increased risk or relapse and/or progression (e.g. refractory disease).

In an embodiment, a segmental telomere aggregate (per 5 micron slice at 630× magnification) of greater than 4, greater than 4.5, greater than 5, greater than 5.5 or greater than 6 in RS cells and greater than 2.5, greater than 3, greater than 3.5 or greater than 4 in H cells is indicative of an increased risk or progression or relapse and a decreased likelihood of remission. As indicated in the Table below, the differences between these parameters in the relapsing or refractory and the remission Hodgkin's lymphoma telomeres organization signature are significant.

The three-dimensional telomere dynamics that can be used to indicate refractory and/or relapsing Hodgkin's lymphoma versus treatable and/or remission Hodgkin's lymphoma can be identified before chemotherapy is initiated. Thus, the different clinical courses observed are independent of the initial treatment modality.

Accordingly, in one embodiment, the present methods are performed on a sample from a subject with Hodgkin's lymphoma who has not been subject to chemotherapy or where chemotherapy has not been initiated. In other embodiment, the present methods are performed on a sample from a subject with Hodgkin's lymphoma who has only been subject to 1, 2 or 3 rounds of chemotherapy. Optionally, the chemotherapy is ABVD chemotherapy.

The present application also discloses that in patients with refractory or relapsing Hodgkin's lymphoma, the mononuclear H cells have 3D nuclear telomere signatures that are similar to RS cells. In other words, the mononuclear H cells of refractory/relapsing cases of Hodgkin's lymphoma behave in their three-dimensional nuclear telomere signature like end-stage RS cells in remission cases of Hodgkin's lymphoma. For example, the mononuclear H cells in patients with refractory or relapsing Hodgkin's lymphoma have similar percentage of very small telomeres and number of aggregates per cell to compared to RS cells in rapid remission Hodgkin's lymphoma. Further, as shown in Table 8 herein (far right column), there is no significant difference in the segmental telomere number, segmental telomere intensity, mean telomere intensity, percentage of very short telomeres and number of segmental telomere aggregates in H cells in patients with refractory or relapsing Hodgkins compared to RS cells of patients in the rapid remission group.

Therefore, in another embodiment, one or both of a RS cell nuclei 3D telomeres organization signature and an H cell nuclei 3D telomeres organization signature is obtained from the test sample and compared to one or more RS cell nuclei 3D telomeres organization reference signature and H cell nuclei 3D telomeres organization reference signature each associated with a clinical outcome.

In a further embodiment, the test sample H cell nuclei 3D telomeres organization signature is compared to one or more the reference signatures, and an H cell nuclei 3D telomeres organization signature that is similar to a RS cell nuclei 3D telomeres organization reference signature is indicative the subject is likely to have refractory Hodgkin's lymphoma and/or to relapse.

Optionally, when the percentage of very small telomeres in mononuclear H cells is within 2, 5, 10, 15 or 20% of the percentage of very small telomeres in RS cells, refractory and/or relapsing Hodgkin's lymphoma is indicated. Optionally, when the number of aggregates per cell in mononuclear H cells is within 0.005, 0.1, 0.2, 0.3, 0.4, 0.5, 0.6, 0.7 or 0.8 of the number of aggregates per cell in RS cells, refractory and/or relapsing Hodgkin's lymphoma is indicated. In another embodiment, when there is no statistically significant difference between the number of aggregates per cell in H cells compared to RS cells, optionally RS cells from a subject in remission, refractory and/or relapsing Hodgkin's lymphoma is indicated.

In another embodiment, a similar number of telomere aggregates and/or very small telomeres, including for example "t-stump" telomeres, in the RS cell nuclei 3D telomeres organization signature compared to the H cell nuclei 3D telomeres organization signature is indicative that the subject is likely to have refractory Hodgkin's lymphoma and/or to relapse. In another embodiment, when there is no statistically significant difference between the percentage of very small telomeres in H cells compared to RS cells, optionally RS cells from a subject in remission, refractory and/or relapsing Hodgkin's lymphoma is indicated. In another embodiment, an H cell nuclei 3D telomeres organization signature that is similar to a remission RS cell nuclei 3D telomeres organization signature is indicative that the subject is likely to have refractory Hodgkin's lymphoma and/or to relapse.

The present application also discloses that in patients with progressing or relapsing Hodgkin's lymphoma, compared with mononuclear H-cell-nuclei, RS-cell nuclei have a significantly increased total telomere mass as measured by segmental telomere intensity. This analysis is optionally performed independently of any comparison to reference or control cells.

Thus, in another embodiment, an increased total telomere mass (e.g. segmental telomere intensity) in RS cell nuclei compared to H cell nuclei in the test sample is indicative of relapsing or refractory Hodgkin's lymphoma. Optionally, a total telomere mass of the RS cell nuclei of at least 110%, 115%, 135% or 150% the total telomere mass of the H cell nuclei in the test sample is indicative of relapsing or refractory Hodgkin's lymphoma.

Further, in Hodgkin's patients entering rapid remission, the total telomere mass in RS cell nuclei and H cell nuclei remains nearly unchanged.

Accordingly, in another embodiment, comparable total telomere mass in RS cell nuclei and H cell nuclei in the test sample is indicative the subject is likely to respond to therapy and/or enter remission. Optionally, a total telomere mass of RS cell nuclei that is within 1, 2, 5 or 10% of the total telomere mass of H cell nuclei in the test sample is indicative that the subject is likely to respond to therapy and/or enter remission.

In a further embodiment, an increased number of telomeres with a relative fluorescent intensity of less than 2500 units, in the test sample cell 3D telomeres organization signature compared to the reference 3D telomeres organization signature is indicative of Hodgkin's relapse or refractory disease. In another embodiment, the ratio of RS cells to H cells is used to distinguish between refractive and remission profiles. In particular, a higher ratio of RS cells compared to H cells can be indicative of Hodgkin's relapse or refractory disease.

Other risk assessment criteria can also be used in conjunction with assessing 3D telomere signatures. For example, the methods disclosed can be used in conjunction with other clinical risk criteria such as well known risk factor of advanced stage disease with B-symptoms, microenvironment factors such as fibroblast activation, extracellular matrix remodelling and high number of macrophages.

In an embodiment, a subject identified to have a treatable Hodgkin's lymphoma is treated, for example with ABVD.

In an embodiment, the hematological disorder is AML and the method is used prognose patients with MDS.

In an embodiment, the method allows assessment of tumour aggressiveness and/or stage e.g. likely recurrent or likely non-recurrent, at the time of diagnosis.

3D Image Acquisition and Analysis

In an embodiment, the 3D telomeric organization signature is determined using 3D quantitative FISH (3D q-FISH).

The 3D images can be obtained using a 3D imaging system that enables Abbe resolution of 200 nm, for example an AxiolMager Z2 (Zeiss) microscope.

In an embodiment, the method uses Teloscan™. In another embodiment, the method uses Teloview™. For example, both Teloscan and Teloview can be used to determine the 3D telomere organization of a cell. TeloScan is capable of scanning multiple cells at one time; whereas TeloView scans one cell at a time.

Telomere Q-FISH:

The telomere FISH protocol was performed[6,8] by using Cy3-labelled peptide nucleic acid (PNA) probes (DAKO). Imaging of interphases after telomere FISH was performed by using Zeiss Axiolmager Z1 with a cooled AxioCam HR B&W, DAPI, Cy3 filters in combination with a Planapo 63×/1.4 oil objective lens. Images were acquired by using AXIOVISION 4.6 and 4.8 (Zeiss) in multichannel mode followed by constraint iterative deconvolution as specified below.

3D Image Acquisition:

At least 30 H-cell interphase nuclei and 30 RS-cell interphase polycaria were analyzed in each lymph node slide. AXIOVISION 4.6 and 4.8 with deconvolution module and rendering module were used. For every fluorochrome, the 3D image consists of a stack of 40 images with a sampling distance of 200 nm along the z and 107 nm in the x and y direction. The constraint iterative algorithm option was used for deconvolution.[23]

3D Image Analysis for Telomeres:

Telomere measurements were done with TeloView.[6,24] By choosing a simple threshold for the telomeres, a binary image is found. Based on that, the center of gravity of intensities is calculated for every object resulting in a set of coordinates (x, y, z) denoted by crosses on the screen. The integrated intensity of each telomere is calculated because it is proportional to the telomere length.[25]

Statistical Analysis:

For each case, normally distributed parameters are compared between the two types of cells using nested ANOVA or two-way ANOVA. Multiple comparisons using the least square means tests followed where interaction effects between two factors were found to be significant. Other parameters that were not normally distributed were compared using a nonparametric Wilcoxon rank sum test. Significance level were set at $p=0.05$. Analyses were done using SAS v9.1 programs.

Further, the definitions and embodiments described are intended to be applicable to other embodiments herein described for which they are suitable as would be understood by a person skilled in the art. For example, in the above passages, different aspects of the invention are defined in more detail. Each aspect so defined can be combined with any other aspect or aspects unless clearly indicated to the contrary. In particular, any feature indicated as being preferred or advantageous can be combined with any other feature or features indicated as being preferred or advantageous.

EXAMPLES

Example 1

3D Nuclear Telomeric Profiles of MGUS, MM and Relapsed MM.

Multiple myeloma (MM) is recognized as the second most common cancer of the blood. It is a malignant disorder of plasma cells and commonly affects adults past the age of 50. Although risk factors have been established, it is currently not possible to assess the individual risk to cancer progression. Moreover, the causes of disease progression from its precursor condition, monoclonal gammopathy of undetermined significance (MGUS), to full-blown MM and its progression to relapsed MM remain elusive.

Previous studies performed on the three-dimensional (3D) nuclear organization of telomeres and found that normal and tumour cells display significant differences in their nuclear organization. These differences were objectively quantified with two software programs, TeloView and TeloScan described for example in U.S. Pat. No. 7,801,682, issued Sep. 21, 2010, and U.S. patent application Ser. No. 11/573, 967, each of which are herein incorporated by reference.

Figure 1A:
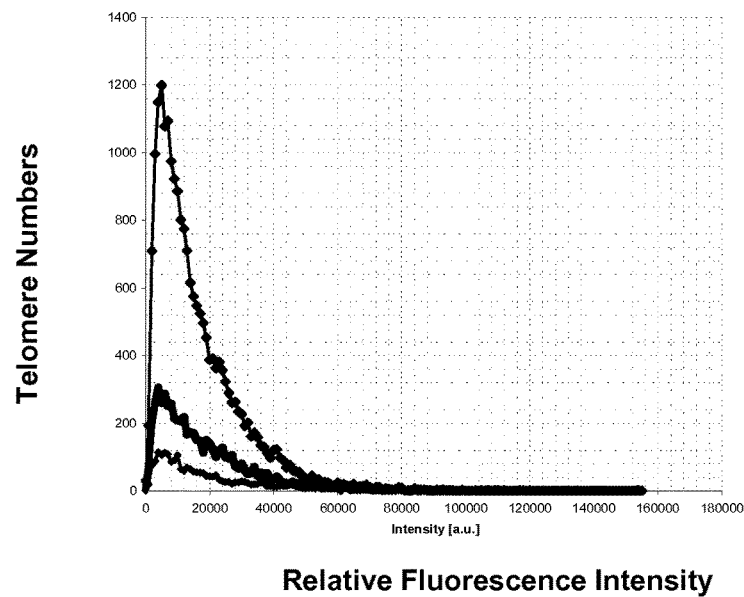
FIG. 1. a) Telomere numbers and relative fluorescent intensities of bone-marrow-derived plasma cells from MM (top line), MGUS (middle line) and relapsed MM b) Image of nucleus in 2D; c) image of the same nucleus in 3D; d) Telomere numbers and relative fluorescent intensities of bone-marrow-derived plasma cells from MM (top line), MGUS (middle line) and relapsed MM (bottom line); e) Automated analysis of telomeric signals in BM samples; f) Semi automated analysis of telomeric signals in blood samples; g) Automated analysis of telomeric signals in peripheral blood.

Reported herein is a new double blinded preliminary study with 36 patients, including 20 MM, 12 MGUS and 4 relapsed MM. Using blood- and bone marrow-derived plasma cells from the respective patient groups, 3D nuclear telomeric profiles of the above patients were examined. Plasma cells from MM, MGUS and relapsed MM exhibit specific 3D telomeric signatures. MM have the highest telomere numbers, followed by MGUS, while relapsed MM presents with the lowest numbers of telomeres and the shortest telomeres. Additional telomere parameters, such as cell cycle distribution profiles (a/c ratio), telomere aggregate numbers, and distances from nuclear centre and also exhibited significance ($p<0.001$) (FIG. 1a).

Within the MGUS and MM patient groups that were studied, are patients whose 3D telomeric profiles indicate the beginning of a new signature that resembles signatures of MM and relapsed MM respectively. Blood and bone marrow shown comparable results opening the future opportunity to base diagnostics and monitoring on blood samples, sparing the patient form invasive bone marrow sampling with potentially adverse effects.

Based on the current preliminary data, the following 3D telomeric criteria that define individual signatures of MGUS and MM and progression within each of the groups are proposed: telomere numbers, telomere sizes, presence of telomeric aggregates, telomeres per nuclear volume, and a/c ratios.

The clinical significance of these findings is the early identification of individuals with high risk of progression. This opens the possibility for better monitoring and early intervention with newer treatments with an acceptable efficacy and low toxicity ratio.

A double blinded preliminary study was conducted with 36 patients, including 20 MM, 12 MGUS and 4 relapsed MM. Using plasma cells from the respective patient groups, 3D nuclear telomeric profiles of these three patient groups were examined. Plasma cells from MM, MGUS, and relapsed MM exhibit specific 3D telomeric signatures as illustrated for two of the four critical 3D nuclear telomere parameters that were measured, namely telomere numbers and relative fluorescent intensities of the measured telomeres (FIG. 1a). Relative fluorescent intensity is proportional to size (Poon et al., 1999), thus the lowest fluorescent intensities represent the smallest telomeres. MM have the highest telomere numbers, followed by MGUS, while relapsed MM presents with lowest number of telomeres and the shortest telomeres. The 3D telomeric profiles obtained with TeloView and TeloScan are comparable (not shown). The significance of these findings shown in Table 1. Additional telomere parameters examined also exhibited significance (see Table 2).

TABLE 1

| Statistical Analysis of relative fluorescent intensity | |
|---|---|
| | MGUS vs. MM vs. relapsed MM |
| Chi-Square | <0.0001 |
| Likelihood Ratio | <0.0001 |
| Chi-Square Mantel-Haenszel Chi-Square | <0.0001 |

Table 1 is a statistical analysis of relative fluorescent intensities. The comparisons are done between MGUS, MM and relapsed MM. There are significant differences in fluorescent intensities between the three groups.

TABLE 2

Statistical analysis of additional 3D nuclear telomere parameters of all samples.

|  | a/c ratio | Telomeric aggregates | Telomeres per nuclear volume |
|---|---|---|---|
| Least squares means | <0.0001 | <0.0001 | <0.0001 |

The analysis indicates that all criteria are significantly different between MM, MGUS and relapsed MM.

The analysis indicates that all criteria are significantly different between MM, MGUS and relapsed MM.

Within the MGUS and MM patient groups that were studied are patients whose 3D telomeric profiles indicate the beginning of a new signature that resembles signatures of MM and relapsed MM respectively. This observation needs validation in this proposed study, since the patient numbers studied so far are too low. In addition, the current patient numbers per group are not equal impacting on the number of statistical tests that can be applied. The best option would be multi-variant analysis. This lack of equal and high enough patient numbers in the proposed study will be corrected and will validate the technology and findings.

Based on the current preliminary data, the following 3D telomeric criteria that define individual signatures of MGUS and MM and progression within each of the groups are proposed: i) telomere numbers, telomere sizes, presence of telomeric aggregates, telomeres per nuclear volume, and a/c ratios (see Tables 1, 2).

If validated, the findings would represent a major breakthrough in the myeloma field since the individual risk of disease progression is currently unknown. If validated, the findings would imply that nuclear telomere remodeling in a subpopulation of MGUS and MM plasma cells enables patient monitoring and patient risk assessment. Treatment design and decisions will be influenced by this study. The 3D telomeric criteria that allow for the objective assessment of MGUS, MM, MGUS/MM transition, and MM/relapsed MM transition will be defined. This will be the read-out of the study and will be its impact on the medical field.

Example 2

In Hodgkin's lymphoma, it was possible to monitor the transition of mono-nucleated Hodgkin to multi nucleated Reed-Sternberg cell (Knecht et al., 2009). Using the present methods patients can be subgrouped into recurrent and non-recurrent at the time of diagnosis. In the same disease, it is demonstrated that recurrent vs. non-recurrent disease can be predicted at diagnosis.

3D Telomere Dynamics in Hodgkin's Lymphoma

Introduction:

Innovative 3D telomere q-FISH allows a mechanistic understanding of the transition from the mononuclear Hodgkin (H) to the multinuclear Reed-Sternberg (RS) cell in Hodgkin's lymphoma (HL) derived cell lines and diagnostic patient biopsies (Leukemia. 2009; 23:565-573). In RS-cells the telomere protecting shelterin complex appears to be disrupted and deregulation of DNA repair mechanisms is observed. These changes occur in both, classical EBV negative and EBV-associated, LMP1 expressing HL (Lab Invest. 2010; 90:611-619). However, it is not known whether the 3D telomere profile at diagnostic biopsy is different in patients entering rapid remission after initiation of standard chemotherapy Adriamycin, Bleomycin, Vinblastine, Dacarbazine (ABVD) compared to that of patients with relapsing or refractory disease. In order to answer this question HL patients entering rapid complete remission were analyzed by 3D telomere q-FISH diagnostic biopsies and were compared to diagnostic biopsies of patients with relapsing or refractory disease.

Patients and Methods:

Rapid remission group (after 1-4 cycles of ABVD): 7 diagnostic biopsies of 7 patients, 19-57 years old, 5 male, 3 LMP1 expressing, 4 nodular sclerosis subtype, 3 mixed cellularity subtype, stages IA, IIA, IIIA×2, IIIB×2, IVA. Relapse group: 7 diagnostic biopsies of 4 patients, 40-77 years old, 2 male, 1 LMP1 expressing, 3 nodular sclerosis subtype, 1 mixed cellularity subtype, stages IIA bulky, IIIB×2, IVB; first remission after 6-8 cycles of ABVD in 3 patients, 1 patient died from progressive disease after 11 months. 3D telomere q-FISH was performed as described (Lab Invest. 2010; 90:611-619) and statistical analysis was performed using nested or two-way analysis of variance.

Tissue Slides:

Archival formalin fixed, paraffin embedded tissue slides (serial sections of 5 μm) from every lymph node biopsy diagnostic for classical Hodgkin's disease were deparaffinized two times for 15 minutes at room temperature in xylene and placed in 100% ethanol. Slides were subsequently rehydrated in a descending gradient of ethanol-water to 30% ethanol, transferred to PBS and used for Hematoxilin-Eosin staining (serial section #1), immunostaining (CD30, serial section #2; LMP1, serial section #3), and quantitative fluorescent in situ hybridization (Q-FISH, serial section #4).

Identification of LMP1 Expressing H- and RS-Cells on Serial Sections with Combined 3D DAPI/Cy-3 Telomere Q-FISH Nuclear Staining:

on serial section #3 lymph node regions with LMP1 expressing H- and RS-cells were identified at a 200× magnification and individual cells further confirmed at a 630× magnification. Subsequently, on serial section #4 the corresponding region was identified at a 200× magnification and the corresponding H- and RS-cells (hence LMP1 expressing) further analyzed for 3D nuclear telomere organization at a 630× magnification.

Immunohistochemistry:

Immunostaining was performed by standard indirect immuno-peroxidase technique using primary monoclonal mouse antibodies anti-CD30 (Ber-H2) and anti-LMP1 (clones CS1-CS4) from DAKO, Glostrup, Denmark, at a dilution of 1:40 and 1:50, respectively. Photomicrographs were performed by using a Zeiss Axioskop 2 microscope with a Polaroid C11806TV camera and Polaroid DMC2 v2.01. software.

Telomere Q-FISH:

The telomere FISH protocol was performed (Chuang et al., 2004; Louis et al., 2005) by using Cy3-labelled peptid nuclei acid (PNA) probes (DAKO). Imaging of interphases after telomere FISH was performed by using Zeiss Axiolmager Z1 with a cooled AxioCam HR B&W, DAPI, Cy3 filters in combination with a Planapo 63×/1.4 oil objective lens. Images were acquired by using AXIOVISION 4.6 (Zeiss) in multichannel mode followed by constraint iterative deconvolution as specified below.

3D Image Acquisition:

30 H-cell interphase nuclei and 30 RS-cell interphase polycaria were analyzed in each lymph node slide. AXIOVISION 4.6 with deconvolution module and rendering module were used. For every fluorochrome, the 3D image consists of a stack of 40 images with a sampling distance of 200 nm along the z and 107 nm in the x and y direction. The constrained iterative algorithm option was used for deconvolution (Schaefer et al., 2001).

3D Image Analysis for Telomeres:

Telomere measurements were done with TeloView (Chuang et al., 2004; Vermolen et al., 2005). By choosing a simple threshold for the telomeres, a binary image is found. Based on that, the center of gravity of intensities is calculated for every object resulting in a set of coordinates (x, y, z) denoted by crosses on the screen. The integrated intensity of each telomere is calculated because it is proportional to the telomere length (Poon et al., 1999).

Segmental Nuclear Volume:

Nuclear volume within one 5 µm thin nuclear section of H-cell or RS-cell is calculated according to the 3D nuclear DAPI staining as previously described (Sarkar et al., 2007). Contrary to whole cell preparations (cells or cell lines), where the nuclei can be visualized with their entire volumes and z-stack analysis along the z-direction over 15 µm allows to calculate the entire nuclear volume, in tissue sections the nuclear volume analysis is limited to 5 µm nuclear segments (as used as a standard for histopathologic diagnosis) along the z-direction. Deparaffinized tissue slides of 10 and 15 µm thickness are technically unsatisfactory for Q-FISH analysis. Thus, the segmental nuclear volume represents about 30-50% of the total nuclear volume of H-cells (nuclear diameter of about 10-15 µm) and about 15-25% of the total nuclear volume of RS-cells (diameter of two up to several nuclei about 20-40 µm).

Segmental Telomere Number:

Segmental telomere number is the sum of all very short, short, mid-sized and large telomeres and aggregates identified within one 5 µm thin nuclear section of an H-cell or RS-cell.

Segmental Telomere Intensity:

Segmental telomere intensity is the sum of intensities of all very short, short, mid-sized and large telomeres and aggregates identified within one 5 µm thin nuclear section of a H-cell or RS-cell (viz. Σ2×15 000 units>Σ7×4000 units).

Mean Telomere Intensity:

Mean telomere relative fluorescent intensity (length) of all telomeres within a given segmental volume.

Telomere Length:

Telomeres with a relative fluorescent intensity (x-axis) ranging from 0-5,000 units are classified as very short, with an intensity ranging from 5,000-15,000 units as short, with an intensity from 15,000-30,000 units as mid-sized, and with an intensity >30,000 units as large.

Telomere Aggregates:

Telomere aggregates are defined as clusters of telomeres that are found in close association and cannot be further resolved as separate entities at an optical resolution limit of 200 nm (Mai and Garini, 2006).

Statistical Analysis:

For each case, normally distributed parameters are compared between the two types of cells using nested ANOVA or two-way ANOVA. Multiple comparisons using the least square means tests followed where interaction effects between two factors were found to be significant. Other parameters that were not normally distributed were compared using a nonparametric Wilcoxon rank sum test. Significance level were set at p=0.05. Analyses were done using SAS v9.1 programs.

Results:

Bi- or multinuclear RS-cells of all patients from both groups showed significant increase of very short telomeres and telomere aggregates when compared to the mononuclear precursor H-cells. However, most importantly, all diagnostic biopsies of the relapse group contained a very high percentage of very small telomeres, including so-called "t-stumps", in both H-cells (76.8±11.8%) and RS-cells (87.9±7.3%). Compared to the percentage of very small telomeres identified in both, H-cells (33.7±9.4%) and RS-cells (54.6±15.0%) of the rapid remission group, this increase is highly significant (p<0.001). Moreover, analogous findings are observed for the number of telomere aggregates. In the relapse group the average numbers of telomere aggregates per cell were 4.3±2.4 aggregates per H-cell and 5.4±3.0 aggregates per RS-cell, compared to 1.2±0.7 aggregates per H-cell and 3.3±1.1 aggregates per RS-cell in the rapid remission group.

Discussion:

The 3D nuclear telomere organization of H- and RS-cells in diagnostic biopsies of relapsing or refractory HL is characterized by both H- and RS-cells with abundant "t-stumps" and numerous telomere aggregates. Very short telomeres, including "t-stumps", and telomere aggregates, both, are characteristics of aggressiveness in cancer biology (Mol. Cell. 2007; 28:315-327; J Cell Biochem. 2010; 109: 1095-1102). Thus, H- and RS-cells of refractory or relapsing HL show significant differences in the 3D telomere dynamics already at first, diagnostic biopsy when compared to H- and RS-cells of HL entering rapid remissions.

Figure 3:
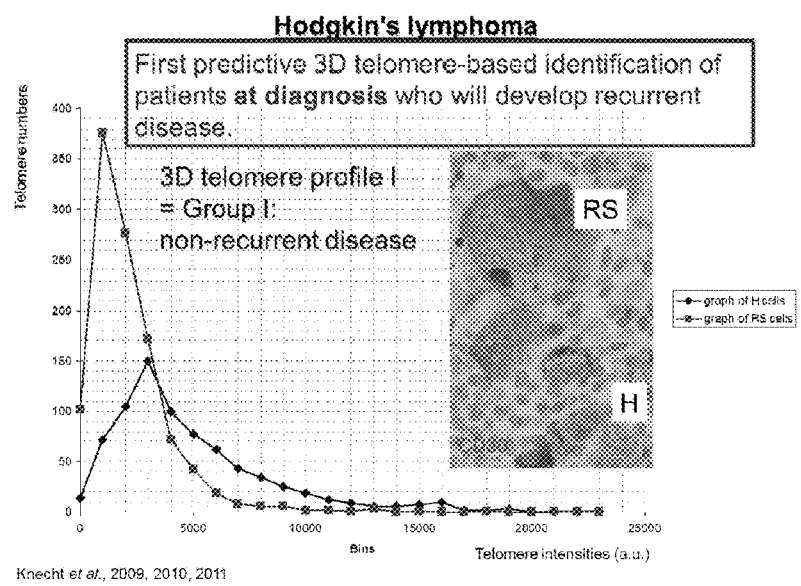
FIG. 3. 3D telomere profile in Hodgkin's lymphoma in patients with non-recurrent disease FIG. 4. 3D telomere profile in Hodgkin's lymphoma in patients who relapse.

FIG. 3 shows the 3D telomere profile in H cells and RS cells of patients with non-recurrent disease.

Figure 4:
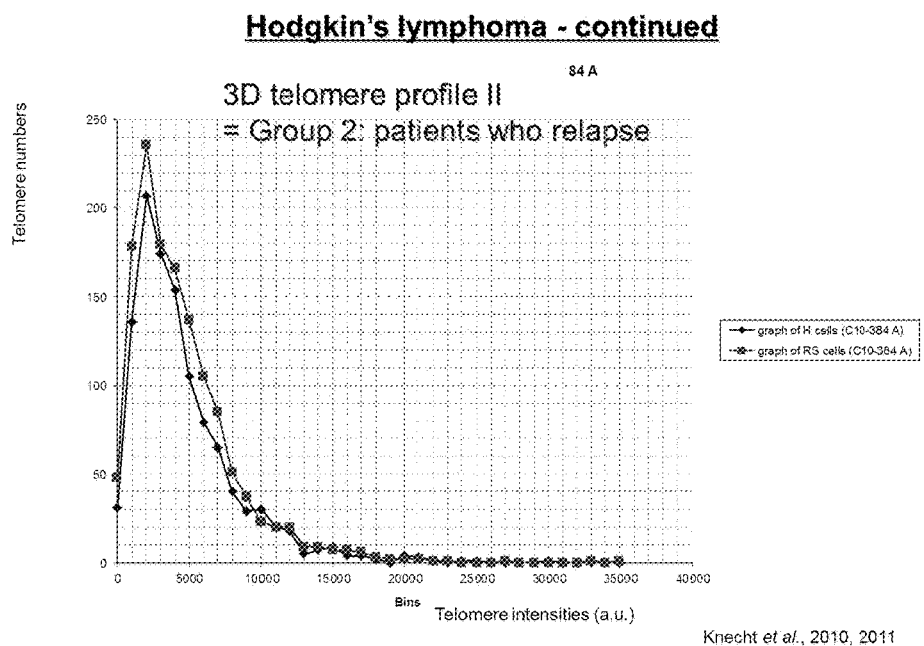

FIG. 4. Shows the 3D telomere profile in H cells and RS cells of patients who relapse.

Example 3

Myelodysplastic Syndromes (MDS)

The evolution of MDS to AML/MDS (acute myeloid leukemia) is a hallmark of these syndromes and is characterized by genomic instability.

Rational

To improve the treatment strategies of MDS, the causal evolution of MDS to AML should be better understood. This transition is characterized by genomic instability. Nuclear telomere architecture might be the causal event causing this genomic instability. A mechanistic and molecular links between nuclear telomeres architecture and genomic instability in MDS and in the transition of MDS to AML might exist and should be retrieved. This is assessed according to the following.

Nuclear Architecture

The nuclear telomeric architecture in patients bearing MDS or AML/MDS is determined. Telomere 3D-FISH is performed in bone marrow smear slides from patients bearing MDS and in bone marrow smear slides from patients bearing AML/MDS.

The results of both are compared in order to depict the nuclear telomeres reorganisation of the transition from MDS to AML/MDS.

Further, the results of telomeres 3D-FISH from each patient followed from MDS to AML/MDS are compared.

The nuclear telomeric architecture in haematopoietic stem cell (HSC) extracted from bone marrow of these patients bearing MDS or AML is determined.

Haematopoietic stem cells (HSCs) from bone marrow of MDS and AML/MDS patients are isolated and telomeres 3D-FISH is performed on HSCs from bone marrow of these patients.

The stem cell results are compared to the bone marrow smears.

Methodology

Sampling:

Bone marrow samples will be taken from patients followed at the Medical Oncology & Haematology in the Health Sciences Centre Winnipeg (HSC), at the Centres Hospitaliers Universitaires (CHUs) of Senegal, and from the Banque des cellules leucémiques du Québec (BCLQ). After sampling, smear slides and separation of HSCs from the leukemic cells will be performed. Then, cell cultures will be performed with the HSCs and with the leukemic cells. Around 60 patients will be recruited in the goal to get at least 5 patients in each of type of MDS or AML/MDS.

Determining the Nuclear Telomeres Architecture in Patients Bearing Myelodysplastic Syndrome or Acute Leukemia The exact nuclear telomeres architectures in different types of MDS and in AML/MDS will be determined. The 3D nuclear telomeric architecture, which includes telomere aggregates, telomere position, and telomere length.

Experimental Design:

Telomere 3D-QFISH in bone marrow smear slides will be performed using the current protocol[12], and analyzed with TeloScan and TeloView programs[15]. Patients bearing MDS and AML/MDS will also be used. The results of the different patients, and from patients sampled at MDS versus at AML/MDS will be compared.

Expected Results and Discussion:

These above experiments will allow determination of specific telomeres organisation in MDS and AML/MDS. It is expected to get differences in telomere profiles in the different MDS and AML/MDS. Also, it is hoped that by analysing the differences in nuclear telomeres architecture between MDS and AML/MDS the nuclear telomeres evolution of MDS to AML/MDS will be further understood.

Determining the Nuclear Telomeric Architecture in Haematopoietic Stem Cell Extracted from Bone Marrow of these Patients Bearing Myelodysplastic Syndrome or Acute Leukemia To understand better the transformation of haematopoietic progenitor cells to myelodysplastic cells and how MDS occur from these stem cells, the exact nuclear telomeres architecture from stem cells present in the bone marrow samples will be determined.

Experimental Design:

Haematopoietic stem cells will be extracted from bone marrow of these patients using CD133 Microbeat kit of Mitelnyi Biotech. Half of these cells will be cultured according the specific protocol to culture haematopoietic stem cells in the goal to increase the number of stem cells, and the remaining half smeared on a slide to perform 3D-QFISH. The results of leukemic cells will be compared versus HSCs of each patient, and between all different types of MDS, and AML/MDS.

Expected Results and Discussion:

The nuclear telomere architecture differences between HSCs and leukemic cells from each patient will be known. The exact telomeres architecture of HSC in different types of MDS and in AML/MDS will be determined. Then, it will be understood how nuclear telomeres architecture in HSCs reorganize to give rise to myelodysplastic cells, and also how myelodysplastic cells change their nuclear architecture to become acute leukemic cells. Determining the copy number variation of DNA extracted from bone marrow of patients by aCGH and to compare with the specific nuclear telomeric architecture.

Figure 2:
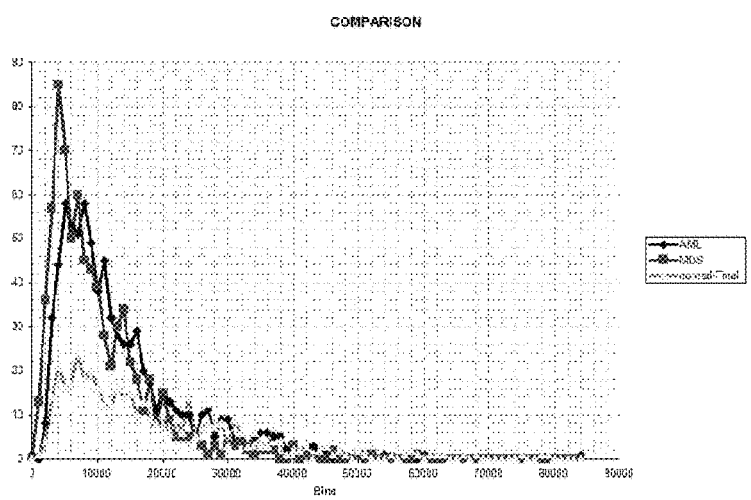
FIG. 2. Telomere numbers in AML, MDS and normal cells. Overall 3D distribution of the telomeres: Normal patient without telomeric aggregates; MDS patient starts to show genomic instability by increasing the number of telomeres and by generating telomeric aggregates; AML patient have more genomic instability by generating more telomeric aggregates, this decreasing the number of telomeres.

FIG. 2 shows that MDS and AML telomere parameters differ from normal cells.

Example 4

The 3D nuclear telomeric organization of plasma cells collected from patients who have been positively diagnosed with either MGUS, MM or relapsed MM is quantitatively analysed. The telomeres will be visualized in the cells using 3D fluorescence in-situ hybridization, coupled with 3D imaging and reconstruction. This is followed by quantitative analysis, using semi-automated TeloView™ and fully automated TeloScan. Preliminary studies have demonstrated specific 3D nuclear telomeric signatures for MGUS, MM and relapsed MM conditions.

Based on the preliminary data, the 3D nuclear organization of telomeres predicts whether a patient with plasma cell disease has MGUS or MM.

The 3D nuclear organization of telomeres predicts disease progression from MGUS to MM.

The 3D nuclear organization of telomeres predicts the transition of MM to relapsed MM.

Additional samples will be assessed to:
a) examine the 3D nuclear telomeric profiles of plasma cells from patients with MGUS;
b) examine the 3D nuclear telomeric profiles of plasma cells from patients with MM;
c) identify the 3D nuclear telomeric profiles of plasma cells from patients at MGUS/MM disease transition;
d) identify the 3D nuclear telomeric profiles of plasma cells from patients at MM/relapse MM transition.

MM is defined by serum M-protein levels >3 g/dL, bone marrow plasma cells >10%, and end organ damage (lytic bone lesions, anemia, hypercalcemia, renal failure) (Mailankody et al., 2010). MM will progress to relapsed MM. The causes for this progression remain unknown.

MM has a precursor lesion, monoclonal gammopathy of undetermined significance (MGUS). MGUS is defined according to the International Myeloma Working Group (IMWG, 2010; Kyle et al., 2010) as a disease having i) serum monoclonal protein under 3 g/dL, ii) clonal bone marrow plasma cells under 10%, and iii) no end-organ lesions (including hypercalcemia, renal insufficiency, anemia, and bone lesions) (Landgren, 2010).

MGUS fall in two distinct biological entities, lymphoid MGUS, that can progress to Waldenström's macroglobulinemia, lymphoma, or other lymphoproliferative disorders (Kyle et al, 2003), and plasma-cell MGUS that can progress to MM (Landgren 2010, Mailankody et al, 2010). Our focus is on the latter type of MGUS.

The rate of transformation from MGUS to MM is 1.2% per annum (Kyle and Rajkumar, 2007). The cause of progression to MM is unknown but postulates include secondary genetic changes such as N-ras and K-ras mutations (Liu et al., 1996), Myc overexpression, altered cytokine profiles and an increase in bone marrow neo-vascularisation measured by median microvascular density (Rajkumar et al., 2002, Mailankody et al., 2010).

Although clinical markers of progression have been identified, it is impossible to determine the individual risk for progression (Mailankody et al., 2010, Landgren, 2010). Risk factors have been proposed (Mayo Clinic model and Spanish Study Group model). The Mayo Clinic model is based on protein levels (non-IgG isotype, M protein concentration >1.5 g/dL, and an abnormal serum free light chain ratio) (Rajkumar, 2005).

In the Mayo Clinic model, patients with all three risk factors have a cumulative risk of progression at 10 years of 84%. Having two risk factors place them at 65%, one risk factor at 50% cumulative risk of progression at 10 years (Mailankody et al., 2010). In the Spanish model, flow cytometry is used to detect normal vs. aberrant plasma cells (CD138 expression and intensive CD38 in normal plasma cells, while they detect CD138 expression and low CD38 levels in aberrant plasma cells, expression of CD56, absence of CD19 and CD45) (for review, see Mailankody et al., 2010) and to define the cumulative risk of progression. For example, over a period of 5 years, it is 2%, 10% and 46% respectively with no, one or two risk factors.

Better markers are needed to predict individual risk of development of MM.

3D Telomere Association with Progression.

The 3D organization of telomeres is altered in cancer cells (Chuang et al., 2004; Mai and Garini, 2006). This basic finding led to an understanding of genetic changes in early cancer cells and proved that telomere organization is key to genome stability vs. instability (Mai and Garini, 2006; Mai and Garini, 2005; Louis et al., 2005): It has been demonstrated that each nucleus has a specific telomeric signature that defines it as normal or aberrant. Four criteria define this difference; 1) nuclear telomere distribution, 2) the presence/absence of telomere aggregate(s), (Telomere aggregates are telomeres found in clusters that at an optical resolution limit of 200 nm cannot be further resolved (Vermolen et al., 2005; Mai and Garini, 2006; Mai, 2010). Telomeric aggregates are not seen in normal cells), 3) telomere numbers per cell, and 4) telomere sizes (Mai, 2010). Additional criteria include a/c ratios (a/c ratios define the nuclear positions of telomeres. The a/c ratios are characteristic for specific cell cycle phases (Vermolen et al., 2005)) and nuclear volumes.

Measurements of 3D Nuclear Telomere Organization.

To quantify the 3D nuclear organization of telomeres and to measure the above criteria defining the 3D nuclear organization, a semi-automated program was developed, TeloView™ (Vermolen et al., 2005; Gonzalez-Suarez et al., 2009). To allow for high throughput analyses as required for future clinical applications, an automated version of TeloView™ was next developed, designated TeloScan (Gadji et al., 2010; Klewes et al., 2011). TeloScan is able to examine thousands of cells in an unsupervised manner. In a proof-of-principle study, it has been shown that 1 cancer cell is identified among 1000 normal cells (p=0.001) and at considerable speed [10,000-15,000 cells per hour] (Klewes et al., 2011). This finding has implications for the work proposed in this study: It will allow the identification of subpopulations easily should they be present among plasma cells from MGUS and MM patients. In addition, normal plasma cells and aberrant ones will be easily distinguished due to the organizational difference in their 3D telomeric profiles. This latter feature is particularly important for MGUS where MGUS plasma cells are in low abundance.

As mentioned, preliminary data on small groups of patients (Example 1) was obtained.

These data suggest that: 1) the technology is capable of differentiating between MGUS and MM; 2) using the 3D nuclear telomere-guided cancer cell analysis, it detects subpopulations in plasma cells of some MGUS patients; 3) it identifies different 3D telomeric profiles between MM and MM relapse (FIG. 1a, and Example 1).

The findings in Example 1 are assessed in larger patient cohorts. To this end, the preliminary observations for MGUS will be first validated and it will be determined whether the observations hold true with larger patient cohorts. Similarly, more cases of MM will be examined to confirm a clear-cut difference between MGUS and MM based on the 3D telomeric signatures of each patient group. As some MGUS patients showed MGUS as well as beginning of MM signatures, this finding will be validated with larger patient cohorts. Finally, the disease progression from MM to relapsed MM based on our 3D telomeric signatures will be validated. A definition of criteria for the individual assessment of cancer progression in MM will be provided.

Patient monitoring based on 3D telomeric signatures of plasma cells will add a new parameter to the Mayo Clinic Model or Spanish Group Model of risk assessment for disease progression in MM. The technology is capable of detecting sub-populations indicative of tumor progression in other cancers, including glioblastoma (Gadji et al., 2010), in Hodgkin's lymphoma (Knecht et al., 2010), and in our preliminary data on MM (see Example 1).

3D Telomere Technology.

Four main criteria were employed to define the differences in 3D nuclear telomeric organization of normal and tumor cells. These are; telomere numbers per nucleus, telomere sizes, nuclear telomere distribution, and the presence of telomeric aggregates. Telomeric aggregates are clusters of telomeres that cannot further be separated into individual telomeric signals at an optical resolution of 200 nm. Telomeric aggregates are not present in normal cells (Mai, 2010; Klewes et al., 2011).

Overall Strategy and Ethics.

Plasma cells from bone marrow and/or blood are obtained from patients with MM or MGUS upon informed consent. The samples are given a laboratory number before they arrive in the research laboratory. The information linking the specimen number to the human subject is not available to the investigator. With respect to inclusion of both genders, it is anticipated that roughly an equal number of male and female subjects will consent to donating samples, and this is reflected in our preliminary data set. Minorities in the sample population will reflect the general distribution of the disease in the study cohort. No children will be included because the disease studied is non-existent in children. The research protocols and the consent form have been scrutinized and approved by the University of Manitoba Health Research Ethics Board (approval number H2010:170, approval date: May 20, 2010). This type of research is considered minimal risk (no risk) to the human subjects.

Statistical Consideration.

The size of the study population needed for the study was determined by a bio-statistician. With 32 subjects per group (MM, relapsed MM and MGUS respectively; a total of 96 subjects) and 30 cells for each subject (using TeloView analysis, Vermolen et al., 2005), there will be 80% power to find a significant effect (two-tailed alpha=0.05) with respect to critical criteria for the distinction of patient groups and subpopulation. This population size (comprising the same 96 participants) is sufficient also to perform a multivariate analysis to further discriminate between subpopulations. Moreover, the cell samples from the same population will be sufficient for another set of study using TeloScan analysis (Gadji et al., 2010, Klewes et al., 2011), to compare and validate a fully automated analysis program against a semi-automated one, although in this analysis scan 500 cells per patient will be scanned.

Methodology and Analysis.

Cells from blood and/or bone marrow will be 3D fixed and placed onto a microscope slide (Louis et al., 2005). 3D quantitative fluorescent in situ hybridization (Q-FISH) will be performed as published (Louis et al., 2005) using a Cy3-labelled peptide nucleic acid (PNA) probe (DAKO).

The nuclei will be counterstained with 4'-6-diamidino-2-phenylindole (DAPI). Imaging and analysis will utilize the programs, TeloView™ (Vermolen et al., 2005; Gonzalez-Suarez, 2009) and TeloScan (Gadji et al., 2010; Klewes et al., 2011). For TeloView™ analysis (Vermolen et al., 2005; Gonzalez-Suarez, 2009), imaging of nuclei is performed by using Zeiss AxioImager Z2 with a cooled AxioCam HR B&W, DAPI, Cy3 filters in combination with a Planapo 63×/1.4 oil objective lens. Images are acquired by using AXIOVISION 4.8 (Zeiss) in multichannel mode followed by constrained iterative deconvolution (Schaefer et al., 2001). For every fluorochrome, image stacks are acquired with a sampling distance of 200 nm along the z and 107 nm in the xy direction. TeloScan, the automated version of TeloView, is performed on a scanning platform, the SpotScan system (Applied Spectral Imaging, Migdal HaEmek, Israel). The system uses an automated Olympus BX61 microscope (Olympus, Center Valley, Pa.) equipped with filters for DAPI and Cy3. Using images of 10 focal planes 0.7 µm apart, TeloScan will be used to scan in telomeres in 3D and store all 3D data. As published, we are able to scan 10,000-15,000 cells per hour in 3D (Klewes et al., 2011).

A super resolution 3D imaging system that enables post-Abbe resolution of 20 nm can alternatively be used although conventional 3D microscopy is sufficient. For example, a beta-version of the instrument has been used to obtained super resolution 3D data related to chromatin, chromosomes and telomeres (Mai, 2010, Klonisch et al., 2010; Guffei et al., 2010).

Example 5

Multiple myeloma (MM) is recognized as the second most common cancer of the blood. It is a malignant disorder of plasma cells and commonly affects adults past the age of 50 (1). Although risk factors have been established, it is currently not possible to assess the individual risk to cancer progression. Moreover, the causes of disease progression from its precursor condition, monoclonal gammopathy of undetermined significance (MGUS), to full-blown MM and its progression to relapsed MM remain elusive (2, 3). Previous studies have been on the three-dimensional (3D) nuclear organization of telomeres and found that normal and tumour cells display significant differences in their nuclear organization. These differences were objectively quantified with two software programs, TeloView (4-8) and TeloScan (9). A new double blinded preliminary study with 78 patients, including 40 MM, 30 MGUS and 8 relapsed MM I snow reported. Using blood- and bone marrow-derived plasma cells from the respective patient groups, 3D nuclear telomeric profiles of the above patients have been examined. Plasma cells from MM, MGUS and relapsed MM exhibit specific 3D telomeric signatures. MM has the highest telomere numbers, followed by MGUS, while relapsed MM presents with the lowest numbers of telomeres and the shortest telomeres. Additional telomere parameters, such as cell cycle distribution profiles (a/c ratio), telomere aggregate numbers, distances from nuclear centre also exhibited significance ($p<0.001$).

Within the MGUS and MM patient groups studied are patients whose 3D telomeric profiles indicate the beginning of a new signature that resembles signatures of MM and relapsed MM, respectively. Blood and bone marrow gave comparable results, opening an opportunity to base diagnostics and monitoring on blood samples, sparing the patient form invasive bone marrow sampling with potentially adverse effects. Based on the current preliminary data, it is proposed the following 3D telomeric criteria that define individual signatures of MGUS and MM and progression within each of the groups: telomere numbers, telomere sizes, presence of telomeric aggregates, telomeres per nuclear volume, and a/c ratios. The clinical significance of these findings is the early identification of individuals with high risk of progression.

This opens the possibility for better monitoring and early intervention with newer treatments with an acceptable efficacy and low toxicity ratio.

Methods

Telomeres of isolated white blood cells from bone marrow aspirates and blood samples were hybridized with Cy3-labelled PNA (peptide-nucleic-acid) telomere probes (4, 6).

Image acquisition of plasma cell interphases after FISH was performed by using a Zeiss AxioImager Z1 (for TeloView analysis (7), For scanning purposes the microscope was equipped with a slide stage (Märzhäuser, Germany).

Imaging conditions: Image acquisition and analysis were performed using semi- and fully automated schemes at 63× oil and 40×, respectively.

Semi-automated image acquisition according to (7).

Automated image acquisition according to (9).

Software for data acquisition and analysis: AxioVision and TeloView were used for the semi-automated experiments, TeloScan (ASI).

Results

Figure 1B:
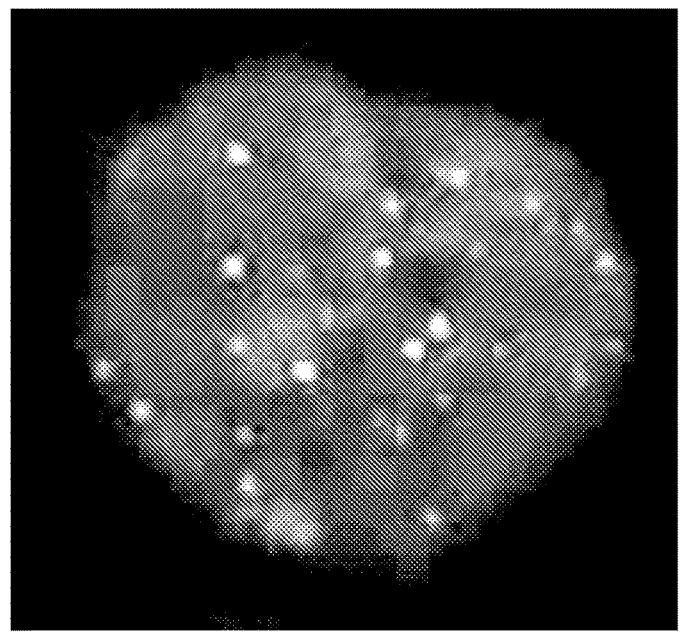

FIG. 1b shows an image of nucleus in 2D. The telomeres are hybridized with Cy3 conjugated PNA probes. The nuclei were counter stained with DAPI.

Figure 1C:
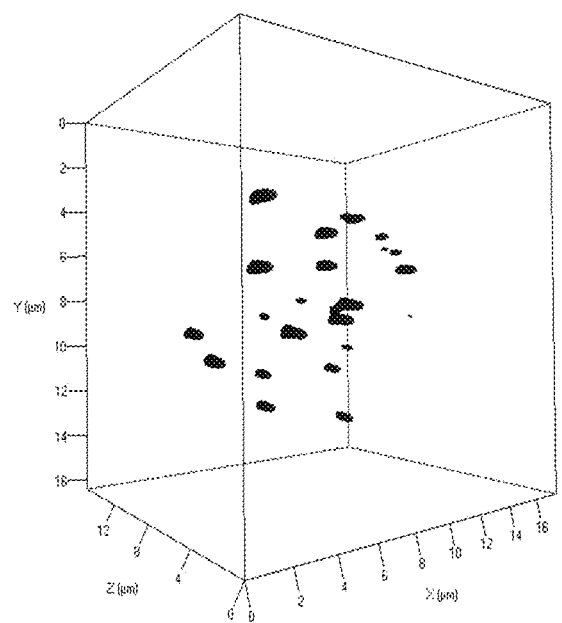

FIG. 1c. shows an image of the same nucleus in 3D. The telomeres are shown in their 3D distribution within the nucleus.

Figure 1D:
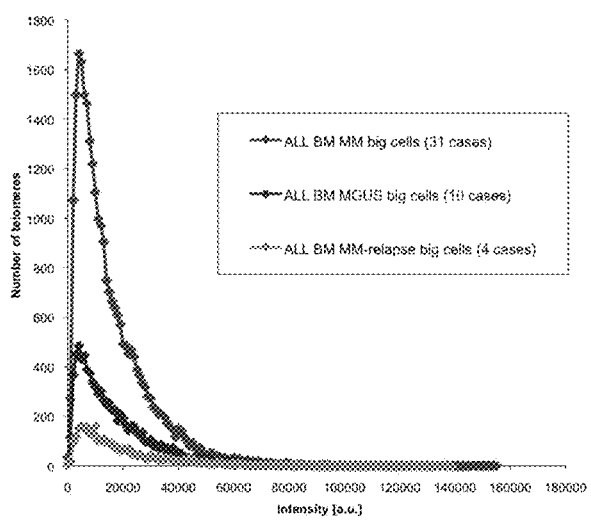

FIG. 1d. shows semi-automated analysis of telomeric signals in BM samples: The intensities in MGUS, MM, and MM relapse show distinct patterns. Telomere length in patients diagnosed with MGUS is longer than in patients diagnosed with MM or those going into relapse. Patients going into relapse show the lowest number of telomere signals, followed by MGUS and MM, indicating aneuploidy as well as telomere shortening/loss during MM progression.

Figure 1E:
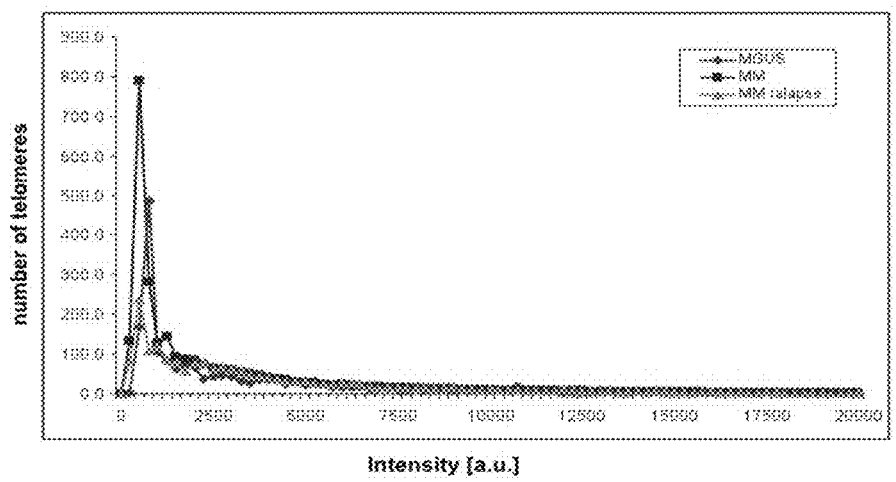

FIG. 1e. shows automated analysis of telomeric signals in BM samples: The intensities in MGUS, MM, and MM relapse show the same distinct patterns as seen in the semi-automated analysis.

Figure 1F:
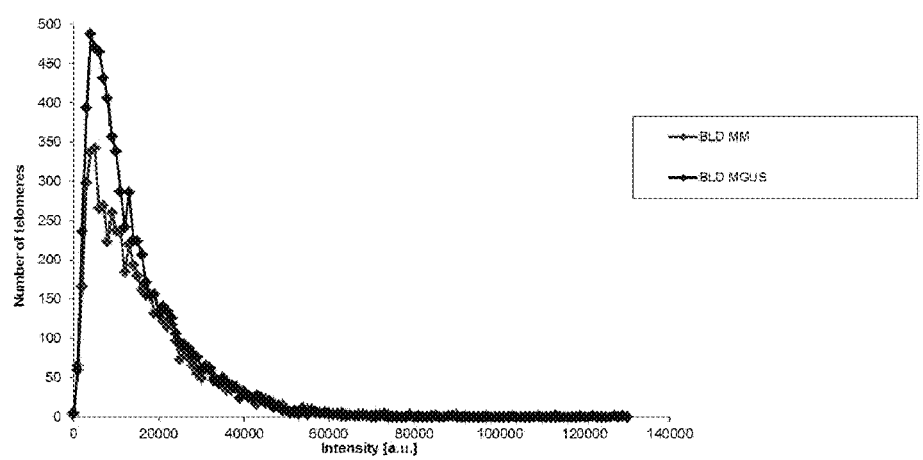

FIG. 1f. shows semi-automated analysis of telomeric signals in blood samples: The intensities in MGUS and MM show distinct patterns as seen in the bone marrow. Telomere length in patients diagnosed with MGUS is longer than in patients diagnosed with MM, indicating aneuploidy as well as telomere shortening/loss during MM progression. The inset shows the telomere distribution in 3D.

Figure 1G:
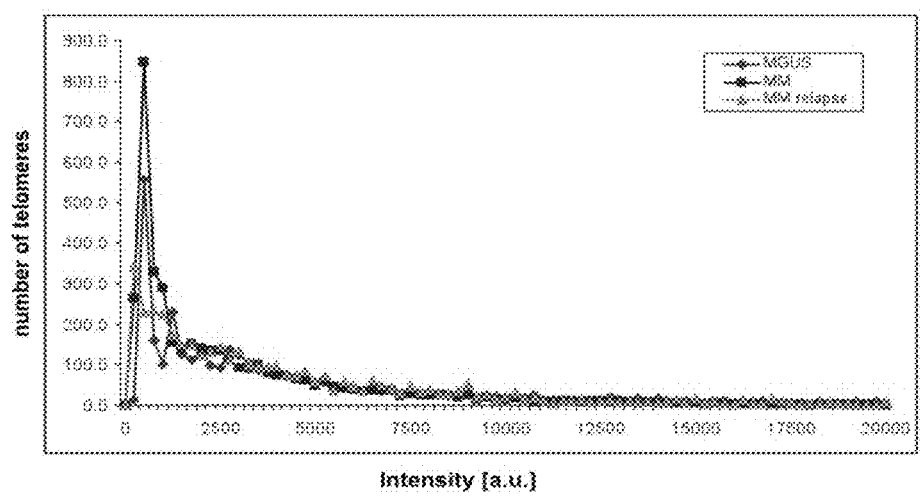

FIG. 1g. shows automated analysis of telomeric signals in peripheral blood: The intensities in MGUS, MM, and MM relapse show the same distinct patterns as seen in the semi-automated analysis. The inset shows the user interphase of TeloView.

Discussion:

In this study, significant differences of the 3D nuclear architecture in samples of patients diagnosed with MGUS, MM, and patients with MM relapse are shown.

The examined parameters include a/c ratio, the presence of telomeric aggregates, and the number of telomeres per nuclear volume (7, 9).

Preliminary data suggest that the automation of TeloView, TeloScan, is able to detect differences with respect to the signal intensities and telomere numbers between these groups.

Both TeloView and TeloScan identify similar 3D telomeric profiles in blood samples as well as in bone marrow aspirates.

Conclusion:

In this study, changes of the 3D nuclear telomeric signatures in interphase nuclei based on three-dimensional fluorescent in situ hybridization (3D-FISH) of MGUS-, MM- and MM-relapse samples are demonstrated.

The fully automated system allows a high throughput of samples, while the data output includes numbers of telomeric aggregates, telomere numbers, and telomere signal intensities, that are proportional to sizes.

3D telomere signatures allow for the identification of patients diagnosed with MGUS, MM, and MM-relapse. The signatures are very similar for blood samples and bone marrow aspirates.

REFERENCES FOR CITATIONS IN EXAMPLE 5

1. Kenneth C. et al., Annu. Rev. Pathol. Mech. Dis. 2011. 6:249-74
2. Landgren O, JAMA. 2010; 304(21):2397-2404
3. Kyle R A et al., Leukemia (2010) 24, 1121-1127
4. Chuang T C et al., BMC Biol. 2004 Jun. 3; 2:12.
5. Vermolen B J et al., Cytometry A. 2005 October; 67(2): 144-50
6. Louis S F et al., Proc Natl Acad Sci USA. 2005 Jul. 5; 102(27):9613-8
7. Mai S, Garini Y. Cell Cycle. 2005 October; 4(10):1 327-31
8. Lacoste S, et al., Oncogene. 2010, 29, 503-15
9. Klewes et al., Cytometry Part A, 2010, 79A, 159-66, Example 6

The 3D telomeric signatures differ between normal and cancer cells. 3D telomere Q-FISH allows for a mechanistic understanding of the transition from the mononuclear Hodgkin (H) cell to the multinuclear Reed-Sternberg (RS) cell in EBV negative and EBV-associated, LMP1 expressing classical Hodgkin's lymphoma (HL). In the current study, 3D telomere Q-FISH on 11 diagnostic biopsies of 7 patients with relapsing or refractory HL (5 patients died from refractory disease, 1 is in remission after autologous bone marrow transplantation and 1 is alive with progressing disease) were used and compared with diagnostic biopsies from 11 patients entering rapid/sustained remission (mean 30 months). H-cells and RS-cells from patients with refractory/relapsing disease contained a significantly higher percentage of very small telomeres (p<0.0001) and telomeric aggregates (p<0.0001) compared with patients entering sustained remission. Moreover, the H-cells of refractory patients contained as many aggregates and more very small telomeres (p<0.0001) as the end-stage RS-cells of patients entering rapid and sustained remission. Since high numbers of very short telomeres and telomere aggregates are characteristics of aggressiveness in cancers, 3D telomere Q-FISH allows one to identify these highly aggressive H-cells at the first diagnostic biopsy and offers the possibility to optimize initial treatment.

Introduction

Telomeres are the nucleoprotein complexes at the ends of chromosomes. Telomeric DNA consists of multiple double-stranded TTAGGG repeats and ends in a single-stranded overhang of the G rich 3' strand.[1] Furthermore, a number of specific proteins, either binding telomeric DNA directly or being associated to telomeric chromatin, called Shelterin complex, are found on telomeres.[2,3] Many cancer cells display chromosomal aberrations that are the direct result of telomere dysfunction[4,5] and the 3D organization of telomeres is altered in cancer cells.[6,7]

This basic finding led to an advanced understanding of genetic changes in early cancer cells and proved that telomere organization is key to genome stability vs. instability.[8,9] It has been shown that each nucleus has a specific telomeric signature that defines it as normal or aberrant. Four criteria define this difference; i) nuclear telomere distribution, ii) the presence/absence of telomere aggregate(s), iii) telomere numbers per cell, and iv) telomere sizes.[10,11]

The bi- or multinuclear Reed-Sternberg cells (RS-cells), the diagnostic element of Hodgkin's lymphoma (HL), derive from mononuclear precursors called Hodgkin cells (H-cell), via endo-reduplication and have a limited capacity to divide further.[12-14] H-cells are derived from germinal center B-cells[15] and small circulating clonotypic B-cells, putative precursors of H-cells, have been identified by flow cytometry.[16] H- and RS-cell show high telomerase activity[17,18] and express abundant telomerase RNA.[19]

Using a three-dimensional quantitative fluorescent in situ hybridization technique to visualize telomere in cultured cells and biopsies (3D telomere Q-FISH)[8], the transition from mononuclear H- to multinuclear RS-cells at the molecular level was characterized.[20-22] It was shown that RS-cells are true end-stage tumour cells in both, classical Epstein-Barr virus (EBV)-negative and EBV-positive HL. The number of nuclei in these RS-cells correlates closely with the 3D organization of telomeres and further nuclear divisions are hampered by sustained telomere loss, shortening and telomere aggregation.

The increase of very short telomeres and aggregates in these RS-cells compared to their mononuclear precursor H-cells is highly significant (p<0.0001). Such RS-cells contain telomere/DNA-poor "ghost" nuclei and giant "zebra" chromosomes including up to 7 different chromosomal partners as revealed by spectral karyotyping (SKY). These molecular changes are the result of multiple breakage-bridge-fusion (BBF)-cycles.[22] Since such 3D characteristics are not identifiable by routine histology examination, it was hypothesized that H- and RS-cells of primary refractory or relapsing HL might differ in their 3D telomere dynamics from H- and RS-cells of HL entering rapid and sustained remission. To answer this issue 11 diagnostic lymph node biopsies from patients entering rapid remission were analyzed and compared to 11 lymph node biopsies diagnostic for relapse or disease progression in 7 patients. The results show significant differences in 3D telomere dynamics of relapsing/progressing disease.

Material and Methods

Study Design

Until January 2011, 33 patients entered the study; 25 had the diagnosis of classical HL, 3 of LPNHL (lymphocyte predominant nodular Hodgkin's lymphoma), 3 of EBV-associated angioimmunoblastic T-cell lymphoma (TAIL, LMP1+), one of T-cell anaplastic large cell lymphoma ALK+, and one of EBV positive large B-cell lymphoma.

In order to get statistically correct analysis in each case of classical HL, at least 30 H-cells and 30 RS-cells have to be analyzed by 3D telomere Q-FISH. Since sometimes less than 30 H- or RS-cells are present on a diagnostic slide, not all analyzed cases are available for statistical analysis.

Unequivocal statistical analysis could be performed on 22 diagnostic biopsies of 18 out of 25 patients with diagnosis of classical HL.

Clinical Response Definition

Remission from HL was defined by fluorodeoxyglucose (FDG) positron emission tomography-computed tomography (PET/CT) scan (and bone marrow biopsy for patients with initial bone marrow involvement). Activity of involved sites had to disappear completely by follow-up FDG-PET/CT-scan when compared to the FDGPET/CT-scan performed at diagnostic work-up. In patients with initial bone marrow involvement, follow up bone marrow biopsy had to get cleared for CD30+ tumour cells. Follow-up FDG-PET/CT-scan was performed at the treating physician's discretion but at least after the fourth cycle of chemotherapy. Patients in remission had at least 2 additional FDG-PET/CT-scans within the first year after completion of treatment.

Tissue Slides:

Archival formalin fixed, paraffin embedded tissue slides (serial sections of 5 μm) from every lymph node biopsy diagnostic for classical Hodgkin's disease were deparaffinised two times for 15 minutes at room temperature in xylene and rehydrated in reverse-graded series of ethanol (the incubations are 100%, 75%, 70%, 50% for 10 minutes each); the slides were then dipped briefly in ddH$_2$O and then transferred into phosphate buffered saline (PBS) and used for Hematoxilin-Eosin staining (serial section #1), immunostaining (CD30, serial section #2; LMP1, serial section #3), and quantitative fluorescent in situ hybridization (Q-FISH, serial section #4).

Identification of LMP1 Expressing H- and RS-Cells on Serial Sections with Combined 3D DAPI/Cy-3 Telomere Q-FISH Nuclear Staining:

on serial section #3 lymph node regions with LMP1 expressing H- and RS-cells were identified at a 200× magnification and individual cells further confirmed at a 630× magnification. Subsequently, on serial section #4 the corresponding region was identified at a 200× magnification and the corresponding H- and RS-cells (hence LMP1 expressing) further analyzed for 3D nuclear telomere organization at a 630× magnification.

Immunohistochemistry:

Immunostaining was performed by standard indirect immunoperoxidase technique using primary monoclonal mouse antibodies anti-CD30 (Ber-H2) and anti-LMP1 (clones CS1-CS4) from DAKO, Glostrup, Denmark, at a dilution of 1:40 and 1:50, respectively. Photomicrographs were performed by using a Zeiss Axioskop 2 microscope with a Polaroid C11806TV camera and Polaroid DMC2 v2.01. software.

Telomere Q-FISH:

The telomere FISH protocol was performed[6,8] by using Cy3-labelled peptide nucleic acid (PNA) probes (DAKO). Imaging of interphases after telomere FISH was performed by using Zeiss Axiolmager Z1 with a cooled AxioCam HR B&W, DAPI, Cy3 filters in combination with a Planapo 63×/1.4 oil objective lens. Images were acquired by using AXIOVISION 4.6 and 4.8 (Zeiss) in multichannel mode followed by constraint iterative deconvolution as specified below.

3D Image Acquisition:

At least 30 H-cell interphase nuclei and 30 RS-cell interphase polycaria were analyzed in each lymph node slide. AXIOVISION 4.6 and 4.8 with deconvolution module and rendering module were used. For every fluorochrome, the 3D image consists of a stack of 40 images with a sampling distance of 200 nm along the z and 107 nm in the x and y direction. The constraint iterative algorithm option was used for deconvolution.[23]

3D Image Analysis for Telomeres:

Telomere measurements were done with TeloView.[6,24] By choosing a simple threshold for the telomeres, a binary image is found. Based on that, the center of gravity of intensities is calculated for every object resulting in a set of coordinates (x, y, z) denoted by crosses on the screen. The integrated intensity of each telomere is calculated because it is proportional to the telomere length.[25]

Segmental Nuclear Volume:

Nuclear volume within one 5 μm thin nuclear section of H-cells or RS-cells is calculated according to the 3D nuclear DAPI staining as previously described.[26] Contrary to whole cell preparations (cells or cell lines), where the nuclei can be visualized with their entire volumes and z-stack analysis along the z-direction over 15 μm allows to calculate the entire nuclear volume, in tissue sections the nuclear volume analysis is limited to 5 μm nuclear segments (as used as a standard for histopathologic diagnosis) along the z-direction. Deparaffinized tissue slides of 10 and 15 μm thickness are technically unsatisfactory for Q-FISH analysis. Thus, the segmental nuclear volume represents about 30-50% of the total nuclear volume of H-cells (nuclear diameter of about 10-15 μm) and about 15-25% of the total nuclear volume of RS-cells (diameter of two up to several nuclei about 20-40 μm).

Segmental Telomere Number:

Segmental telomere number is the sum of all very short, short, mid-sized and large telomeres and aggregates identified within one 5 μm thin nuclear section of an H-cell or RS-cell.

Segmental Telomere Intensity:

Segmental telomere intensity is the sum of intensities of all very short, short, mid-sized and large telomeres and aggregates identified within one 5 μm thin nuclear section of a H-cell or RS-cell (viz. $\Sigma 2 \times 15\,000$ units$>\Sigma 7 \times 4000$ units).

Mean Telomere Intensity:

Mean telomere relative fluorescent intensity (length) of all telomeres within a given segmental volume.

Telomere Length:

Telomeres with a relative fluorescent intensity (x-axis) ranging from 0-5,000 units are classified as very short, with an intensity ranging from 5,000-15,000 units as short, with an intensity from 15,000-30,000 units as mid-sized, and with an intensity >30,000 units as large.[21]

Telomere Aggregates:

Telomere aggregates are defined as clusters of telomeres that are found in close association and cannot be further resolved as separate entities at an optical resolution limit of 200 nm.[9]

Statistical Analysis:

For each case, normally distributed parameters are compared between the two types of cells using nested ANOVA or two-way ANOVA. Multiple comparisons using the least square means tests followed where interaction effects between two factors were found to be significant. Other parameters that were not normally distributed were compared using a nonparametric Wilcoxon rank sum test. Significance level were set at p=0.05. Analyses were done using SAS v9.1 programs.

Results

Clinical Data Including Outcome:

A total of 22 diagnostic biopsies qualified for statistical analysis; 11 biopsies from 11 patients belonged to patients entering rapid remission, group A, (remission documented after one to four cycles of chemotherapy), and 11 diagnostic biopsies (6 biopsies documenting progressing disease, 5 documenting relapse) from 7 patients belonged to group B. The clinical data including treatment modalities and outcome of both groups are shown on Table 3a and b, respectively. The mean age of group A patients' is 32 years and 7 months, the mean remission duration 30 months. The mean age of patients of group B is 42 years and 8 months.

3D Telomere Q-FISH Group A:

The nuclear telomere organization of patients entering rapid remission is shown on Table 4a. Compared to mononuclear H-cell nuclei, RS-cell nuclei have a significantly larger volume and are characterized by a highly significant increase in number of very short telomere and aggregates but only by a moderate increase of the total telomere mass (segmental telomere intensity). This results in a highly significant decrease of the mean telomere intensity. However, when the number of telomeres and the total telomere mass are normalized to a virtual nuclear volume of 1000 μm$^3$, RS-cells show a decrease in total telomere numbers and total telomere mass compared to H-cells underscoring the shortening and loss of telomeres associated with the transition from H- to RS-cells.

Figure 5:
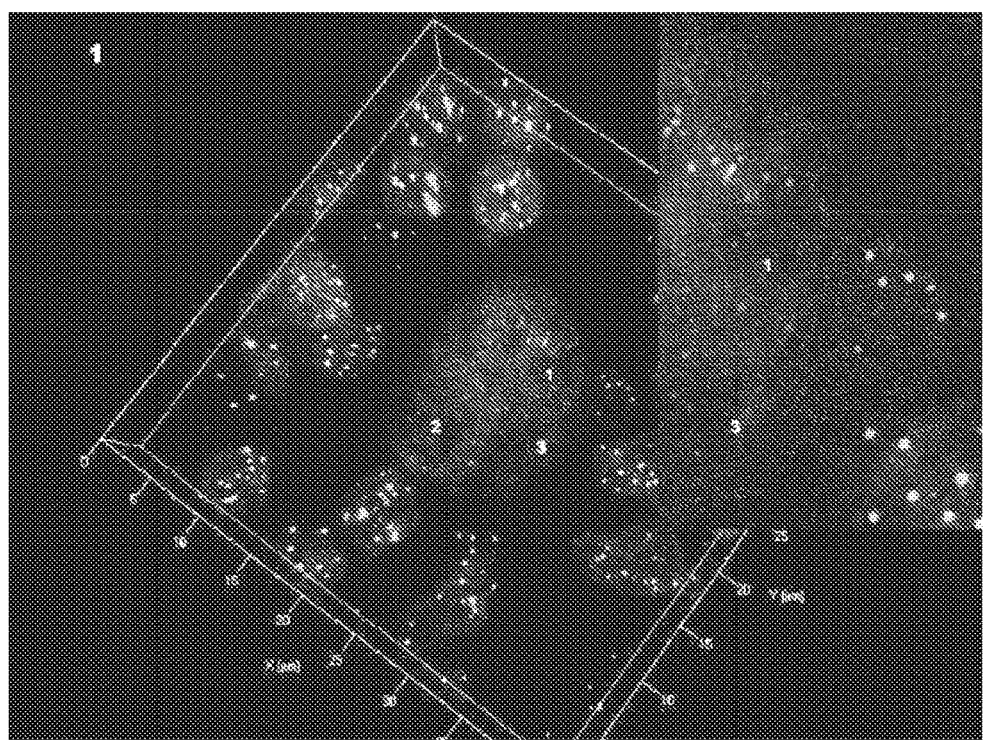
FIG. 5. 3D nuclear organization of telomeres (dots) and total nuclear DNA in Reed-Sternberg cells of relapsing Hodgkin's lymphoma. Tri-nuclear Reed-Sternberg cell (biopsy 15b) showing unequal nuclear distribution of mainly very short telomere when compared to surrounding lymphocytes, which contain midsized and large telomere. Short and very short telomere are clustered in the upper nucleus (1) of the RS-cell whereas the left (2) and lower right nucleus (3) behave like "ghost" elements with only few very short telomere. Inset highlights clustering and very short telomere in the RS-cell compared to adjacent lymphocytes.
Figure 6A:
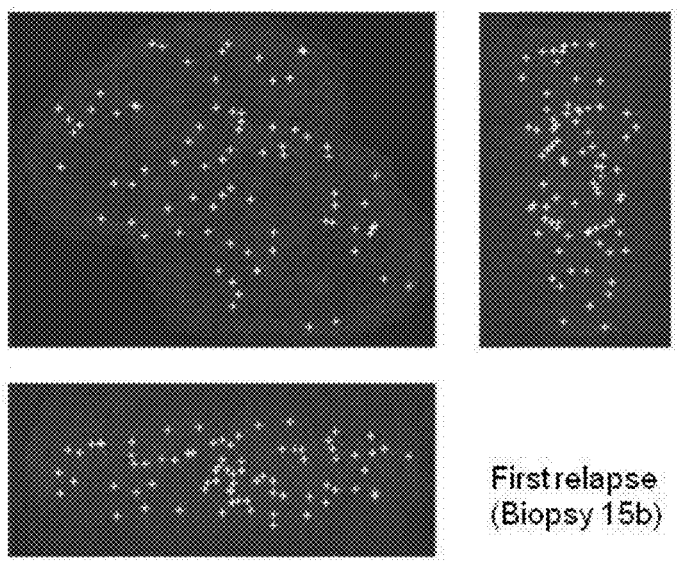
FIG. 6. Quantitative assessment of 3D telomeric profiles of RS-cells in relapse and refractory disease by TeloView. 3D Telomere dynamics in a biopsy (15b, same patient as in FIG. 5) of late 1st relapse (after 6 years) and a biopsy (15c) of a 2nd relapse (4 years) after autologous bone marrow transplantation. Death occurred 9 months after this biopsy (15c) from refractory disease. A. Upper panel: The telomere signals (white crosses) are marked in three axes (x, y, z). Lower panel: The RS-cell contains a total of 84 mainly very short telomere and 6 aggregates (above the red line) and the mean telomere intensity is at 3864 units, the segmental telomere intensity (total telomere mass) at 347732 units. B. Upper panel: Scrutiny by eye vision reveals no differences to the telomere frequency observed in A. However, alignment according to intensity (lower panel) shows 92 mostly very short telomere and 8 aggregates. Most importantly, the mean telomere intensity lowered to 2478 units and the segmental telomere intensity (total telomere mass) to 247780, demonstrating ongoing telomere shortening and loss.
Figure 6B:
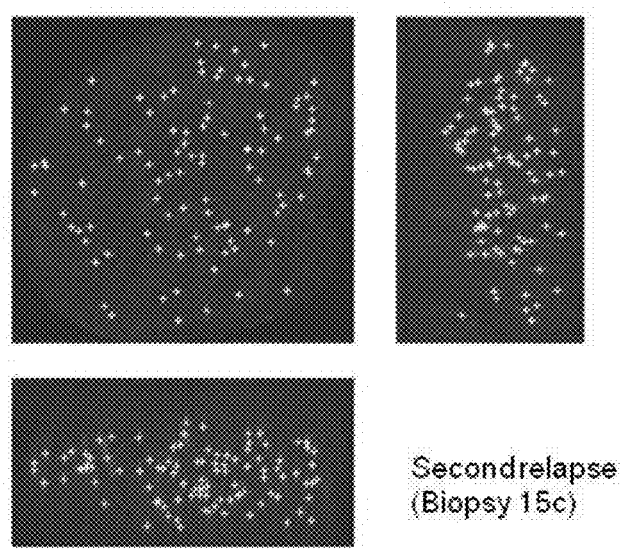

3D Telomere Q-FISH Group B:

The nuclear telomere organization of patients with progressing or relapsing disease is shown on Table 4b. Again, compared to mononuclear H-cell nuclei, RS-cell nuclei have a significantly larger volume and are characterized by a highly significant increase in number of very short telomeres and aggregates but only by a moderate increase of the total telomere mass (segmental telomere intensity). This results in a highly significant decrease of the mean telomere intensity. Most importantly, these differences between RS- and H-cells,—though analogous to those identified within the rapid remission group A—, do occur at a much advanced level. For instance, the number of very short telomere increases between H- and RS cells in group B from 72.9 to 80.8% (Table 4b), whereas a similar increase, but at a much lower level, from 54.9 to 68%, is identified in group A (Table 4a). Again, RS-cells show lowering of number and total mass of telomeres compared to H-cells in relation to a virtual nuclear volume of 1000 μm$^3$, indicating telomere loss. Thus in relapsing and refractory cases the 3D nuclear telomere characteristics have much more progressed, in particular a much higher number of very small telomeres and aggregates as well as a much more pronounced decrease of the mean telomere intensity is observed (FIG. 5). This process is dynamic and more pronounced in a second refractory relapse as documented by TeloView analysis (FIG. 6).

Figure 7:
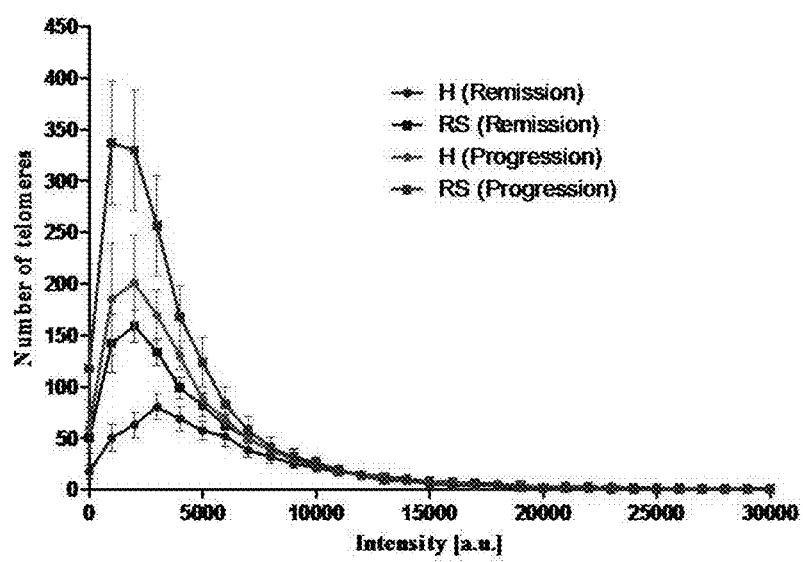
FIG. 7. Telomere distribution according to size in H- and RS-cells in rapid remission and relapsing/refractory HL. The mean telomere distributions (±2SD) in H- and RS-cells of 11 biopsies associated with rapid remission (group A) and 11 biopsies (5 relapses, 6 15 progressions) from 7 patients (group B) are shown. Results are based on 3D analysis of at least 30 Hodgkin and 30 Reed-Sternberg cells in a diagnostic 5 μm thin lymph node section of each biopsy. Frequency (y-axis) and relative fluorescent intensity, i.e. size of telomeres (x-axis) are shown. There is a highly significant shift ($p<0.0001$) from short telomere (>5000 relative fluorescence units) to very short telomere including "t-stumps" of 0-5,000 relative fluorescence units between all four curves. This difference is also observed between RS-cells of the rapid remission group A and H-cells of the relapse/progression group B, but most importantly, in a reversed manner: mononuclear H-cells of aggressive disease have already significantly more very short telomere than RS-cells of cases entering rapid and lasting remission (see also Tables 3-5). Thus, H-cells of group B differ from RS cells of group A not only by nuclear volume (expected) but also by a significantly increased number of very short telomeres. As a further sign of their aggressiveness they have already as much telomere aggregates as RS-cells of group A.

Comparison of the 3D Telomere Characteristics of Group A and B:

Most importantly, the mononuclear H-cells of progressing/relapsing cases, still capable to complete mitosis resulting in two mononuclear daughter H-cells, have already telomere characteristics identified in RS-cells of the rapid remission cases as shown in Table 5. These H-cells of group B differ from the RS-cells of group A not only by the expected difference in nuclear volume but also by the percentage of very short telomere which is even significantly higher in H-cells of group B than in RS-cells of group A (FIG. 7), consistent with multiple completed rounds of cellular division with intact nuclear and cytoplasmic separation preceding clinically apparent relapse. Thus, H-cells of refractory/relapsing cases behave in 3D nuclear telomere organization like end-stage RS-cells of the remission group A without being it.

In summary, it was concluded that H- and RS-cells of relapsing/refractory HL differ significantly from their counterparts of cases entering rapid and persistent remission. A hallmark is the very high percentage of very short telomeres and aggregates in these H-cells.

Discussion

Over the past years, the success-rate of modern treatment modalities for Hodgkin's lymphoma has stagnated at about 80-85%.[27] In about 20% of patients, the disease still relapses or progresses, despite multiple chemotherapies, radiation therapy and autologous bone marrow transplantation, demonstrating the need for a better molecular knowledge of the biology of the ill-rendering tumour cells, known as mononuclear Hodgkin- and multinuclear Reed-Sternberg cells.[28,29] It is most important to look for novel treatment approaches for this group of patients[30] and to identify such patients already at diagnosis prior to any therapy. Beside the well-known risk factor of advanced stage disease with B symptoms, microenvironment factors such as fibroblast activation, extracellular matrix remodelling and high number of macrophages[31,32] are also associated with unfavourable prognosis. However, as of today, there is no cytological/morphologic means to discern aggressive H- and RS-cells from their chemotherapy sensitive counterparts.

Here highly significant differences in the 3D telomere characteristics between Hand RS-cells of patients entering rapid and sustained remission upon first line chemotherapy on one hand, and H- and RS-cells of patients in relapse or refractory disease on the other hand are shown. Using innovative 3D quantitative FISH techniques for telomere dynamics and whole chromosome painting, as well as spectral karyotyping (SKY), detailed molecular insight in the transition of mononuclear H- to multinuclear RS-cells was obtained.[20-22]

RS-cells of classical HL as true end-stage tumour cells, characterized by abundant very short telomeres, giant "zebra" chromosomes containing concatameric repeats from two different, or parts originating from up to 7 different chromosomes, and "ghost" nuclei poor or void of telomeres and chromosomes were identified, consistent with the hypothesis of multiple ongoing breakage-bridge-fusion cycles (BBF-cycles) at the origin of RS-cell generation. Moreover, 3D super resolution microscopy (SIM) identified inter-nuclear DNA bridges between RS-cell nuclei and thus corroborated the generation of RS-cells as a result of multiple BBF-cycles.[22] Thus, in refractory/relapsing Hodgkin's lymphoma the H-cells have undergone already at diagnosis multiple BBF-cycles still allowing proper chromosomal segregation.

This pathogenetic model is further supported by the emergence of HL-relapses with unrelated clonal rearrangements, as recently reported.[33] This dynamic process of nuclear remodeling probably begins in the few clonotypic circulating B-cells identified recently by Jones and coworkers in HL[16], or, in EBV-associated HL, even earlier in activated EBV infected tonsillar germinal center B cells who escape immuno-surveillance.[34] Indeed, telomere shortening and chromosomal instability in peripheral blood lymphocytes of HL patients prior to any treatment has been identified.[35]

Relapsing/refractory stage of HL appears to be best mirrored by the Hodgkin cell-lines HDLM-2, L-1236, and U-HO1, all derived from advanced stage HL,—two of them refractory—, where by far most elements (>90%) are mononuclear H-cells.[36-38] These mononuclear H-cells,—though presenting a high complexity of chromosomal aberrations—, harbour a natural selection of complex rearrangements still allowing proper mitotic division. Their transition to multinuclear RS-cells is associated with additional increase of chromosomal complexity[22], formation of multiple aberrant mitotic spindles, telomere aggregates and a tremendous shortening of telomere.[20,39] Such extremely short telomere, also called "t-stumps"[40] and telomere aggregates are hallmarks of cancer cells.[10] At this stage of disease the H-cells escape standard chemotherapy (<<no return cells>>) and need novel therapeutic approaches.[30] The earlier these H- and RS-cells are identified, the better for the patient. The results of the 3D telomere analysis presented in this study allow one to identify such patients upfront and will help to optimize the initial therapeutic approach.

TABLE 3a

Rapid remission group A: Clinical data

| Case | Sex | Age | HL-type | Stage (Costwolds) | Remission (post cycle) | Remission duration |
|---|---|---|---|---|---|---|
| 1 | F | 57 | MC LMP1+ | IIIA | 4 × ABVD | 63 months |
| 2 | M | 24 | MC LMP1+ | IIIB | 1 × ABVD | 16 |
| 3 | M | 42 | MC | IA | 2 × ABVD | 23 |
| 4 | M | 19 | NS | IVA | 2 × ABVD | 28 |
| 5 | F | 28 | NS LMP1+ | IIA | 4 × ABVD | 41 |
| 6 | M | 27 | NS | III$_S$ A | 3 × ABVD | 17 |
| 7 | M | 34 | NS | IIIB | 4 × ABVD | 61 |
| 8 | M | 30 | NS LMP1+ | IIA | 2 × ABVD | 16 |
| 9 | M | 46 | NS LMP1+ | IIA | 1 × ABVD | 12 |
| 10 | F | 35 | NS | III$_S$ B | 1 × CVPP-AO | 16 |
| 11 | M | 17 | NS | IIB bulky | 4 × DBVE-PC + IFRT | 38 |

ABVD: Adriamycin, Bleomycin, Vinblastine, Dacarbazine
CVPP-AO: Cyclophosphamide, Vinblastine, Procarbazine, Prednisone/Adriamycin, Oncovin
DBVE-PC: Doxorubicin, Bleomycin, Vinblastine, Etoposide/Prednisone, Cyclophosphamide
IFRT: Involved field radiation therapy
MC: mixed cellularity classical Hodgkin's lymphoma
NS: nodular sclerosis classical Hodgkin's lymphoma TABLE 3b Progression/relapse group B: Clinical data

| Case | Sex | Age | HL-type | Stage | Progression/remission/relapse/outcome |
|---|---|---|---|---|---|
| 12a | F | 77 | NS LMP1+ | IIIB | 4 × ABVD → progression |
| b | | | NS LMP1+ | IIIB | 2 × R-Gem → progression, → death after 5 months |
| 13b | F | 49 | NS | IIA bulky | 3 × ESHAP, BEAC + auto BMT, → progression, → IFRT, → progression, death after 6 months |
| 14a | M | 61 | NS | IIIB | 6 × ABVD → remission, → relapse after 10 months |
| 15b | M | 38 | MC | IVB | 2 × ESHAP, BEAM + auto BMT, → remission, → relapse after 48 months |
| c | | | MC | IIIB | 4 × ICE, 2 × DHP → progression, → death after 9 months |
| 16a | M | 21 | NS | IIIB | 4 × ABVD → progression, |
| b | | | NS | IIA | 2 × ESHAP, BEAM + auto BMT, → progression, 2 × ICE, → progression, 2 × GDP, → progression, death after 3 months |
| 17a | M | 39 | NS | IIIB | 6 × ABVD → remission, → relapse after 35 months, |
| b | | | NS | IVB | 3 × ESHAP → progression → death after 7 months |
| 18a | F | 14 | NS | IVA | 4 × DBVE-PC + IFRT → remission → relapse after 4 months, auto BMT → in remission for 20 months |

ABVD: Adriamycin, Bleomycin, Vinblastine, Dacarbazine
R-Gem: Rituxan, Gemcitabine
ESHAP: Etoposide, Cytarabine, Cisplatin, Methylprednisolone
BEAC: Carmustine, Etoposide, Cytarabine, Cyclophosphamide
BEAM: Carmustine, Etoposide, Cytarabine, Melphalan
IFRT: Involved field radiation therapy
ICE: Ifosfamide, Carboplatin, Etoposide
GDP: Gemcitabine, Dexamethasone, Cisplatin
DBVE-PC: Doxorubicin, Bleomycin, Vinblastine, Etoposide/Prednisone, Cyclophosphamide
IFRT: Involved field radiation therapy
MC: mixed cellularity classical Hodgkin's lymphoma
NS: nodular sclerosis classical Hodgkin's lymphoma

TABLE 4a

Rapid remission group A: 3D telomere characteristics of Reed-Sternberg cells and Hodgkin cells of 11 diagnostic biopsies: statistics including 5 LMP1 expressing cases

| Parameter | RS-cells (N = 346; 158 LMP1+) | H-cells (N = 356; 168 LMP1+) | p-value |
|---|---|---|---|
| Segmental nuclear volume | 655 μm$^3$ (458)[1] | 355 μm$^3$ (218) | <0.0001 |
| Segmental telomere number | 31.2 (21.5) | 20.0 (13.7) | <0.0001 |
| Segmental telomere intensity | 173564 units (148258) | 139330 units (179548) | 0.0022 |
| Mean telomere intensity | 5808 units (3351) | 7453 units (4329) | <0.0001 |
| Very short telomeres (0-5000 u) | 68.0% | 54.9% | <0.0001 |
| Segmental telomere aggregates | 3.3 (3.0) | 1.6 (2.0) | <0.0001 |

[1] = standard deviation
NS = p > 0.05

TABLE 4b

Progression/relapse group B: 3D telomere characteristics of Reed-Sternberg cells and Hodgkin cells of 11 diagnostic biopsies: statistics including 2 LMP1 expressing biopsies

| Parameter | RS-cells (N = 369; 65 LMP1+) | H-cells (N = 376; 72 LMP1+) | p-value |
|---|---|---|---|
| Segmental nuclear volume | 714 μm$^3$ (456)[1] | 381 μm$^3$ (201) | <0.0001 |
| Segmental telomere number | 49.2 (34.7) | 33.4 (22.8) | <0.0001 |
| Segmental telomere intensity | 205727 units (183010) | 170393 units (131944) | 0.0007 |
| Mean telomere intensity | 4359 units (4489) | 5543 units (3198) | <0.0001 |
| Very short telomeres (0-5000 u) | 80.8% | 72.9% | <0.0001 |
| Segmental telomere aggregates | 5.5 (5.0) | 3.5 (3.4) | <0.0001 |

[1] = standard deviation
NS = p > 0.05
All parameters were analyzed with the GLM procedure except telomere <= 5000 u, this one was done with the FREQ Procedure.

TABLE 5

Rapid remission group A versus progression/relapse group B: Comparison of 3D telomere characteristics of Reed-Sternberg cells and Hodgkin cells (p-values)

| Comparison of Parameter | H-A/H-B | RS-A/RS-B | H-A/RS-B | H B/RS-A |
|---|---|---|---|---|
| Segmental nuclear volume | NS | NS | 0.0013 (H-A < RS-B) | 0.0054 (H-B < RS-A) |
| Segmental telomere number | 0.0053 (H-A < H-B) | 0.0247 (RS-A < RS-B) | 0.0004 (H-A < RS-B) | NS |
| Segmental telomere intensity | NS | NS | NS | NS |
| Mean telomere intensity | 0.0277 (H-A > H-B) | 0.0539* (RS-A > RS-B) | 0.0008 (H-A > RS-B) | NS |
| Very short telomere (<5000 u) | <0.0001 (H-A < H-B) | <0.0001 (RS-A < RS-B) | <0.0001 (H-A < RS-B) | <0.0001 (H-B > RS-A) |
| Segmental telomere aggregates | 0.0083 (H-A < H-B) | 0.0218 (RS-A < RS-B) | 0.0002 (H-A < RS-B) | NS |

H-A = Hodgkin cells group A,
H-B = Hodgkin cells group B,
RS-A = Reed-Sternberg cells group A,
RS-B = Reed-Sternberg cells group B,
NS = p > 0.05,
* = nearly significant
All parameters analyzed with the GLM procedure except telomere <= 5000, this one was done with the FREQ Procedure.

REFERENCES FOR CITATIONS IN EXAMPLE 6

1 LeBel C, Wellinger R J. Telomeres: what's new at your end? J Cell Science 2005; 118(13):2787-2788.
2 De Lange T. Shelterin: the protein complex that shapes and safeguards human telomeres. Gene Dev. 2005; 19(18): 2100-2110.
3 Hug N, Lingner J. Telomere length homeostasis. Chromosoma. 2006; 115(6):413-425.
4 DePinho R A, Polyak K. Cancer chromosomes in crisis. Nat. Genet. 2004; 36(9):932-934.
5 Landsdorp P M. Telomeres and disease. EMBO J. 2009; 28(17):2543-2540.
6 Chuang T C, Moshir S, Garini Y, et al. The three-dimensional organization of telomeres in the nucleus of mammalian cells. BMC Biol. 2004; 2:12.
7 Mai S, Garini Y. Oncogenic remodeling of the three-dimensional organization of the interphase nucleus:

c-Myc induces telomeric aggregates whose formation precedes chromosomal rearrangements. Cell Cycle. 2005; 4(10):1327-1331.

8 Louis S F, Vermolen B J, Garini Y, et al. C-Myc induces chromosomal rearrangements through telomere and chromosome remodeling in the interphase nucleus. Proc Natl Acad Sci USA. 2005; 102(27):9613-9618.

9 Mai S, Garini Y. The significance of telomeric aggregates in the interphase nuclei of tumor cells. J Cell Biochem. 2006; 97(5):904-915.

10 Mai S. Initiation of telomere-mediated chromosomal rearrangements in cancer. J Cell Biochem. 2010; 109(6): 1095-1102.

11 Knecht H and Mai S. 3D imaging of telomeres and nuclear architecture: an emerging tool of 3D nano-morphology based diagnosis. J Cell Physiol. 2011; 226(4): 859-867.

12 Hsu S M, Zhao X, Chakraborty S, et al. Reed-Sternberg cells in Hodgkin's cell lines HDLM, L-428, and KM-H2 are not actively replicating: lack of bromodeoxyuridine uptake by multinuclear cells in culture. Blood. 1988; 71(5):1382-1389.

13 Drexler H G, Gignac S M, Hoffbrand A V, Minowada J. Formation of multinucleated cells in a Hodgkin's-disease-derived cell line. Int J. Cancer. 1989; 43(6):1083-1090.

14 Newcom S R, Kadin M E, Phillips C. L-428 Reed-Sternberg cells and mononuclear Hodgkin's cells arise from a single cloned mononuclear cell. Int J Cell Cloning. 1988; 6(6):417-431.

15 Küppers R. The biology of Hodgkin's lymphoma. Nat Rev Cancer. 2009; 9(1):15-27.

16 Jones R J, Gocke C D, Kasamon Y L, et al. Circulating clonotypic B cells in classic Hodgkin lymphoma. Blood. 2009; 113(23):5920-5926.

17 Brousset P, Al Saati T, Chaouche N, et al. Telomerase activity in reactive and neoplastic lymphoid tissue: infrequent detection of activity in Hodgkin's disease. Blood. 1997; 89(1):26-31.

18 Norrback K F, Enblad G, Erlanson M, Sundstrom C, Roos G. Telomerase activity in Hodgkin's disease. Blood. 1998; 92(2):567-573.

19 Heine B, Hummel M, Demel G, Stein H. Hodgkin and Reed-Sternberg cells of classical Hodgkin's disease overexpress the telomerase RNA template (hTR). J. Pathol. 1999; 188(2):139-145.

20 Knecht H, Sawan B, Lichtensztejn D, Lemieux B, Wellinger R J, Mai S. The 3D nuclear organization of telomeres marks the transition from Hodgkin to Reed-Sternberg cells. Leukemia. 2009; 23(3):565-573.

21 Knecht H, Sawan B, Lichtensztejn Z, Lichtensztejn D, Mai S. 3D telomere FISH defines LMP1 expressing Reed-Sternberg cells as end-stage cells with telomere-poor "ghost" nuclei. Lab Invest. 2010; 90(4):611-619.

22 Guffei A, Sarkar R, Klewes L, Righolt C, Knecht H, Mai S. Dynamic chromosomal rearrangements in Hodgkin's lymphoma are due to ongoing three-dimensional nuclear remodeling and breakage-bridge-fusion cycles. Haematologica. 2010; 95(12):2038-2046.

23 Schaefer L H, Schuster D, Herz H. Generalized approach for accelerated maximum likelihood based image restoration applied to three-dimensional fluorescence microscopy. J. Microsc. 2001; 204(2):99-107.

24 Vermolen B J, Garini Y, Mai S, et al. Characterizing the three-dimensional organization of telomeres. Cytometry A. 2005; 67(2):144-150.

25 Poon S S, Martens U M, Ward R K, Lansdorp P M. Telomere length measurements using digital fluorescence microscopy. Cytometry. 1999; 36(4):267-278.

26 Sarkar R, Guffei A, Vermolen B J, Garini Y, Mai S. Alterations of centromere positions in nuclei of immortalized and malignant mouse lymphocytes. Cytometry A. 2007; 71(6):386-392.

27 Kuruvilla J. Standard therapy for advanced Hodgkin lymphoma. Hematology Am Soc Hematol Educ Program. 2009; pp 497-506.

28 Steidl C, Connors J M, Gascoyne R D. Molecular pathogenesis of Hodgkin's lymphoma: increasing evidence of the importance of the microenvironment. J Clin Oncol. 2011; 29(14):1812-1826.

29 Mathas S, Dörken B, Janz M. The molecular pathogenesis of classical Hodgkin lymphoma. Dtsch Med. Wochenschr. 2009; 134(39):1944-1948.

30 Younes A, Bartlett N L, Leonard J P, et al., Brentuximab vedotin (SGN-35) for relapsed CD30-positive lymphomas. N Engl J. Med. 2010; 363(19):1812-1821.

31 Devilard E, Bertucci F, Trempat P, et al. Gene expression profiling defines molecular subtypes of classical Hodgkin's disease. Oncogene. 2002; 21(19):3095-30102.

32 Steidl C, Farinha P, Gascoyne R D. Macrophages predict treatment outcome in Hodgkin's lymphoma. Haematologica. 2011; 96(2):186-189.

33 Obermann E C, Mueller N, Rufle A, et al. Clonal relationship of classical Hodgkin lymphoma and its recurrences. Clin Cancer Res. 2011; 17(16):5268-5274.

34 Roughan J E, Thorley-Lawson D. The intersection of Epstein-Barr virus with the germinal center. J. Virol. 2009; 83(8):3968-3976.

35 M' kacher R, Bennaceur-Griscelli A, Girinsky T, et al. Telomere shortening and associated chromosomal instability in peripheral blood lymphocytes of patients with Hodgkin's lymphoma prior to any treatment are predictive of second cancers. Int J Radiat Oncol Biol Phys. 2007; 68(2):467-471.

36 Wolf J, Kapp U, Bohlen H, et al. Peripheral blood mononuclear cells of a patient with advanced Hodgkin's lymphoma give rise to permanently growing Hodgkin-Reed Sternberg cells. Blood. 1996; 87(8):3418-3428.

37 MacLeod R A, Spitzer D, Bar-Am I, et al. Karyotypic dissection of Hodgkin's disease cell lines reveals ectopic subtelomeres and ribosomal DNA at sites of multiple jumping translocations and genomic amplification. Leukemia. 2000; 14(10):1803-1814.

38 Mader A, Brüderlein S, Wegener S, et al. U-HO1, a new cell line derived from a primary refractory classical Hodgkin lymphoma. Cytogenet Genome Res. 2007; 119 (3-4):204-210.

39 Knecht H, Brüderlein S, Wegener S, Lichtensztejn D, Lichtensztejn Z, Lemieux B, Möller P, Mai S. 3D nuclear organization of telomeres in the Hodgkin cell lines UHO1 and U-HO1-PTPN1: PTPN1 expression prevents the formation of very short telomeres including "t-stumps". BMC Cell Biology. 2010; 11:99.

40 Xu L, Blackburn E H. Human cancer cells harbour T-stumps, a distinct class of extremely short telomeres. Mol. Cell. 2007; 28(2):315-327.

Example 7

Additional patients were assessed as described in Example 6.

With the ability of three-dimensional nuclear telomere analysis to be performed on paraffin-embedded tissue blocks to specifically address the nuclear structure in the minor population of cells in HL that are the malignant component (H and RS cells), it was now possible to ask whether there were differences in the H and RS cells of patients with primary refractory or relapsing HL compared with those of good responders. In this study, 16 diagnostic lymph node biopsies from patients entering rapid remission were analyzed and compared to 16 lymph node biopsies from 10 patients who went on to have relapse or refractory disease. The results show significant differences in three-dimensional telomere dynamics of relapsing/progressing disease.

Study Design

From January 2006 to January 2011, patients diagnosed by lymph node biopsy for HL or closely related diseases at the Université de Sherbrooke were enrolled in the trial to evaluate telomere structure by three-dimensional telomere Q-FISH analysis performed on archived histology slides of diagnostic biopsies. This tumor biology study did not affect patient management. Forty-two patients entered the study (most of them prospectively), 33 had histologic diagnosis (lymph node) of classic HL, 4 had lymphocyte-predominant nodular HL, 3 had EBV-associated angioimmunoblastic T-cell lymphoma (LMP1+), 1 had T-cell anaplastic large cell lymphoma ALK+, and 1 had EBV positive large B-cell lymphoma. Among the patients with HL, four were referred from other centers (three with relapsing/progressing disease).

Methods relating to Clinical response definition, Tissue Slides, Identification of LMP1 Expressing H and RS Cells on Serial Sections with Combined 3D DAPI/Cy-3 Telomere Q-FISH Nuclear Staining, Immunohistochemistry, Telomere Q-FISH, 3D Image Acquisition, 3D Image Analysis for Telomeres and Statistical Analysis are as described in Example 6.

Results

Clinical Data Including Outcome

A total of 32 diagnostic biopsies were adequate for statistical analysis; 16 biopsies from 16 patients belonged to patients entering rapid remission, belong to group A, (remission documented after fourth cycle of chemotherapy at the latest), and 16 diagnostic biopsies (eight initial biopsies including two patients never entering remission, four documenting relapse and four disease progression) from 10 patients belonged to group B. The clinical data including treatment modalities, international prognostic score (IPS), and outcome of both groups are shown on Table 6, A and B, respectively. The groups were similar for age and IPS score. Stage 1V disease was more frequent in patients of group B (3 vs 1).

Three-Dimensional Telomere Q-FISH Group A

The nuclear telomere organization of patients entering rapid remission is shown on Table 7A. Compared with mononuclear H-cell nuclei, RS-cell nuclei have a significantly larger volume and are characterized by a significant increase in the number of very small telomeres and aggregates (P<0.01), as defined in Materials and Methods, whereas the total telomere mass (segmental telomere intensity) was nearly unchanged (P=0.395). As a result, the mean telomere intensity in RS cells is much lower compared with that in H cells (P<0.01). When the total telomere mass is normalized to a virtual nuclear volume of 1000 µm3, RS cells show a significant decrease in the total telomere mass (P<0.01) compared with H cells underscoring the shortening and loss of telomeres associated with the transition from H to RS cells [20, 21].

Three-Dimensional Telomere Q-FISH Group B

Figure 8:
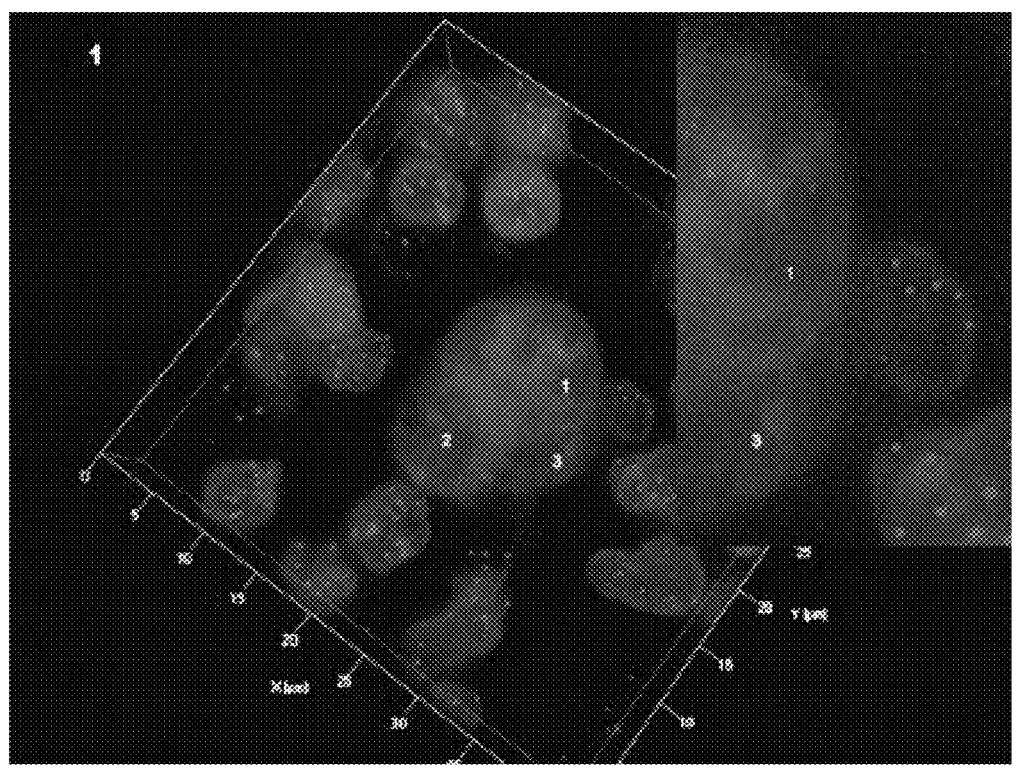
FIG. 8. Three-dimensional nuclear organization of telomeres (dots) and total nuclear DNA in RS cells of relapsing HL. Trinuclear RS cell (biopsy 20b) showing unequal nuclear distribution of mainly very small telomere when compared with surrounding lymphocytes, which contain midsized and large telomere. Small and very small telomere are clustered in the upper nucleus (1) of the RS cell whereas the left (2) and lower right nucleus (3) behave like "ghost" elements with only few very small telomere. Inset highlights clustering and very small telomere in the RS cell compared with adjacent lymphocytes.
Figure 9:
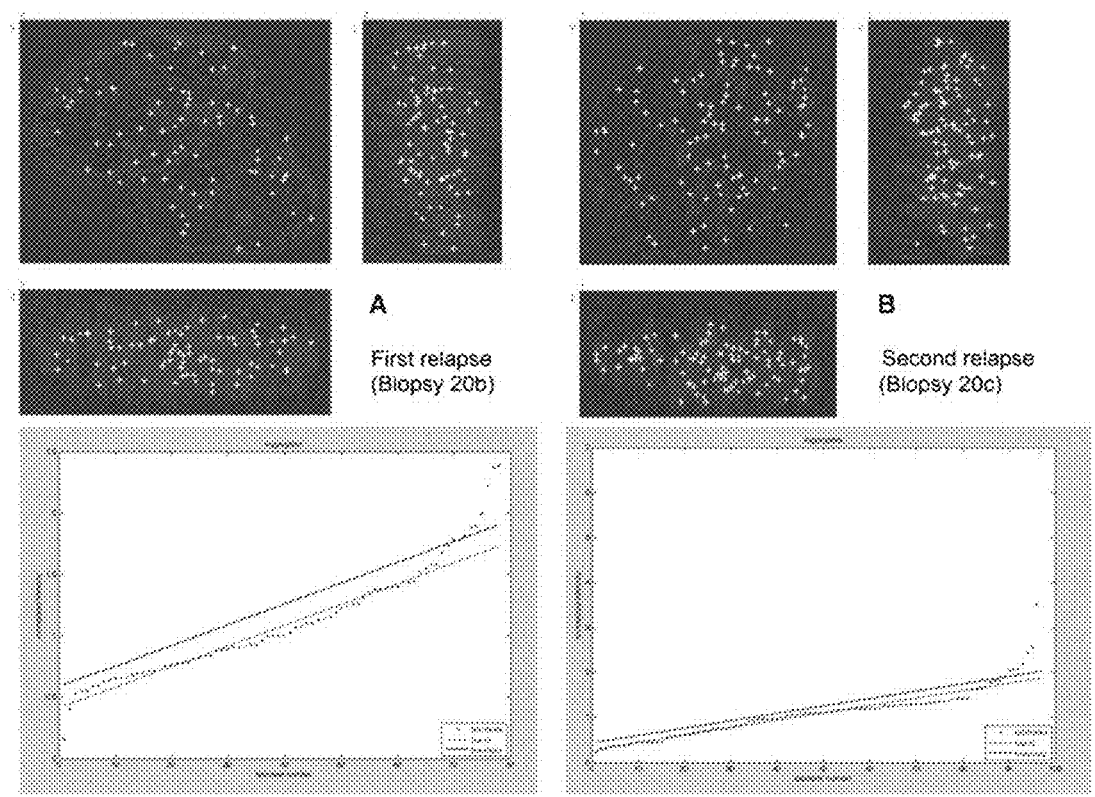
FIG. 9. Quantitative assessment of three-dimensional telomeric profiles of RS cells in relapse and refractory disease by TeloView. Three-dimensional Telomere dynamics in a biopsy (20b, same patient as in FIG. 8) of late first relapse (after 6 years) and a biopsy (20c) of a second relapse (4 years) after autologous bone marrow transplantation.

The nuclear telomere organization in patients with progressing or relapsing disease is shown on Table 7B. Again, compared with mononuclear H-cell nuclei, RS-cell nuclei have a significantly larger volume and are characterized by a significant increase in number of very small telomeres and aggregates (P<0.01) but also by a significant increase (P<0.01) of the total telomere mass (segmental telomere intensity). However, when the total telomere mass is normalized to a virtual nuclear volume of 1000 µm3, this increase in the total telomere mass is no longer identifiable (P=0.493), with a remaining still significant decrease of the mean telomere intensity (P=0.014). Most importantly, these differences between RS and H cells—although analogous to those identified within the rapid remission group A—do occur at a much advanced level. For instance, the number of very small telomere increases between H and RS cells in group B from 68.8% to 81.8% (Table 7B), whereas a similar increase, but at a much lower level, from 48.0% to 72.4%, is identified in group A (Table 7A). In analogy, the number of telomere aggregates increases between H and RS cells from 3.1 to 4.9 in group B but from 1.9 to 3.4 in group A, respectively. Thus, in relapsing and refractory cases, the characteristics of three-dimensional nuclear telomere abnormalities are much more pronounced with a higher observed number of very small telomeres and telomere aggregates as well as a decreased mean telomere intensity (FIG. 8). This process is dynamic and it was noted to worsen with advanced disease stage as seen in TeloView analysis of a second refractory relapse (FIG. 9).

Comparison of the Three-Dimensional Telomere Characteristics of Groups A and B

Most importantly, the mononuclear H cells of progressing/relapsing cases, still capable of completing mitosis resulting in two mononuclear daughter H cells, have already telomere characteristics identified in RS cells of the rapid remission cases as shown in the right track of Table 8. These H cells of group B differ from the RS cells of group A in terms of the expected difference in nuclear volume (391 vs 666 µm3), whereas the number of aggregates per cell (3.1 vs 3.4) and the percentage of very small telomere (68.8% vs 72.4%) are very similar; however, both, aggregates and a very small telomere of H cells of group B, have significantly increased compared with those of H cells of group A (P=0.032 and P=0.027, respectively; first track of Table 3). These differences are even more significant for very small telomeres (P=0.002) and for aggregates (P=0.013) when comparing the eight initial biopsies of refractory/relapsing HL (biopsies 17a, 19a, 20a, 21a, 22a, 23a, 25a, and 26a) with the diagnostic biopsies eight patients (biopsies 1-7.12) entering rapid and still ongoing sustained remission (27-70 months; mean of 47 months). Notably, these three-dimensional telomere dynamics were identified before identical ABVD chemotherapy (except case 23a) in both groups and, consequently, the different clinical course independent of initial treatment modality. For the H cells of the refractory/relapsing cases, this is consistent with multiple completed rounds of cellular division (i.e., repeated telomere shortening) that are completed with intact nuclear and cytoplasm segregation indicating primary aggressive disease. This telomere profile contrasts with that one of rapid remission cases (FIGS. 10, A and B). Importantly, the mean segmental telomere intensity (mean total telomere mass) is unchanged between H cells of group B (162,215 units) and RS cells of group A (167,241 units) as well as the mean segmental telomere number (31.0 vs 32.3). Thus, the mononuclear H cells of refractory/relapsing cases behave in their three-dimensional nuclear telomere signature like end-stage RS cells of the remission group A without being it (FIG. 11).

In summary, it is concluded that H cells of relapsing/refractory HL differ significantly from their counterparts of cases entering rapid and persistent remission. A hallmark is the very high percentage of very small telomeres and aggregates in these H cells. In addition, the H cells of relapsing/refractory HL are similar to the RS cells of HL in remission.

TABLE 6A

Clinical Data: Rapid Remission Group A
(A) Rapid Remission Group A

| Case No. | Sex | Age (years) | HL-Type | Stage (Costwolds) | IPS | Remission (After Cycle) | Remission Duration (months) |
|---|---|---|---|---|---|---|---|
| 1 | F | 57 | MC LMP1+ | IIIA | 1 | 4 × ABVD | 69 |
| 2 | M | 24 | MC LMP1+ | IIIB | 1 | 1 ×ABVD | 27 |
| 3 | M | 42 | MC | IA | 1 | 2 × ABVD | 28 |
| 4 | M | 19 | NS | IVA | 2 | 2 × ABVD | 35 |
| 5 | F | 28 | NS LMP1+ | IIA | 0 | 4 × ABVD | 50 |
| 6 | M | 27 | NS | III, A | 1 | 3 × ABVD | 34 |
| 7 | M | 34 | NS | IIIB | 2 | 4 × ABVD | 70 |
| 8 | M | 30 | NS LMP1+ | IIA | 1 | 2 × ABVD | 17 |
| 9 | M | 46 | NS LMP1+ | IIA | 1 | 1 × ABVD | 16 |
| 10 | F | 35 | NS | III, B | 1 | 1 × CVPP-AO | 17 |
| 11 | M | 17 | NS | IIB bulky | 1 | 4 × DBVE-PC + IFRT | 42 |
| 12 | M | 71 | MC LMP1+ | IIIB | 4 | 4 × ABVD | 62 |
| 13 | M | 23 | SN | IIIB | 4 | 4 × ABVD | 9 |
| 14 | M | 58 | MC LMP1+ | IIIB | 2 | 2 × ABVD | 6 |
| 15 | M | 40 | NS | IIIB bulky | 2 | 4 × ABVD + IFRT | 6 |
| 16 | F | 73 | NS | IIIB | 5 | 4 × ABVD | 23 |

TABLE 6B

Clinical Data: Progression/Relapse Group B
(B) Progression/Relapse Group B

| Case No. | Sex | Age (years) | HL-type | Stage | IPS | Progression (prog)/Remission (rem)/Relapse (rel)/Outcome |
|---|---|---|---|---|---|---|
| 17a | F | 77 | NS LMP1+ | IIIB | 4 | 4 × ABVD → prog |
| b | | | NS LMP1+ | IIIB | 2 | 2 × R-Gem → prog, → death after 5 months |
| 18b | F | 41 | NS | IIA, bulky | 1 | 3 × ESHAP, BEAC + auto BMT, → prog, → IFRT, → prog, death after 6 months |
| 19a | M | 61 | NS | IIIB | 1 | 6 × ABVD → rem, → rel after 10 months |
| b* | | | NS | IIA | 2 | 2 × ESHAP, BEAM + auto BMT, → prog, 2 × R-Gem, → prog |
| 20a* | M | 38 | NS | IVB | 3 | 6 × ABVD → rem, → rel after 60 months |
| b | | | MC | IVB | 2 | 2 × ESHAP, BEAM + auto BMT, → rem, → rel after 48 months |
| c | | | MC | IIIB | 4 | 4 × ICE, 2 × DHP → prog, → death after 9 months |
| 21a | M | 21 | NS | IIIB | 1 | 4 × ABVD → prog |
| b | | | NS | IIA | 2 | 2 × ESHAP, BEAM + auto BMT, → prog, 2 × ICE, → prog, 2 × GDP, → prog, death after 3 months |
| 22a | M | 49 | NS | IIIB | 2 | 6 × ABVD → rem, → rel after 35 months |
| b | | | NS | IVB | 2 | 3 × ESHAP → prog → death after seven months |
| 23a | F | 14 | NS | IVA | 0 | 4 × DBVE-PC + IFRT → rem → rel after four**** months, auto BMT → in rem for 24 months |
| 24b | M | 33 | NS syncrial | IIB | 1 | 3 × ESHAP → prog, 3 × ICE → prog → death after 2 months |
| 25a | M | 48 | NS | IVB | 6 | 6 × ABVD → rem, → rel after 5 months, 2 × ESHAP, BEAM + auto BMT, → in rem for 7 months |
| 26a | M | 28 | NS | IIB | 1 | 4 × ABVD → prog, 2 × ESHAP, BEAM + auto BMT, → in rem for 7 months |

ABVD indicates adriamycin, bleomycin, vinblastine, dacarbazine;
BEAC, carmustine, etoposide, cytarabine, cyclophosphamide;
BEAM, carmustine, etoposide, cytarabine, melphalan;
CVPP-AO, cyclophosphamide, vinblastine, procarbazine, prednisone/adriamycin, oncovin;
DBVE-PC, doxorubicin, bleomycin, vinblastine, etoposide/prednisone, cyclophosphamide;
ESHAP, etoposide, cytarabine, cisplatin, methylprednisolone;
GDP, gemcitabine, dexamethasone, cisplatin;
ICE, ifosfamide, carboplatin, etoposide;
IFRT, involved field radiation therapy;
IPS, international prognostic score;
MC, mixed cellularity classic HL;
NS, nodular sclerosis classic HL;
R-Gem, rituxan, gemcitabine.
*Biopsies with only RS cells statistically analyzed because the number of H cells in these biopsies was fewer than 30.

TABLE 7

Three-dimensional Telomere Characteristics of RS Cells and H Cells of 16
(A; Rapid Remission Group A) and 14 Diagnostic Biopsies (B;
Progression/Relapse Group B).

(A) Rapid Remission Group A: Statistics Including Seven LMP1-Expressing Cases

| Parameter | RS cells (n = 510; 223 LMP1+) | H cells (n = 524; 235 LMP1+) | P |
|---|---|---|---|
| Segmental nuclear volume | 666 µm$^3$ (422)* | 366 µm$^3$ (201) | <.01 |
| Segmental telomere number | 32.3 (23.1) | 20.9 (15.8) | <.01 |
| Segmental telomere intensity | 162,215 units (148,233) | 154,824 units (182,473) | NS |
| Mean telomere intensity | 5425 units (3362) | 7682 units (4496) | <.01 |
| Very small telomere (0-5000 U) | 72.4% (15.2) | 48.0% (18.4) | <.01 |
| Segmental telomere aggregates | 3.4 (3.3) | 1.9 (2.3) | <.01 |

(B) Progression/Relapse Group B: Statistics Including Two LMP1-Expressing Biopsies

| Parameter | RS cells (n = 467; 65 LMP1+) | H cells (n = 473; 72 LMP1+) | P |
|---|---|---|---|
| Segmental nuclear volume | 718 µm$^3$ (446)* | 391 µm$^3$ (193) | <.01 |
| Segmental telomere number | 44.0 (33.3) | 31.0 (21.7) | <.01 |
| Segmental telomere intensity | 197,951 units (173,103) | 167,241 units (125,141) | <.01 |
| Mean telomere intensity | 5159 units (6968) | 5986 units (3263) | .014 |
| Very small telomere (0-5000 u) | 81.8% (15.5) | 68.8% (15.1) | <.01 |
| Segmental telomere aggregates | 4.9 (4.7) | 3.1 (3.2) | <.01 |

*Standard deviation.

TABLE 8

Rapid Remission Group A Versus Progression/Relapse Group B:
Comparison of Three-dimensional Telomere Characteristics of RS Cells and H
Cells (P )

| Comparison of Parameter | H-A/H-B (16/14)* | RS-A/RS-B (16//16) | H-A/RS-B (16/16) | H-B/RS-A (14/16) |
|---|---|---|---|---|
| Segmental nuclear volume | NS | NS | <.01 (H-A < RS-B) | <.01 (H-B < RS-A) |
| Segmental telomere number | .015 (H-A < H-B) | NS | <.01 (H-A < RS-B) | NS |
| Segmental telomere intensity | NS | NS | NS | NS |
| Mean telomere intensity | .022 (H-A > H-B) | NS | <.01 (H-A > RS-B) | NS |
| Very short telomere (<5000 units) | .027 (H-A < H-B) | NS | <.01 (H-A < RS-B) | NS |
| Segmental telomere aggregates | .032 (H-A < H-B) | NS | <.01 (H-A < RS-B) | NS |

All parameters analyzed with the GLM procedure except telomeres less than 5000, this one was done with t test.
NS = P > .05.
H-A indicates Hodgkin cells group A;
H-B, Hodgkin cells group B;
RS-A, Reed-Sternberg cells group A;
RS-B, Reed-Sternberg cells group B.
*Number of cases compared.

Discussion

Here highly significant differences in the three-dimensional telomere characteristics between H and RS cells of patients entering rapid and sustained remission on first-line chemotherapy and those of patients who have a relapsing or refractory disease course are shown (Table 7, A and B). H cells of refractory/relapsing cases already have a three-dimensional telomere signature corresponding to that one of RS cells in the remission group (Table 8 and FIG. 11) without being endstage tumor cells. Importantly, when comparing the eight initial diagnostic biopsies of the refractory/relapsing group with diagnostic biopsies of eight patients entering rapid and still ongoing long remission (mean of 47 months) before identical ABVD chemotherapy, these differences are even more pronounced; H cells of aggressive HL do contain much higher numbers of very small telomeres (P=0.002) and more aggregates (P=0.013) than do H cells of diagnostic biopsies entering long-lasting remission. H cells of refractory/relapsing cases—although having passed through multiple rounds of mitotic division, as shown by accumulation of very small telomeres and increase in aggregates—are still capable to of further cell division and thus will increase the tumor bulk. Modeling the telomere abnormalities found in relapsing/refractory stage HL are the Hodgkin cell lines L-428, HDLM-2, L-1236, and U-HO1, all derived from advanced-stage HL, three of them refractory, where by far most cells (>90%) are mononuclear H cells [37-40]. These mononuclear H cells, despite having a high complexity of chromosomal aberrations, are able to undergo mitotic division. Their transition to multinuclear end-stage RS cells is associated with a further increase in chromosomal complexity [22], formation of multiple aberrant mitotic spindles, telomere aggregates, and a further shortening of telomere [20, 41]. Such extremely small telomere, also called t-stumps [42], and telomere aggregates are hallmarks of cancer cells [10].

This study shows that here are fundamental differences between H and RS cells of patients that will go into remission as opposed to those that will recur/relapse. This difference is reflected in all 3D parameters that were measured (Tables 7 and 8, FIG. 10). H cells of the remission group are distinct from RS cells of that same group. H cells of the recurrence/relapse group are similar to RS cells in general and especially to those of the remission group.

One distinction between patients at diagnosis who will go into remission or recurrence/relapse, is that the H cells of the relapse/recurrence group are similar to the RS cells of the remission group. As shown in Table 7, where detailed numbers for H cells in the B group (progression/relapse; 473 were measured) and RS cells in the A group (remission; 510 were measured) are given, it is clear that except the size of the H and RS cells (as it should be—H cells are mononucleated, while RS cells are multi-nucleated and therefore larger), all other 3D parameters are not significantly different.

Table 8 summarizes all the p values for cross-cell comparisons. Looking at the most right feature (H-B/RS-A; that is the comparison of the H cell of the B group with the RS cell of the A group), it is shown that except for the sizes of the cells, nothing is significantly different.

Overall, a novel prognostic tool predictive of poor biologic activity in HL—the three-dimensional nuclear telomere structure has been identified. Studies are ongoing to confirm this observation in an independent cohort of HL patients and to study a large-enough cohort to evaluate whether this is an independent biomarker once stage, subtype, age, and other known prognostic factors are analyzed. The ability to study the nuclear structure of the malignant subpopulation of HL has the potential of providing a major advance to the field of HL management.

In summary, H and RS cells are characterized by a distinct three-dimensional telomere nuclear organization. Three-dimensional telomere signatures of mononuclear H cells in refractory/relapsing HL are significantly different from those in HL rapidly entering sustained remission. In refractory Hodgkin disease, the H cells show a three-dimensional telomere fingerprint (significantly higher number of very small telomeres and aggregates) nearly identical to that one of RS cells of the remission group. These H cells appear to escape standard chemotherapy but may be responding to novel therapeutic approaches.

LITERATURE CITED FOR EXAMPLE 7

[1] LeBel C and Wellinger R J (2005). Telomeres: what's new at your end? J Cell Science 118, 2787-2788.
[2] De Lange T (2005). Shelterin: the protein complex that shapes and safeguards human telomeres. Gene Dev 19, 2100-2110.
[3] Hug N and Lingner J (2006). Telomere length homeostasis. Chromosoma 115, 413-425.
[4] DePinho R A and Polyak K (2004). Cancer chromosomes in crisis. Nat Genet. 36, 932-934.
[5] Landsdorp P M (2009). Telomeres and disease. EMBO J. 28, 2532-2540.
[6] Chuang T C, Moshir S, Garini Y, Chuang A Y C, Young I T, Vermolen B, van den Doel R, Mougey V, Perrin M, Braun M, et al. (2004). The three-dimensional organization of telomeres in the nucleus of mammalian cells. BMC Biol 2, 12.
[7] Mai S and Garini Y (2005). Oncogenic remodeling of the three-dimensional organization of the interphase nucleus: c-Myc induces telomeric aggregates whose formation precedes chromosomal rearrangements. Cell Cycle 4, 1327-1331.
[8] Louis S F, Vermolen B J, Garini Y, Young I T, Guffei A, Lichtensztein Z, Kuttler F, Chuang T C, Moshir S, Mougey V, et al. (2005). C-Myc induces chromosomal rearrangements through telomere and chromosome remodeling in the interphase nucleus. Proc Natl Acad Sci USA 102, 9613-9618.
[9] Mai S and Garini Y (2006). The significance of telomeric aggregates in the interphase nuclei of tumor cells. J Cell Biochem 97, 904-915.
[10] Mai S (2010). Initiation of telomere-mediated chromosomal rearrangements in cancer. J Cell Biochem 109, 1095-1102.
[11] Knecht H and Mai S (2011). 3D imaging of telomeres and nuclear architecture: an emerging tool of 3D nano-morphology based diagnosis. J Cell Physiol 226, 859-867.
[12] Hsu S M, Zhao X, Chakraborty S, Liu Y F, Whang-Peng J, Lok M S, and Fukuhara S (1988). Reed-Sternberg cells in Hodgkin's cell lines HDLM, L-428, and KM-H2 are not actively replicating: lack of bromodeoxyuridine uptake by multinuclear cells in culture. Blood 71, 1382-1389.
[13] Drexler H G, Gignac S M, Hoffbrand A V, and Minowada J (1989). Formation of multinucleated cells in a Hodgkin's-disease-derived cell line. Int J Cancer 43, 1083-1090.
[14] Newcom S R, Kadin M E, and Phillips C (1988). L-428 Reed-Sternberg cells and mononuclear Hodgkin's cells arise from a single cloned mononuclear cell. Int J Cell Cloning 6, 417-431.
[15] Küppers R (2009). The biology of Hodgkin's lymphoma. Nat Rev Cancer 9, 15-27.
[16] Jones R J, Gocke C D, Kasamon Y L, Miller C B, Perkins B, Barber J P, Vala M S, Gerber J M, Gellert L L, Siedner M, et al. (2009). Circulating clonotypic B cells in classic Hodgkin lymphoma. Blood 113, 5920-5926.
[17] Brousset P, Al Saati T, Chaouche N, Zenou R C, Schlaifer D, Chittal S, and Delsol G (1997). Telomerase activity in reactive and neoplastic lymphoid tissue: infrequent detection of activity in Hodgkin's disease. Blood 89, 26-31.
[18] Norrback K F, Enblad G, Erlanson M, Sundstrom C, and Roos G (1998). Telomerase activity in Hodgkin's disease. Blood 92, 567-573.
[19] Heine B, Hummel M, Demel G, and Stein H (1999). Hodgkin and Reed-Sternberg cells of classical Hodgkin's disease overexpress the telomerase RNA template (hTR). J Pathol 188, 139-145.
[20] Knecht H, Sawan B, Lichtensztejn D, Lemieux B, Wellinger R J, and Mai S (2009). The 3D nuclear organization of telomeres marks the transition from Hodgkin to Reed-Sternberg cells. Leukemia 23, 565-573.
[21] Knecht H, Sawan B, Lichtensztejn Z, Lichtensztejn D, and Mai S (2010). 3D telomere FISH defines LMP1 expressing Reed-Sternberg cells as end-stage cells with telomere-poor "ghost" nuclei. Lab Invest 90, 611-619.
[22] Guffei A, Sarkar R, Klewes L, Righolt C, Knecht H, and Mai S (2010). Dynamic chromosomal rearrangements in Hodgkin's lymphoma are due to ongoing three-dimensional nuclear remodeling and breakage-bridge-fusion cycles. Haematologica 95, 2038-2046.
[23] Schaefer L H, Schuster D, and Herz H (2001). Generalized approach for accelerated maximum likelihood based image restoration applied to three-dimensional fluorescence microscopy. J Microsc 204, 99-107.
[24] Vermolen B J, Garini Y, Mai S, Mougey V, Fest T, Chuang T C, Chuang A Y, Wark L, and Young I T (2005). Characterizing the three-dimensional organization of telomeres. Cytometry A 67, 144-150.
[25] Poon S S, Martens U M, Ward R K, and Lansdorp P M (1999). Telomere length measuring using digital fluorescence microscopy. Cytometry 36, 267-278.

[26] Sarkar R, Guffei A, Vermolen B J, Garini Y, and Mai S (2007). Alterations of centromere positions in nuclei of immortalized and malignant mouse lymphocytes. Cytometry A 71, 386-392.

[27] Kuruvilla J (2009). Standard therapy for advanced Hodgkin lymphoma. Hematology Am Soc Hematol Educ Program, pp. 497-506.

[28] Steidl C, Connors J M, and Gascoyne R D (2011). Molecular pathogenesis of Hodgkin's lymphoma: increasing evidence of the importance of the microenvironment. J Clin Oncol 29, 1812-1826.

[29] Mathas S, Dörken B, and Janz M (2009). The molecular pathogenesis of classical Hodgkin lymphoma. Dtsch Med Wochenschr 134, 1944-1948.

[30] Younes A, Bartlett N L, Leonard J P, Kennedy D A, Lynch C M, Sievers E L, and Forero-Torres A (2010). Brentuximab vedotin (SGN-35) for relapsed CD30-positive lymphomas. N Engl J Med 363, 1812-1821.

[31] Hasenclever D and Diehl V (1998). A prognostic score for advanced Hodgkin's disease. International Prognostic Factors Project on Advanced Hodgkin's Disease. N Engl J Med 339, 1506-1514.

[32] Devilard E, Bertucci F, Trempat P, Bouabdallah R, Loriod B, Giaconia A, Brousset P, Granjeaud S, Nguyen C, Birnbaum D, et al. (2002). Gene expression profiling defines molecular subtypes of classical Hodgkin's disease. Oncogene 21, 3095-3102.

[33] Steidl C, Farinha P, and Gascoyne R D (2011). Macrophages predict treatment outcome in Hodgkin's lymphoma. Haematologica 96, 186-189.

[34] Steidl C, Telenius A, Shah S P, Farinha P, Barclay L, Boyle M, Connors J M, Horsman D E, and Gascoyne R D (2011). Genome-wide copy number analysis of Hodgkin Reed-Sternberg cells identifies recurrent imbalances with correlations to treatment outcome. Blood 116, 418-427.

[35] Canioni D, Deau-Fischer B, Taupin P, Ribrag V, Delarue R, Bosq J, Rubio M T, Roux D, Vasiliu V, Varet B, et al. (2009). Prognostic significance of new immunohistochemical markers in refractory classical Hodgkin lymphoma: a study of 59 cases. PLoS One 4, e6341.

[36] Hutchings M, Loft A, Hansen M, Pedersen L M, Buhl T, and Jurlander J (2006). FDG-PET after two cycles of chemotherapy predicts treatment failure and progression-free survival in Hodgkin lymphoma. Blood 107, 52-59.

[37] Schaadt M, Fonatsch C, Kirchner H, and Diehl V (1979). Establishment of a malignant, Epstein-Barr-virus (EBV)-negative cell-line from the pleura effusion of a patient with Hodgkin's disease. Blut 38, 185-190.

[38] Wolf J, Kapp U, Bohlen H, Kornacker M, Schoch C, Stahl B, Mücke S, von Kalle C, Fonatsch C, Schaefer H E, et al. (1996). Peripheral blood mononuclear cells of a patient with advanced Hodgkin's lymphoma give rise to permanently growing Hodgkin-Reed Sternberg cells. Blood 87, 3418-3428.

[39] MacLeod R A, Spitzer D, Bar-Am I, Sylvester J E, Kaufmann M, Wernich A, and Drexler H G (2000). Karyotypic dissection of Hodgkin's disease cell lines reveals ectopic subtelomeres and ribosomal DNA at sites of multiple jumping translocations and genomic amplification. Leukemia 14, 1803-1814.

[40] Mader A, Brüderlein S, Wegener S, Melzner I, Popov S, Muller-Hermelink H K, Barth T F, Viardot A, and Möller P (2007). U-HO1, a new cell line derived from a primary refractory classical Hodgkin lymphoma. Cytogenet Genome Res 119, 204-210.

[41] Knecht H, Brüderlein S, Wegener S, Lichtensztejn D, Lichtensztejn Z, Lemieux B, Möller P, and Mai S (2010). 3D nuclear organization of telomeres in the Hodgkin cell lines U-HO1 and U-HO1-PTPN1: PTPN1 expression prevents the formation of very short telomere including "t-stumps". BMC Cell Biol 11, 99.

[42] Xu L and Blackburn E H (2007). Human cancer cells harbour T-stumps, a distinct class of extremely short telomeres. Mol Cell 28, 315-327.

[43] Obermann E C, Mueller N, Rufle A, Menter T, Mueller-Garamvoelgyi E, Cathomas G, Dirnhofer S, and Tzankov A (2011). Clonal relationship of classical Hodgkin lymphoma and its recurrences. Clin Cancer Res 17, 5268-5274.

[44] Roughan J E and Thorley-Lawson D (2009). The intersection of Epstein-Barr virus with the germinal center. J Virol 83, 3968-3976.

[45] M' kacher R, Bennaceur-Griscelli A, Girinsky T, Koschielny S, Delhommeau F, Dossou J, Violot D, Leclercq E, Courtier M H, Béron-Gaillard N, et al. (2007). Telomere shortening and associated chromosomal instability in peripheral blood lymphocytes of patients with Hodgkin's lymphoma prior to any treatment are predictive of second cancers. Int J Radiat Oncol Biol Phys 68, 467-471.

Example 8

Automated Three-Dimensional Genome Scanning Based on the Nuclear Architecture of Telomeres Abstract Telomeres, the end of chromosomes, are organized in a nonoverlapping fashion and form microterritories in nuclei of normal cells. Previous studies have shown that normal and tumor cell nuclei differ in their 3D telomeric organization. The differences include a change in the spatial organization of the telomeres, in telomere numbers and sizes and in the presence of telomeric aggregates. Previous attempts to identify the above parameters of 3D telomere organization were semi-automated. Here the automation of 3D scanning for telomere signatures in interphase nuclei based on three-dimensional fluorescent in situ hybridization (3D-FISH) is described and, for the first time, its sensitivity in tumor cell detection is defined. The data were acquired with a high throughput scanning/acquisition system that allows to measure cells and acquire 3D images of nuclei at high resolution with 403 or 603 oil and at a speed of 10,000-15,000 cells, depending on the cell density on the slides. The automated scanning, TeloScan, is suitable for large series of samples and sample sizes. The sensitivity of this automation for tumor cell detection is defined. The data output includes 3D telomere positions, numbers of telomeric aggregates, telomere numbers, and telomere signal intensities. One aberrant cell in 1,000 normal cells was able to be detected. In conclusion, tumor cells were detected based on 3D architectural profiles of the genome. This new tool could, in the future, assist in patient diagnosis, in the detection of minimal residual disease, in the analysis of treatment response and in treatment decisions.

Cancers often are the result of ongoing genomic instability (1), to which telomere dysfunction contributes (2). Ongoing telomere attrition due to incomplete replication of the lagging strand during DNA synthesis results in critically short telomeres and uncapping, a hallmark of premalignant and tumor cells. The loss of telomeric DNA promotes activation of Ataxia telangiectasia mutated (ATM)-kinase and nonhomologous end joining (NHEJ) (3, 4).

Telomeres were used in the past as a prognostic marker in cancer, including breast cancer (5-7) prostate cancer (8-10), neuroblastoma and glioblastoma (11, 12), or esophageal squamous cell carcinoma (13).

Normal and tumor cell nuclei significantly differ from each other with respect to their nuclear architecture including telomere numbers and sizes and the formation of telomeric aggregates. Telomeric aggregates are clusters of telomeres that at an optical resolution of 200 nm, cannot be separated further by conventional 3D fluorescent microscopy (2). Telomeric aggregates represent telomeres that display end-to-end fusions or telomeres in very close proximity. Telomeric aggregates that represent fusions will initiate breakage-bridge-fusion cycles resulting in dynamic changes of the genetic material found in each daughter cells (2). The changes, alterations of chromosome number, and 3D nuclear architecture of telomeres, have been used to define the transition of mononucleated H-cells to multinucleated Reed-Sternberg cells in Hodgkin's Lymphoma (14-17), to classify subgroups of glioblastoma patients (11) to detect premalignant cells in mouse plasmacytoma and early lesions in cervical cancer (18).

Based on these findings a reliable test that is easy to use and that will be applicable to a broad range of such cancers has been developed. For cancer diagnosis it is common to use the four-stage TNM system, a classification system developed by Denoix (19), which is based on the size of the tumor and how far it has spread from its original location in the body.

Staging methods for leukemia are based on RAI or Binet. The widely used RAI classification system (20) is based on the risk of developing lymphocytosis and the degree of involvement of lymphoid organs. The Binet staging (21) classifies chronic lymphocytic leukemia (CLL) according to the number of lymphoid tissues that are involved, i.e., spleen and lymph nodes, as well as the presence of low red blood cell count (anemia) or low number of blood platelets (thrombocytopenia). Staging assists in the planning of a person's treatment, and is useful in the estimation of a person's prognosis (likely outcome or course of the disease). This classic staging system needs to be refined by a new array of biomarkers those address the heterogeneity of tumors.

Biomarkers such as estrogen receptor (ER), HER-2/neu in breast cancer are used for optimization of therapies and prediction of the outcome of treatments. Other predictors are PSA (prostate cancer) or EGFR (colon cancer). In recent years the focus has shifted toward molecular markers in genetics, epigenetics, the analysis of gene-expression patterns (22), and proteomics (23-25). The molecular cancer diagnostic is looking at changes on genetic and epigenetic levels (26), translocations (SKY), and variation in copy numbers (array CGH).

Overall there is a need for a diagnostic tool that allows for the detection of a broad array of tumors.

The ideal biomarker for tumors would not only be applicable for a wide range of tumors but it would also provide a basis for the tailoring of optimal treatments, the prediction of success, and monitoring of treatment response (27-30).

The choice for tumor cell detection was the development of an automated 3D detection system. The automated 3D scanning presented here allows for a high throughput of samples, while the data output includes numbers of telomeric aggregates, telomere count, and telomere signal intensity and size. The purpose of this study was the assessment of sensitivity of tumor cell detection based on the presence of 3D alterations in telomeres using the 3D scan of interphase nuclei. Sensitivity tests of this new tool show that it is possible to detect one aberrant cell in 1,000 normal cells.

Materials and Methods

Mice and B Cell Isolation

These experiments were approved by the ethical committee, protocol number 07-002/1/2/3. The plasmacytoma cell line MOPC460D, a gift of J. Mushinski (National Institutes of Health, Bethesda), were cultured as described (31). T38H mice (32) were obtained from Harwell, UK (33). The mice were kept under specific pathogen-free (SPF) conditions. At 8 weeks of age, three male mice were euthanized, and the spleens were harvested. B and T lymphocytes were flushed out of the spleen with 3 ml RPMI medium. The cells were sedimented for 5 min at 270 g. The pellets were resuspended with 5 ml ACK-buffer (150 mM NH4Cl, 10 mM KHCO3, 100 mM Na-EDTA, pH 7.4), then centrifuged for 5 min at 120 g. The pellet was washed once with RPMI-medium.

Cell Fixation

Mouse plasmacytoma cells (MOPC) and primary mouse cells were fixed in a way that preserves the shape of 3D nuclei (34-36) using the following protocol: ~10 million cells were washed in PBS then centrifuged at 120 g for 5 min at room temperature (RT). Cell pellets were resuspended in 5 ml of 75 mM KCl for 10 min at room temperature. After adding 1 ml fixative (3:1; methanol/acetic acid) the tubes were carefully inverted three to four times to gently mix the cells with the fixative. Cells were centrifuged again at room temperature for 10 min at 120 g. The cell pellet was washed with 3 ml fixative and centrifuged for 10 min at 120 g. The final cell pellet was resuspended in 1 ml fixative and stored at −20° C.

Determination of Tumor Cell Frequencies in Mixtures with Normal Lymphocytes

For the dilution of MOPC with normal mouse lymphocytes the cell number of each suspension was determined by counting using a phase hemacytometer, (Hausser Scientific, VWR International, Mississauga, Ontario, Canada). A $2 \times 10^5$ cells were applied onto each microscope slide and left to air dry prior to hybridization with telomere specific paints. For spiking experiments samples of $2 \times 10^5$ normal cells with diluted with 1 MOPC cell in 1,000 normal lymphocytes, 1:100, 1:20, and 1:10. In parallel, slides were prepared with mouse plasmacytoma and normal cells, only.

Telomere Q-FISH

Telomeres were hybridized with Cy3-labelled peptide nucleic acid probes (DAKO, Denmark) according to our published protocols (37). The 3D-fixed cells were washed in freshly prepared methanol/acetic acid (3:1) fixative and positioned on the slides. After air-drying the slides, the cells were fixed in 3.7% formaldehyde/phosphate-buffered saline (PBS) for 20 min, washed three times for 5 min in PBS. After an incubating in TPBS (0.5%, Triton X-100 in PBS) for 10 min the slides were incubated in 20% glycerol for 1 h followed by four freeze-thaw cycles in liquid nitrogen and three washes with PBS. After a 5-min incubation in 0.1N HCl the slides were washed for 5 min in PBS, twice. Prior to the hybridization the samples were equilibrated for 1 h in 70% formamide (Fluka-Sigma Aldrich, St Louis, Mo.), 2×SSC at room temperature. The slides were hybridized with $Cy^3$-labeled telomere-specific PNA probe (DAKO) and washed as previously published (34-36).

DAPI (4′,6-diamidino-2-phenylindole) was purchased from Sigma Aldrich (Oakville, ON) and used at 0.1 μg ml$^{-1}$ to counterstain the nuclei on the slides (31, 35). For the mounting medium, ProLong® antifade Gold mounting medium (Molecular Probes™, Invitrogen detection technologies, Carlsbad, Calif.) was used. The slides were allowed to dry over night at 4° C. under light protected conditions. The slides were stored at −20° C. until use.

Automated Image Acquisition and Processing

The automated Image acquisition of interphase nuclei was performed using the ScanView system [Applied Spectral Imaging (ASI)], using an Olympus BX61 microscope with a VDS CCD camera, model 1300DS. For scanning purposes the microscope was equipped with a motorized eight-slide stage (Märzhäuser, Germany). The 3D-images were acquired with dry 403 objective and a 0.633 c-mount (Olympus) taking 11 focal planes per cell. The axial sampling distance between planes, $\Delta z$, was 500 nm. Exposure times were constant at 200 ms (DAPI) and 1,000 ms ($Cy^3$) throughout the experiments. The tissue sample mode with aggregate detection level of 15 was used to enable segmentation of touching cells and optimized aggregate detection. Cells with <21 detected signal were excluded as nonclassified (NC). Approximately 10,000 to 15,000 cells were scanned and analyzed within 60 min. For analyzing the data, the following software modules of the ScanView system (ASI) were used: SpotScan with TeloScan for the detection of nuclei, signals, and aggregates. Such a large size of data must be managed correctly, and it was performed by the ScanView database module—case data manager (CDM). Up to 30,000 classified single cells per mixture were analyzed. The numbers of classified cells analyzed per mouse sample were as follows; for the 1:1,000 dilution about 30,000 cells, for the 1:100 dilution about 10,000 cells, for the 1:20 and 1:10 dilution about 5,000 cells, for the pure normal- and tumor samples about 1,000 cells were analyzed.

3D Image Analysis for Telomeres

Telomere measurements were performed using TeloView for the manual 3D-acquisition (35, 38), TeloScan for the automated 3D-acquisition (11). The integrated intensity of each telomere was calculated based on the linear correlation between telomere length and signal intensity.

Telomeric Aggregates

Telomeric aggregates are defined as clusters of telomeres that cannot be resolved as separate signals at the optical resolution limit of 200 nm (63× oil) and 350 nm (40×) (18, 35, 39).

Statistical Analysis

The statistical significance of the differences was determined using the ANOVA test.

Results

Normal mouse lymphocytes and mouse plasmacytoma cells, MOPC460, were analyzed for their specific telomere signatures using the automated 3D-scanner. The telomere signature comprises parameters such as signal numbers per nucleus, signal intensity, and aggregate formation. The software provides a large set of parameters on the analyzed signals, which include information about the cell's identification in the image gallery, the position of each signal within the nucleus, signal intensity, and the presence of aggregates. The second part of the data sheet summarizes the information specifically to each cell; a third part gives detailed information about the number of telomeres within the cells.

The scanned cells are shown in a gallery on the right hand side for view and selection purposes (FIGS. 12a and 12b). The selected cell of the gallery, displayed in the upper left hand corner of the screen, has detailed information in its lower left hand corner such as the number of detected signals (red number) and the class it has been designated to (white number). The classification of cells is based on the number of telomere signals within each scanned nucleus, as defined by the user. Accordingly, a histogram (bar graph, shown in the lower left hand corner of FIGS. 12a and 12b) is generated displaying the distribution of analyzed cells. The histograms of normal cells (FIG. 12a) and tumor cells (FIG. 12b) differ significantly from each other. The majority of normal cells is classified in the group with >20 signals/cell (FIG. 12a). As indicated in FIG. 12b, tumor cells (MOPC460D) display large aggregates indicated with arrows, and higher numbers of telomere signals per cell (histogram).

The difference between normal mouse lymphocytes and MOPC is illustrated in FIG. 13, directly comparing the distribution of cells in classes based on the signal numbers. The majority of normal cells were classified as >20 signals. The mouse plasmacytoma cells show a shift to higher signal numbers due to repeated breakage-bridge-fusion cycles and aberrant mitosis.

One important step in the initiation of genomic instability, thus in tumor formation, is the formation of telomere aggregates (18). Therefore the presence and the frequency of such aggregates in normal mouse lymphocytes and in mouse plasmacytoma cells was examined (Table 9). The data obtained with TeloScan shows that normal mouse lymphocytes have a background of telomeric aggregates of ~4.3%±0.9%. This is in agreement with earlier data obtained with AxioVision (Carl Zeiss Canada Ltd, Toronto, ON) and TeloView (38) (unpublished data). However, about 87% of the mouse plasmacytoma cells showed the presence of telomeric aggregates (Table 9).

Next the detection limit of the cancer cell detection method based on the telomere signature was tested. A suspension of normal cells was spiked with tumor cells at various concentrations and compared the scanning results with respect to signal numbers in the cells, presence of telomeric aggregates, and signal intensity.

The presence of tumor cells within a population of normal cells showed a shift of cells classified as >20 signals per cell, to cells classified as >40 signals per cell. With increasing concentrations of tumor cells an increased percentile of cells with higher numbers of telomere signals was observed (FIG. 14). The presence of one tumor cell within 1,000 normal cells causes a shift of the classified cells to classes with higher numbers of telomere signals.

With increasing numbers of tumor cells an increasing number of cells being positive for telomeric aggregates would be expected. Therefore the normal cells with spiked with MOPC and the number of cells harboring telomeric aggregates was determined. As expected the percentile of cells positive for telomeric aggregates increased with the amount of tumor cells present (FIG. 15). The analysis showed that the presence of one tumor cell within a population of 1,000 normal cells already display a significant increase of aggregates. All experiments were performed in triplicates. Applying ANOVA the significance was P<0.001 (FIG. 15).

Next the mixture of the cells was examined for signal intensity in correlation to the number of telomeres (FIGS. 16a-16c). As shown in Table 6 the MOPC showed a 4.8 fold higher signal intensity than the normal mouse lymphocytes. The changes of intensity in the presence of tumor cells was analyzed. One tumor cell within 1,000 analyzed cells causes a change in the signature compared with the control (FIGS. 16a-16c), characterized by the appearance of two peaks (FIGS. 16a-16c). The peaks increase with increasing number of tumor cells present in the test mixtures. This change is reproducible comparing the graphs of three independent experiments (FIGS. 16a-16c).

Discussion

The present study documents that 3D automated scanning of telomeres is feasible. It is shown that the sensitivity of detection is one cancer cell in 1,000 normal cells using mouse plasmacytoma cells and normal mouse lymphocytes. Thus, this approach is relevant for the future analysis of clinical samples. The use of this scanning technology in the detection of rare cancer cells, in the screening of risk groups, and in the assessment of treatment success is anticipated. Moreover, it has already shown to have the ability of sub-classifying patient subgroups that could not previously be identified (11). It is also expected to have success in guiding patient treatment decisions based on the recognition of recurrent/aggressive telomere profiles observed at diagnosis (40).

Previous studies with normal cells have demonstrated that telomeres are organized in a non-overlapping fashion (35, 38) in discrete microterritories (41, 42). Telomere attrition and uncapping, lead to the formation of telomeric aggregates, a hallmark of premalignant and tumor cells. These telomeric aggregates within the interphase nucleus lead to breakage-bridge-fusion cycles (43, 44), resulting in the generation of aberrant cells that display an altered 3D organization telomere length.

Cells with deficiencies in telomere maintenance are susceptible to enhanced telomere loss during cell proliferation, resulting in telomere dysfunction and genomic instability. Various cancers have been associated with short telomeres like esophageal squamous cell carcinoma (13). Other data demonstrate that telomere attrition is a common early alteration in many human cancers, including gastric cancer (45, 46), colon cancer (47), lung cancer (48), and breast cancer (6, 49). Telomere dysfunction is also associated with bone marrow failure (50), specifically MGUS and multiple myeloma (51, 52). Very short telomeres are also associated with CLL (53), dyskeratosis congenita (54), pancreatic cancer (55), prostate cancer (9), and Barrett's esophagus, which is associated with an increased risk of esophageal adenocarcinoma (56). These data suggest that the alteration of telomeres is potentially an important tool for cancer diagnostics for a broad range of tumors.

Many studies have focused on the analysis of telomere length (overall telomere length or chromosome-, and chromosome-arm-specific telomere length). There are various methods established to determine telomere length like telomere restriction fragment (TRF) analysis, quantitative PCR, and the single telomere length analysis (STELA) [for review: (57)]. More sensitive methods include fluorescence in situ hybridization (FISH) (54) and the primed in situ (PRINS) labeling technique (58, 59) allowing measurement of telomere lengths.

Not surprisingly, various attempts were made to automate the analysis of telomere length, cell in suspension or fixed on solid surfaces. An example for telomere analysis utilizing cell suspensions is the use of flow-FISH (60-62) or high throughput quantitative FISH (HT Q-FISH) (63), allowing for a high throughput of samples. However, these methods are less sensitive (kB-range) than Q-FISH.

Previously, Narath et al. (64) have automated the telomere length measurements in interphase nuclei. Their scanning method allowed for cell identification, spot counting, and intensity measurement, aided by a fluorescence-based microscopic scanning system. This scanning system is based on a fully motorized microscope using the same motorized stage as we used in this study. For the data acquisition nine focus planes were captured at a sampling distance of 0.5 µm. The processing rate was 6-10 nuclei min$^{-1}$ compared to 160-250 cells min$^{-1}$ with TeloScan described here in our study. Data obtained with this system summarize telomere length.

Based on telomerase activity as a tumor marker (65, 68), an automated platform was developed to measure telomerase activity in live circulating tumor cells (CTC). Purified peripheral blood mononuclear cells (PBMC) would be captured on parylene-C microfilters. The telomerase activity is measured using the TRAP (telomere repeat amplification protocol). This method allows for the isolation and characterization of CTCs, isolating viable cells at a 1500-fold enrichment, but requires radioactive labeling of the samples.

It is believed that no data has been published on the automated 3D scanning of nuclei that permit the assessment of spatial telomere organization in interphase, telomere length, the presence of telomeric aggregates, and telomere numbers. These are the four criteria that define differences between normal and tumor cells. The present approach was to integrate all known milestones of telomeric changes in nuclear architecture during cancer development into one automated assay, extending the parameters from telomere length/intensity by the additional parameters such as the automated cell identification, positioning of the telomeres within the 3D-nucleus, the presence of telomeric aggregates, and the number of telomere signals in the cells. Thus, the automated 3D-genome scanning carried out here quantifies telomere length in interphase nuclei and provides morphological and topological details.

The automation allows for a high throughput of about 10,000-15,000 cells within 1 h using the 40× objective. Mounting the slides with ProLong antifade gold, we also overcame the process of photobleaching, a common problem in fluorescence microscopy, which would otherwise lead to inaccurate measurement of fluorescence intensity (66).

The detection of tumor cells in a mixture of normal and tumor cells, presented here indicates that the 3D scanning approach is able to detect a significant difference between these two cell types. These experiments clearly demonstrate that 3D telomeric scanning is capable of detecting one tumor cell within a population of at least 1,000 normal cells. This sensitivity is comparable with earlier data showing a detection limit of one tumor with amplified MYCN cell within 1,000 nonamplified cells (67).

The fact that changes in the 3D telomeric signatures are universally applicable to lymphoid- and nonlymphoid cancers, to single cell suspensions and tissue (fresh, frozen, or paraffinembedded) could make this automated 3D telomere scanning tool interesting for the clinical setting. In future experiments, the findings will be validated with human samples and prove that this new diagnostic tool may be applicable for early cancer detection, the detection of circulating tumor cells, differential diagnosis, as well as a prognostic marker and for therapy selection. Therefore, it could be anticipated that the automated three-dimensional (3D) genome scanning based on the nuclear architecture of telomeres could be a powerful tool to expand our knowledge on the role of telomere length in human disease and potentially a powerful diagnostic as well as prognostic tool in cancer diagnostics (40). It is envisioned that the new screening platform would be helpful in the assistance of tailoring therapeutic strategies in a personalized manner.

TABLE 9

Signal intensity and aggregate detection in normal mouse lymphocytes and MOPC.

| Sample | Average Signal Intensity (A.U.) | Aggregates/Cell (%) |
|---|---|---|
| Normal Mouse Lymphocytes | 585,991 | 4.3 ± 0.9 |
| MOPC | 2,861,250 | 86.9 ± 2.8 |

The signal intensity of all signals and the presence of telomeric aggregates within three independent scans were analyzed. The signal intensity is given in arbitrary units.

LITERATURE CITED FOR EXAMPLE 8

1. Charames G S, Bapat B. Genomic instability and cancer. Curr Mol Med 2003; 3:589-596.
2. Mai S. Initiation of telomere-mediated chromosomal rearrangements in cancer. J Cell Biochem 2010; 109:1095-1102.
3. Rai R, Zheng H, He H, Luo Y, Multani A, Carpenter P B, Chang S. The function of classical and alternative non-homologous end-joining pathways in the fusion of dysfunctional telomeres. EMBO J. 2010; 29:2598-2610.
4. Lamarche B J, Orazio N I, Weitzman M D. The MRN complex in double-strand break repair and telomere maintenance. FEBS Lett 2010; 584:3682-3695.
5. Griffith J K, Bryant J E, Fordyce C A, Gilliland F D, Joste N E, Moyzis R K. Reduced telomere DNA content is correlated with genomic instability and metastasis in invasive human breast carcinoma. Breast Cancer Res Treat 1999; 54:59-64.
6. Meeker A K, Hicks J L, Gabrielson E, Strauss W M, De Marzo A M, Argani P. Telomere shortening occurs in subsets of normal breast epithelium as well as in situ and invasive carcinoma. Am J Pathol 2004; 164:925-935.
7. Odagiri E, Kanada N, Jibiki K, Demura R, Aikawa E, Demura H. Reduction of telomeric length and c-erbB-2 gene amplification in human breast cancer, fibroadenoma, and gynecomastia. Relationship to histologic grade and clinical parameters. Cancer 1994; 73:2978-2984.
8. Heaphy C M, Fleet T M, Treat E G, Lee S J, Smith A Y, Davis M S, Griffith J K, Fischer E G, Bisoffi M. Organ-wide telomeric status in diseased and disease-free prostatic tissues. Prostate 2010; 70:1471-1479.
9. Meeker A K, Hicks J L, Platz E A, March G E, Bennett C J, Delannoy M J, De Marzo A M. Telomere shortening is an early somatic DNA alteration in human prostate tumorigenesis. Cancer Res 2002; 62:6405-6409.
10. Mirabello L, Yu K, Kraft P, De Vivo I, Hunter D J, Prescott J, Wong J Y, Chatterjee N, Hayes R B, Savage S A. The association of telomere length and genetic variation in telomere biology genes. Hum Mutat 2010; 31:1050-1058.
11. Gadji M, Fortin D, Tsanaclis A M, Garini Y, Katzir N, Wienburg Y, Yan J, Klewes L, Klonisch T, Drouin R, Mai S. Three-dimensional nuclear telomere architecture is associated with differential time to progression and overall survival in glioblastoma patients. Neoplasia 2010; 12:183-191.
12. Ohali A, Avigad S, Ash S, Goshen Y, Luria D, Feinmesser M, Zaizov R, Yaniv I. Telomere length is a prognostic factor in neuroblastoma. Cancer 2006; 107:1391-1399.
13. Zheng Y L, Hu N, Sun Q, Wang C, Taylor P R. Telomere attrition in cancer cells and telomere length in tumor stroma cells predict chromosome instability in esophageal squamous cell carcinoma: A genome-wide analysis. Cancer Res 2009; 69:1604-1614.
14. Knecht H, Bruderlein S, Mai S, Moller P, Sawan B. 3D structural and functional characterization of the transition from Hodgkin to Reed-Sternberg cells. Ann Anat 2010; 192:302-308.
15. Knecht H, Mai S. 3D imaging of telomeres and nuclear architecture: An emerging tool of 3D nano-morphology based diagnosis. J Cell Physiol 2010; September 20 [Epub ahead of print].
16. Knecht H, Sawan B, Lichtensztejn D, Lemieux B, Wellinger R J, Mai S. The 3D nuclear organization of telomeres marks the transition from Hodgkin to Reed-Sternberg cells. Leukemia 2009; 23:565-573.
17. Knecht H, Sawan B, Lichtensztejn Z, Lichtensztejn D, Mai S. 3D telomere FISH defines LMP1-expressing reed-sternberg cells as end-stage cells with telomere-poor "ghost" nuclei and very short telomeres. Lab Invest 2010; 90:611-619.
18. Mai S, Garini Y. The significance of telomeric aggregates in the interphase nuclei of tumor cells. J Cell Biochem 2006; 97:904-915.
19. Denoix P F. Enquete permanent dans les centres anti-cancereaux. Bull Inst Nat Hyg 1946; 1:70-75.
20. Rai K R, Sawitsky A, Cronkite E P, Chanana A D, Levy R N, Pasternack B S. Clinical staging of chronic lymphocytic leukemia. Blood 1975; 46:219-234.
21. Binet J L, Auquier A, Dighiero G, Chastang C, Piguet H, Goasguen J, Vaugier G, Potron G, Colona P, Oberling F, et al. A new prognostic classification of chronic lymphocytic leukemia derived from a multivariate survival analysis. Cancer 1981; 48:198-206.
22. van 't Veer L J, Dai H, van de Vijver M J, He Y D, Hart A A, Mao M, Peterse H L, van der Kooy K, Marton M J, Witteveen A T, et al. Gene expression profiling predicts clinical outcome of breast cancer. Nature 2002; 415:530-536.
23. Faca V, Pitteri S J, Newcomb L, Glukhova V, Phanstiel D, Krasnoselsky A, Zhang Q, Struthers J, Wang H, Eng J, et al. Contribution of protein fractionation to depth of analysis of the serum and plasma proteomes. J Proteome Res 2007; 6:3558-3565.
24. Hanash S M, Pitteri S J, Faca V M. Mining the plasma proteome for cancer biomarkers. Nature 2008; 452:571-579.
25. Pitteri S J, JeBailey L, Faca V M, Thorpe J D, Silva M A, Ireton R C, Horton M B, Wang H, Pruitt L C, Zhang Q, et al. Integrated proteomic analysis of human cancer cells and plasma from tumor bearing mice for ovarian cancer biomarker discovery. PLoS One 2009; 4:e7916.
26. Sawyers C L. The cancer biomarker problem. Nature 2008; 452:548-552.
27. Burke H B. Outcome prediction and the future of the TNM staging system. J Natl Cancer Inst 2004; 96:1408-1409.
28. Hammond M E, Taube S E. Issues and barriers to development of clinically useful tumor markers: A development pathway proposal. Semin Oncol 2002; 29:213-221.
29. Ludwig J A, Weinstein J N. Biomarkers in cancer staging, prognosis and treatment selection. Nat Rev Cancer 2005; 5:845-856.
30. Yarbro J W, Page D L, Fielding L P, Partridge E E, Murphy G P. American Joint Committee on Cancer prognostic factors consensus conference. Cancer 1999; 86:2436-2446.

31. Louis S F, Vermolen B J, Garini Y, Young I T, Guffei A, Lichtensztejn Z, Kuttler F, Chuang T C, Moshir S, Mougey V, et al. c-Myc induces chromosomal rearrangements through telomere and chromosome remodeling in the interphase nucleus. Proc Natl Acad Sci USA 2005; 102:9613-9618.
32. Rastan S, Non-random X-chromosome inactivation in mouse X-autosome translocation embryos-Location of the inactivation centre. J Embryol Exp Morphol 1983; 78:1-22.
33. Wiener F, Schmälter A-K, Mowat M R A, Mai S. Duplication of subcytoband 11 E2 of chromosome 11 is regularly associated with accelerated tumor development in v-abl/myc-induced mouse plasmacytomas. Genes and Cancer 2010; 1:847-858
34. Caporali A, Wark L, Vermolen B J, Garini Y, Mai S. Telomeric aggregates and end-to end chromosomal fusions require myc box II. Oncogene 2007; 26:1398-1406.
35. Chuang T C, Moshir S, Garini Y, Chuang A Y, Young I T, Vermolen B, van den Doel R, Mougey V, Perrin M, Braun M, et al. The three-dimensional organization of telomeres in the nucleus of mammalian cells. BMC Biol 2004; 2:12.
36. Kim S H, McQueen P G, Lichtman M K, Shevach E M, Parada L A, Misteli T. Spatial genome organization during T-cell differentiation. Cytogenet Genome Res 2004; 105:292-301.
37. Mai S, Wiener F. Murine FISH. In: Beatty M, Mai S, Squire J, editors. FISH: A Practical Approach. Oxford, UK: Oxford University Press; 2002. pp 55-67.
38. Vermolen B J, Garini Y, Mai S, Mougey V, Fest T, Chuang T C, Chuang A Y, Wark L, Young I T. Characterizing the three-dimensional organization of telomeres. Cytometry A 2005; 67A:144-150.
39. Mai S, Garini Y. Oncogenic remodeling of the three-dimensional organization of the interphase nucleus: c-Myc induces telomeric aggregates whose formation precedes chromosomal rearrangements. Cell Cycle 2005; 4:1327-1331.
40. Knecht H, Kongruttanachok N, Sawan B, Lichtensztejn Z, Lichtensztejn D, Mai S. 3D Telomere Dynamics in Hodgkin's Lymphoma, 52nd ASH Meeting, Orlando, Fla.; 2010.
41. Cremer T, Cremer M. Chromosome Territories. Cold Spring Harb Perspect Biol 2010; 2:a003889.
42. De Vos W H, Hoebe R A, Joss G H, Haffmans W, Baatout S, Van Oostveldt P, Manders E M. Controlled light exposure microscopy reveals dynamic telomere microterritories throughout the cell cycle. Cytometry A 2009; 75A:428-439.
43. McClintock B. The fusion of broken ends of chromosomes following nuclear fusion. Proc Natl Acad Sci USA 1942; 28:458-463.
44. Müller H J. The making of chromosomes. Collecting Net 1938; 13:181-198.
45. Fang D C, Yang S M, Zhou X D, Wang D X, Luo Y H. Telomere erosion is independent of microsatellite instability but related to loss of heterozygosity in gastric cancer. World J Gastroenterol 2001; 7:522-526.
46. Maruyama Y, Hanai H, Fujita M, Kaneko E. Telomere length and telomerase activity in carcinogenesis of the stomach. Jpn J Clin Oncol 1997; 27:216-220.
47. Engelhardt M, Drullinsky P, Guillem J, Moore M A. Telomerase and telomere length in the development and progression of premalignant lesions to colorectal cancer. Clin Cancer Res 1997; 3:1931-1941.
48. Lantuejoul S, Soria J C, Morat L, Lorimier P, Moro-Sibilot D, Sabatier L, Brambilla C, Brambilla E. Telomere shortening and telomerase reverse transcriptase expression in preinvasive bronchial lesions. Clin Cancer Res 2005; 11:2074-2082.
49. Savage S A, Chanock S J, Lissowska J, Brinton L A, Richesson D, Peplonska B, Bardin-Mikolajczak A, Zatonski W, Szeszenia-Dabrowska N, Garcia-Closas M. Genetic variation in five genes important in telomere biology and risk for breast cancer. Br J Cancer 2007; 97:832-836.
50. Savage S A, Alter B P. The role of telomere biology in bone marrow failure and other disorders. Mech Ageing Dev 2008; 129:35-47.
51. Cottliar A, Pedrazzini E, Corrado C, Engelberger M I, Narbaitz M, Slavutsky I. Telomere shortening in patients with plasma cell disorders. Eur J Haematol 2003; 71:334-340.
52. Wu K D, Orme L M, Shaughnessy J Jr, Jacobson J, Barlogie B, Moore M A. Telomerase and telomere length in multiple myeloma: Correlations with disease heterogeneity, cytogenetic status, and overall survival. Blood 2003; 101:4982-4989.
53. Lin T T, Letsolo B T, Jones R E, Rowson J, Pratt G, Hewamana S, Fegan C, Pepper C, Baird D M. Telomere dysfunction and fusion during the progression of chronic lymphocytic leukemia: Evidence for a telomere crisis. Blood 2010; 116:1899-1907.
54. Alter B P, Baerlocher G M, Savage S A, Chanock S J, Weksler B B, Willner J P, Peters J A, Giri N, Lansdorp P M. Very short telomere length by flow fluorescence in situ hybridization identifies patients with dyskeratosis congenita. Blood 2007; 110: 1439-1447.
55. van Heek N T, Meeker A K, Kern S E, Yeo C J, Lillemoe K D, Cameron J L, Offerhaus G J, Hicks J L, Wilentz R E, Goggins M G, et al. Telomere shortening is nearly universal in pancreatic intraepithelial neoplasia. Am J Pathol 2002; 161:1541-1547.
56. Finley J C, Reid B J, Odze R D, Sanchez C A, Galipeau P, Li X, Self S G, Gollahon K A, Blount P L, Rabinovitch P S. Chromosomal instability in Barrett's esophagus is related to telomere shortening. Cancer Epidemiol Biomarkers Prev 2006; 15:1451-1457.
57. Samassekou O, Gadji M, Drouin R, Yan J. Sizing the ends: Normal length of human telomeres. Ann Anat 2010; 192:284-291.
58. Therkelsen A J, Nielsen A, Koch J, Hindkjaer J, Kolvraa S. Staining of human telomeres with primed in situ labeling (PRINS). Cytogenet Cell Genet. 1995; 68:115-118.
59. Yan J, Chen B Z, Bouchard E F, Drouin R. The labeling efficiency of human telomeres is increased by double-strand PRINS. Chromosoma 2004; 113:204-209.
60. Baerlocher G M, Lansdorp P M. Telomere length measurements in leukocyte subsets by automated multicolor flow-FISH. Cytometry A 2003; 55A:1-6.
61. Baerlocher G M, Mak J, Tien T, Lansdorp P M. Telomere length measurement by fluorescence in situ hybridization and flow cytometry: Tips and pitfalls. Cytometry 2002; 47:89-99.
62. Rufer N, Dragowska W, Thornbury G, Roosnek E, Lansdorp P M. Telomere length dynamics in human lymphocyte subpopulations measured by flow cytometry. Nat Biotechnol 1998; 16:743-747.

63. Canela A, Vera E, Klatt P, Blasco M A. High-throughput telomere length quantification by FISH and its application to human population studies. Proc Natl Acad Sci USA 2007; 104:5300-5305.
64. Narath R, Lorch T, Greulich-Bode K M, Boukamp P, Ambros P F. Automatic telomere length measurements in interphase nuclei by IQ-FISH. Cytometry A 2005; 68A: 113-120.
65. Hiyama E, Hiyama K. Telomerase as tumor marker. Cancer Lett 2003; 194:221-233.
66. Poon S S, Lansdorp P M. Quantitative fluorescence in situ hybridization (Q-FISH). Curr Protoc Cell Biol 2001; 14. Chapter 18:unit 18.4.
67. Narath R, Lorch T, Rudas M, Ambros P F. Automatic quantification of gene amplification in clinical samples by IQ-FISH. Cytometry B Clin Cytom 2004; 57B:15-22.
68. Xu T, Lu B, Tai Y C, Goldkorn A. A cancer detection platform which measures telomerase activity from live circulating tumor cells captured on a microfilter. Cancer Res 2010; 70:6420-6426.

While the present disclosure has been described with reference to what are presently considered to be the preferred examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

CITATIONS FOR REFERENCES REFERRED TO IN THE SPECIFICATION

1. Drexler H G, Dirks W G, Macleod R A. Many are called MDS cell lines: one is chosen. Leuk Res. 2009 August; 33(8):1011-6.
2. Ohyashiki K, Iwama H, Yahata N, Tauchi T, Kawakubo K, Shimamoto T, Ohyashiki J H. Telomere dynamics in myelodysplastic syndromes and acute leukemic transformation. Leuk Lymphoma. 2001 July; 42(3):291-9.
3. de Lange T. Shelterin: the protein complex that shapes and safeguards human telomeres. Genes Dev. 2005 Sep. 15; 19(18):2100-10.
4. Callen E, Surralles J. Telomere dysfunction in genome instability syndromes. Mutat Res. 2004 September; 567 (1):85-104.
5. Chuang T C, Moshir S, Garini Y, Chuang A Y, Young I T, Vermolen B, van den Doel R, Mougey V, Perrin M, Braun M, Kerr P D, Fest T, Boukamp P, Mai S. The three-dimensional organization of telomeres in the nucleus of mammalian cells. BMC Biol. 2004; 2:12.
6. Louis S F, Vermolen B J, Garini Y, Young I T, Guffei A, Lichtensztejn Z, Kuttler F, Chuang T C, Moshir S, Mougey V, Chuang A Y, Kerr P D, Fest T, Boukamp P, Mai S. c-Myc induces chromosomal rearrangements through telomere and chromosome remodeling in the interphase nucleus. Proc Natl Acad Sci USA. 2005 Jul. 5; 102(27):9613-8.
7. Mai S, Garini Y. Oncogenic remodeling of the three-dimensional organization of the interphase nucleus: c-Myc induces telomeric aggregates whose formation precedes chromosomal rearrangements. Cell Cycle. 2005 October; 4(10):1327-31.
8. Mai S, Garini Y. The significance of telomeric aggregates in the interphase nuclei of tumor cells. J Cell Biochem. 2006 Apr. 1; 97(5):904-15.
9. Guffei A, Lichtensztejn Z, Goncalves Dos Santos Silva A, Louis S F, Caporali A, Mai S. c-Myc-dependent formation of Robertsonian translocation chromosomes in mouse cells. Neoplasia. 2007 July; 9(7):578-88.
10. Guijon F B, Greulich-Bode K, Paraskevas M, Baker P, Mai S. Premalignant cervical lesions are characterized by dihydrofolate reductase gene amplification and c-Myc overexpression: possible biomarkers. J Low Genit Tract Dis. 2007 October; 11(4):265-72.
11. Knecht H, Sawan B, Lichtensztejn D, Lemieux B, Wellinger R J, Mai S. The 3D nuclear organization of telomeres marks the transition from Hodgkin to Reed-Sternberg cells. Leukemia. 2009 March; 23(3):565-73.
12. Gadji M, Fortin D, Tsanaclis A M C, Yuval G, Katzir N, Wienburg Y, Yan J, Klewes L, Klonisch T, Drouin R, Mai S. Three-dimensional (3D) nuclear telomere architecture is associated with differential time to progression and overall survival in glioblastoma patients. Neoplasia (2): 183-191 2010.
13. Drummond M W, Balabanov S, Holyoake T L, Brummendorf T H. Concise review: Telomere biology in normal and leukemic hematopoietic stem cells. Stem Cells. 2007 August; 25(8):1853-61.
14. Lange K, Holm L, Vang Nielsen K, Hahn A, Hofmann W, Kreipe H, Schlegelberger B, Gohring G. Telomere shortening and chromosomal instability in myelodysplastic syndromes. Genes Chromosomes Cancer. March; 49(3):260-9.
15. Vermolen B J, Garini Y, Mai S, Mougey V, Fest T, Chuang T C, Chuang A Y, Wark L, Young I T. Characterizing the three-dimensional organization of telomeres. Cytometry A. 2005 October; 67(2):144-50.
16. du Manoir S, Speicher M R, Joos S, Schrock E, Popp S, Dohner H, Kovacs G, Robert-Nicoud M, Lichter P, Cremer T. Detection of complete and partial chromosome gains and losses by comparative genomic in situ hybridization. Hum Genet. 1993 February; 90(6):590-610.
17. Barrett M T, Scheffer A, Ben-Dor A, Sampas N, Lipson D, Kincaid R, Tsang P, Curry B, Baird K, Meltzer P S, Yakhini Z, Bruhn L, Laderman S. Comparative genomic hybridization using oligonucleotide microarrays and total genomic DNA. Proc Natl Aced Sci USA. 2004 Dec. 21; 101(51):17765-70.
18. Knecht H, Sawan B, Lichtensztejn Z, Lichtensztejn D, Mai S. 3D telomere FISH defines LMP1 expressing Reed-Sternberg cells as end-stage cells with telomere-poor "ghost" nuclei. Lab Invest. 2010; 90:611-619.

The invention claimed is:

1. A method for providing a clinical outcome prognosis for a subject at a time of diagnosis of a Hodgkin's lymphoma (HL), comprising the steps of:
  a) obtaining a diagnostic lymph node biopsy sample from the subject, the sample comprising Hodgkin cells (H cells) and optionally Reed-Sternberg cells (RS cells);
  b) assaying at least 20 of the H cells of the sample to obtain an H-cell 3D telomeres organization sample signature using 3D q-FISH, the assaying comprising:
    i. nuclear staining the sample by hybridizing the sample with a labelled nucleic acid probe,
    ii. 3D imaging the sample, and
    iii. measuring on the 3D image at least two features to obtain the H-cell 3D telomeres organization sample signature, the at least two features comprising telomere size and at least one of number of telomeres, number of very short telomeres or number of telomere aggregates;

c) obtaining one or more reference 3D telomeres organization signatures selected from i) a RS-cell remission HL 3D telomeres organization reference signature, ii) a RS-cell relapsing or refractory HL 3D telomeres organization reference signature, iii) an H-cell remission HL 3D telomeres organization reference signature or iv) an H-cell relapsing or refractory HL 3D telomeres organization reference signature, each reference 3D telomeres organization signature comprising parameters for the at least two features;

d) comparing the H-cell 3D telomeres organization sample signature to the one or more reference 3D telomeres organization signatures;

e) identifying differences and/or similarities between the H-cell 3D telomeres organization sample signature and the one or more reference 3D telomeres organization signatures; and f) at the time of HL diagnosis, providing the subject or the subject's medical professional with a clinical outcome prognosis according to the identified differences and/or similarities, wherein the clinical outcome prognosis is:

i) an increased likelihood of relapse and/or refractory disease when the H-cell 3D telomere organization sample signature has a decrease in telomere size and one or more of an increase in the number of telomeres, an increase in the number of very short telomeres and an increase in the number of telomere aggregates compared to the H-cell remission HL 3D telomeres organization reference signature or when the H-cell 3D telomere organization sample signature is statistically similar to the RS-cell remission HL 3D telomeres organization reference signature, the RS-cell relapsing or refractory HL 3D telomeres organization reference signature or the H-cell relapsing or refractory HL 3D telomeres organization reference signature or ii) an increased likelihood of remission when the H-cell 3D telomere organization sample signature is statistically similar to the H-cell remission HL 3D telomeres organization reference signature.

2. The method of claim 1, wherein the sample comprises paraffin embedded cells comprising the H cells and optionally the RS cells, and the method comprises deparaffinizing the sample in xylene washes and hydrating the sample in an ethanol-water gradient prior to using 3D q-FISH.

3. The method of claim 1, wherein when the subject is identified as having an increased likelihood of relapse and/or refractory disease, the subject is subsequently treated with 6 to 8 cycles of Adriamycin, Bleomycin, Vinblastine and Dacarbazine (ABVD) chemotherapy and when the subject is identified as having an increased likelihood of remission, the subject is subsequently treated with 1 to 4 cycles of ABVD chemotherapy.

4. The method of claim 1, wherein the RS-cell relapsing or refractory HL 3D telomeres organization reference signature comprises RS cells that contain at least 70%, at least 75%, at least 80% or at least 85% very short telomeres per cell.

5. The method of claim 1, wherein the H-cell relapsing or refractory HL 3D telomeres organization reference signature comprises H cells that contain at least 50%, at least 55%, at least 60% at least 65%, at least 70% or at least 75% very short telomeres per cell.

6. The method of claim 1, wherein a decreased number of telomere aggregates in the H-cell 3D telomeres organization sample signature compared to the H-cell relapsing or refractory HL 3D telomeres organization reference signature and/or the RS-cell relapsing or refractory HL 3D telomeres organization reference signature is indicative of an increased likelihood of remission.

7. The method of claim 1, wherein the H-cell relapsing or refractory HL 3D telomeres organization reference signature comprises H cells that contain an average of at least about 2, at least about 2.5, at least about 3, at least about 3.5, or at least about 4 aggregates per cell.

8. The method of claim 1, wherein the RS-cell relapsing or refractory HL 3D telomeres organization reference signature comprises RS cells that contain an average of at least about 3.5, at least about 4, at least about 4.5, at least about 5, at least about 5.5, or at least about 6 aggregates per cell.

9. The method of claim 1, wherein the sample is a tissue section having a thickness of about 5 microns to about 15 microns.

10. The method of claim 1, further comprising assaying at least 20 of the RS cells to obtain a RS cell 3D telomeres organization sample signature and comparing the RS cell 3D telomeres organization sample signature to the RS cell remission HL 3D telomeres organization reference signature and/or the RS cell relapsing or refractory HL 3D telomeres organization reference signature.

11. The method of claim 10, wherein a statistically similar number of telomere aggregates and/or very short telomeres in the RS cell 3D telomeres organization sample signature compared to the H cell 3D telomeres organization sample signature is indicative of an increased likelihood of relapse and/or refractory disease.

12. The method of claim 1, wherein the 3D imaging the sample comprises obtaining a stack of at least 40 images with a sampling distance of 200 nm along a z direction and 107 nm in each of a x and y direction.

13. The method of claim 1, wherein prior to 3D imaging, the sample is mounted using an antifade mounting medium.

14. A method of providing a personalized treatment plan for a subject at a time of HL diagnosis, comprising the steps of:

a) obtaining a diagnostic lymph node biopsy sample from the subject, the sample comprising Hodgkin cells (H cells) and optionally Reed-Sternberg cells (RS cells);

b) assaying at least 20 of the H cells of the sample to obtain an H-cell 3D telomeres organization sample signature using 3D q-FISH, the assaying comprising:
   i. nuclear staining the sample by hybridizing the sample with a labelled nucleic acid probe,
   ii. 3D imaging the sample, and
   iii. measuring on the 3D image at least two features to obtain the H-cell 3D telomeres organization sample signature, the at least two features comprising telomere size and at least one of number of telomeres, number of very short telomeres or number of telomere aggregates;

c) identifying the subject as having an increased likelihood of relapse and/or refractory disease when the H-cell 3D telomeres organization sample signature is statistically similar to the RS-cell 3D telomeres organization sample signature or as not having an increased likelihood of relapse and/or refractory disease when the H-cell 3D telomeres organization sample signature that is not statistically similar to the RS-cell 3D telomeres organization sample signature; and
d) at the time of HL diagnosis, providing the subject a treatment plan to be administered to the subject when the subject is identified as having an increased likelihood of relapse and/or refractory disease or identified as not having an increased likelihood of relapse and/or refractory disease.

15. The method of claim 14, wherein the treatment plan is 6 to 8 cycles of ABVD chemotherapy when the subject is identified as having an increased likelihood of relapse and/or refractory disease and the treatment plan is 1 to 4 cycles of ABVD chemotherapy when the subject is identified as not having an increased likelihood of relapse and/or refractory disease.

16. A method for providing a clinical outcome prognosis for a subject at a time of diagnosis of a Hodgkin's lymphoma (HL), comprising the steps of:
    a) obtaining a subject diagnostic lymph node sample comprising paraffin embedded cells comprising Hodgkin cells (H cells) and optionally Reed-Sternberg cells (RS cells);
    b) deparaffinizing the sample in xylene washes, hydrating the sample in an ethanol-water gradient;
    c) assaying at least 20 of the H cells of the deparaffinized sample to obtain an H-cell 3D telomeres organization sample signature using 3D q-FISH, the assaying comprising:
       i. nuclear staining the sample by hybridizing the sample with a labelled nucleic acid probe,
       ii. 3D imaging the sample and
       iii. measuring on the 3D image at least two features to obtain the H-cell 3D telomeres organization sample signature, the at least two features comprising telomere size and at least one of number of very short telomeres or number of telomere aggregates; and
    d) at the time of HL diagnosis providing the subject or the subject's medical professional at time of HL diagnosis with a clinical outcome prognosis that the subject is unlikely to progress and/or relapse when in the H cells in the diagnostic lymph node sample less than 50% of the average number of telomeres per cell are very short telomeres and/or the H cells contain an average of less than about 2 aggregates per cell.

17. A method of treating a subject with Hodgkin's lymphoma (HL) comprising:
    providing the subject with the clinical outcome prognosis according to the method of claim 16, wherein the prognosis is that the subject is unlikely to progress and/or relapse, and
    treating the subject with 1 to 4 cycles of ABVD chemotherapy.

18. A method for providing a clinical outcome prognosis for a subject having monoclonal gammopathy of undetermined significance (MGUS), multiple myeloma (MM) or relapsed MM, comprising the steps of:
    a) obtaining a peripheral blood sample from the subject having been diagnosed with MGUS, MM or relapsed MM and the sample comprising plasma cells;
    b) assaying at least 20 of the peripheral blood plasma cells of the sample to obtain a 3D telomeres organization sample signature using 3D q-FISH, the assaying comprising nuclear staining the sample by hybridizing the sample with a labelled nucleic acid probe, 3D imaging the sample and analyzing the 3D image to obtain the 3D telomeres organization sample signature, the 3D telomeres organization sample signature comprising at least two features selected from telomere number, telomere size, number of telomere aggregates, distances from nuclear centre and a/c ratio;
    c) comparing the 3D telomeres organization sample signature to one or more reference 3D telomeres organization signatures for MGUS, MM and/or relapsed MM, each reference 3D telomeres organization signature defining two or more of the features of a 3D telomeres organization signature associated with a clinical outcome;
    d) identifying differences and/or similarities between the 3D telomeres organization sample signature and the one or more reference 3D telomeres organization signatures; and
    e) at the time of MGUS, MM or relapsed MM diagnosis, providing the subject or the subject's medical professional with a clinical outcome prognosis according to the identified differences and/or similarities, wherein the clinical outcome prognosis is a likelihood of MGUS, MM or relapsed MM progression.

19. The method of claim 18, wherein the subject has multiple myeloma (MM).

20. The method of claim 19, wherein the comparing step comprises:
    1) providing one or more reference 3D telomeres organization sample signatures selected from a MGUS 3D telomeres organization reference signature, a MM 3D telomeres organization reference signature and a relapsed MM 3D telomeres organization reference signature; and
    2) identifying the reference 3D telomeres organization signature most similar to the 3D telomeres organization sample signature and a difference or similarity between the 3D telomeres organization sample signature and the reference 3D telomeres organization signature is indicative of the clinical outcome of the subject.

21. The method of claim 18, wherein the subject has MGUS and the comparing step comprises
    comparing the 3D telomeres organization signature of the sample with a reference 3D telomeres organization signature comprising number of telomeres and number of telomere aggregates,
    wherein detecting an increase in the number of telomere numbers and/or the number of telomere aggregates in the 3D telomeres organization sample signature compared to the reference 3D telomeres organization signature, is indicative of an increased likelihood of progression to MM.

22. The method of claim 18, wherein the subject has MM and the comparing step comprises
    comparing the 3D telomeres organization signature of the sample with a reference 3D telomeres organization signature comprising number of telomeres and number of telomere aggregates, and
    wherein detecting a decrease in the number of telomere and/or an increase in the number of telomere aggregates in the 3D telomeres organization sample signature compared to the reference 3D telomeres organization signature, which is indicative of an increased likelihood of MM relapse.

23. The method of claim 22, wherein the reference 3D telomeres organization signature comprises a 3D telomeres organization signature of a sample from a subject with MM that has not relapsed.

24. A method for providing a clinical outcome prognosis at time of diagnosis for a subject having a Hodgkin's lymphoma (HL), comprising the steps of:

a) obtaining a subject diagnostic lymph node sample comprising paraffin embedded cells comprising Hodgkin cells (H cells) and optionally Reed-Sternberg cells (RS cells);
b) deparaffinizing the sample in xylene washes, hydrating the sample in an ethanol-water gradient;
c) assaying at least 20 of the H cells of the deparaffinized sample to obtain an H-cell 3D telomeres organization sample signature using 3D q-FISH, the assaying comprising:
   i. nuclear staining the sample by hybridizing the sample with a labelled nucleic acid probe,
   ii. 3D imaging the sample, and
   iii. measuring on the 3D image at least two features to obtain the H-cell 3D telomeres organization sample signature, the at least two features comprising telomere size and at least one of number of very short telomeres, or number of telomere aggregates; and
d) at the time of HL diagnosis, providing the subject or the subject's medical professional at time of HL diagnosis with a clinical outcome prognosis that the subject is likely to progress and/or relapse when in the H cells in the diagnostic lymph node sample greater than 50% of the average number of telomeres per cell are very short telomeres and/or the H cells contain an average of at least about 2 aggregates per cell.

* * * * *

UNITED STATES PATENT AND TRADEMARK OFFICE
CERTIFICATE OF CORRECTION

PATENT NO. : 9,963,745 B2
APPLICATION NO. : 13/692645
DATED : May 8, 2018
INVENTOR(S) : Sabine Mai et al.

Page 1 of 1

It is certified that error appears in the above-identified patent and that said Letters Patent is hereby corrected as shown below:

On the Title Page

Item (71), Applicant "Tokunbo Ibikunle, Haverford, PA (US)" should be deleted.

Signed and Sealed this
Nineteenth Day of June, 2018

Andrei Iancu
*Director of the United States Patent and Trademark Office*